(12) United States Patent
Liu et al.

(10) Patent No.: US 9,359,372 B2
(45) Date of Patent: Jun. 7, 2016

(54) HEXAHYDRODIBENZO[A,G]QUINOLIZINE COMPOUND, PREPARATION METHOD THEREOF, PHARMACEUTICAL COMPOSITION AND USE THEREOF

(71) Applicant: SHANGHAI INSTITUTE OF MATERIA MEDICA, CHINESE ACADEMY OF SCIENCES, Shanghai (CN)

(72) Inventors: Hong Liu, Shanghai (CN); Xin Xie, Shanghai (CN); Xuechu Zhen, Shanghai (CN); Haifeng Sun, Shanghai (CN); Jing Li, Shanghai (CN); Liyuan Zhu, Shanghai (CN); Zeng Li, Shanghai (CN); Ying Chen, Shanghai (CN); Hualiang Jiang, Shanghai (CN); Kaixian Chen, Shanghai (CN)

(73) Assignee: SHANGHAI INSTITUTE OF MATERIA MEDICA, CHINESE ACADEMY OF SCIENCES, Shanghai (CN)

(*) Notice: Subject to any disclaimer, the term of this patent is extended or adjusted under 35 U.S.C. 154(b) by 0 days.

(21) Appl. No.: 14/683,726

(22) Filed: Apr. 10, 2015

(65) Prior Publication Data
US 2015/0210711 A1    Jul. 30, 2015

Related U.S. Application Data

(60) Division of application No. 14/091,979, filed on Nov. 27, 2013, now abandoned, which is a continuation-in-part of application No. PCT/CN2012/073661, filed on Apr. 9, 2012.

(30) Foreign Application Priority Data

May 27, 2011    (CN) .......................... 2011 1 0141822

(51) Int. Cl.
| | | |
|---|---|---|
| A61K 31/4741 | (2006.01) |
| C07D 491/12 | (2006.01) |
| C07D 491/153 | (2006.01) |
| C07D 455/03 | (2006.01) |
| C07D 491/147 | (2006.01) |
| C07D 491/22 | (2006.01) |
| C07C 69/736 | (2006.01) |
| C07C 231/14 | (2006.01) |
| C07D 217/20 | (2006.01) |
| C07D 311/20 | (2006.01) |
| C07D 491/056 | (2006.01) |

(52) U.S. Cl.
CPC .......... *C07D 491/153* (2013.01); *C07C 69/736* (2013.01); *C07C 231/14* (2013.01); *C07D 217/20* (2013.01); *C07D 311/20* (2013.01); *C07D 455/03* (2013.01); *C07D 491/056* (2013.01); *C07D 491/147* (2013.01); *C07D 491/22* (2013.01)

(58) Field of Classification Search
USPC ............................................ 514/280; 546/48
See application file for complete search history.

(56) References Cited

FOREIGN PATENT DOCUMENTS

| | | |
|---|---|---|
| CN | 1087516 A | 6/1994 |
| CN | 1603324 A | 4/2005 |
| CN | 1900076 A | 1/2007 |
| FR | 5644 M | 12/1967 |
| WO | 2008014661 A1 | 2/2008 |

OTHER PUBLICATIONS

Hanaoka, M. et al.: Chemical transformation of Protoberberines.XI. A novel synthesis of 2,3,10,11-tetraoxygenated Protoberberine alkaloids from corresponding 2,3,9,10-tetraoxygenated Protoberberine alkaloids. Chem. Pharm. Bull., vol. 35, pp. 195-199, 1987.*

(Continued)

*Primary Examiner* — Charanjit Aulakh
(74) *Attorney, Agent, or Firm* — Panitch Schwarze Belisario & Nadel LLP

(57) ABSTRACT

The present invention relates to a novel hexahydrodibenzo[a,g]quinoline compound represented by general formula (I) and its derivatives, enantiomer, diastereoisomer, raceme and mixtures thereof, as well as pharmaceutically acceptable salts thereof. The present invention further relates to a method for preparing the compound, and the compound has good prevention and treatment effect on neurological diseases, especially diseases associated with dopamine receptor and 5-hydroxytryptamine receptor. The bioactivity experiment demonstrates that, the compound is expected to be developed into a novel and potent chemical entity for treating diseases associated with dopamine receptor and 5-hydroxytryptamine receptor, especially schizophrenia, Parkinson's disease, drug addiction, migraine and so on.

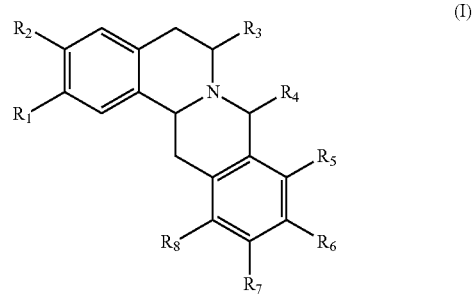

(I)

13 Claims, 3 Drawing Sheets

(56) References Cited

OTHER PUBLICATIONS

Int'l Search Report issued Jul. 12, 2012 in Int'l Application No. PCT/CN2012/073661.

Acta Pharmaceutica Sinica, vol. 25, No. 10, pp. 780-784 (1990).

Acta Chimica Sinica, vol. 30, No. 2, pp. 193-196 (1964).

Sheppard et al, "The Dopamine-Sensitive Adenylate Cyclase of the Rat Caudate Nucleus—3. The Effect of Aporphines and Protoberberines," Biochemical Pharmacology, vol. 27, pp. 1113-1116 (1978).

Mehra et al, "Alkaloids of Corydalis govaniana Wall. : Isolation & Structures of Three New Tetrahydroprotoberberine Alkaloids, Corygovanine, Govadine & Govanine & of a Known Phthalideisoquinoline Base, Bicuculline," Indian Journal of Chemistry, vol. 148, pp. 844-848 (Nov. 1976).

Stambach et al, "Phosgenation of Benzyltetrahydroisoquinolines—A new method of berbines and berbin-8-ones synthesis," Tetrahedron, vol. 41, No. 1, pp. 169-172 (1985).

Semonsky et al, "Synthesa 3,11,12,13-Tetramethoxyberbinu A Jeho Oxydace NA 3,11,12,13-Tetramethoxyprotoberberin," Chem. Listy, pp. 1374-1378 (1953).

Bruderer et al, "Synthese und absolute Konfiguration chiraler 2,3,10,11-Tetrahydroxy-8-methyl-berbine," Helvetica Chemica Acta, vol. 59, Fasc. 8, No. 299, pp. 2793-2807 (1976).

Lenz, "Enamide Photochemistry. Synthesis of Protoberberine Iodides from 1-Benzylidene-3,4-dihydro-2(1H)-isoquinoline Carboxaldehydes," J. Org. Chem., vol. 42, No. 7, pp. 1117-1122 (1977).

Takano et al, "New Synthesis of (+-)-Emetine from Tetrahydroprotoberberine Precursors via an alpha-Diketone Monothioketal Intermediate," J. Org. Chem., vol. 43, No. 21, pp, 4169-4172 (1978).

Iwasa et al, "Biotransformation of Phenolic Tetrahydroprotoberberines in Plant Cell Cultures Followed by LC-NMR, LC-MS, and LC-CD," J. Nat. Prod., vol. 73, pp. 115-122 (2010).

Wiegrebe, "Das Verhalten von MEthylendioxybenzulisochinolinen unter den Bedingungen der Coralyn-Reaktion," Archie der Pharmazie, pp. 708-716 (1967).

Jin et al, "(-)-Stepholidine: a potential novel antipsychotic drug with dual D1 receptor agonist and D2 receptor antagonist actions," Trends in Pharmacological Sciences, vol. 23, No. 1, pp. 4-7 (Jan. 2002).

* cited by examiner

HEXAHYDRODIBENZO[A,G]QUINOLIZINE COMPOUND, PREPARATION METHOD THEREOF, PHARMACEUTICAL COMPOSITION AND USE THEREOF

CROSS-REFERENCE TO RELATED APPLICATIONS

This application is a divisional application of U.S. patent application Ser. No. 14/091,979, filed Nov. 27, 2013, which is a continuation-in-part application of International Application No. PCT/CN2012/073661 filed Apr. 9, 2012, which was published in the Chinese language on Dec. 6, 2012, under International Publication No. WO 2012/163179 A1, the disclosure of which is incorporated herein by reference.

TECHNICAL FIELD

The present invention relates to the field of pharmaceutical chemistry and chemotherapy. Specifically, the present invention relates to a hexahydro-dibenzo[a,g]quinolizine compound (I) with novel structure and derivatives, preparation method thereof, pharmaceutical composition and use thereof for the preparation of medicaments for treating neurological diseases relating to dopamine receptor and serotonin receptor, in particular Parkinson's disease, schizophrenia, drug addiction, migraine headaches and the like.

BACKGROUND ART

Nervous system disease is one of prevalent diseases in contemporary society. However, many types of nervous system diseases have not yet been effectively addressed in clinical practice. In particular, the treatments for neurological diseases such as schizophrenia, Parkinson's disease and the like are still very far from achieving satisfactory results. In recent years, studies have shown that schizophrenia is considered as the result of $D_1$ receptor dysfunction of medial prefrontal cortex (mPFC) and thus enhancing the activity of $D_2$ receptor of the ventral tegmental area (VTA) and the nucleus accumbens region (NAc). By carrying out working memory experiments for animals and patients, short-term experiments reflecting the function of medial prefrontal cortex and clinical trials, scientists have demonstrated that the inactivation of $D_1$ receptor is related to the negative symptoms of schizophrenia and high activity of $D_2$ receptor generates the positive symptoms. Based on such hypothesis, if a class of medicaments can effectively excite the activity of $D_1$ receptor, and antagonize activity of $D_2$ receptor in the meantime, such medicaments should have good prospects for the treatment of schizophrenia.

Parkinson's disease is a chronic progressive degenerative diseasea with brain dopaminergic neuron loss as main feature. For a long time, L-Dopamine is a "gold standard" for the treatment of Parkinson's disease. However, long-term administration of L-Dopamine is often accompanied by high incidence of treatment-related complications, such as dyskinesias, efficacy loss and "on-off" phenomenon and the like, which are named as "L-Dopamine long-term syndrome" and can not delay disease progression.

DA receptor agonist is one of various substitutive therapies for Parkinson's disease and mainly used with L-Dopamine in Parkinson patients having dyskinesia. DA receptor agonist is superior to L-Dopamine, the mechanism of which is that in the later stages of Parkinson's disease, dopamine decarboxylase activity of the nigrostriatal DA system is depleted, therefore, exogenous L-Dopamine can not be transformed into DA through decarboxylation, and at that time, even a large dose of L-Dopamine preparations is ineffective; however, the function of DA receptor agonist is irrelevant to DA synthesis and does not depend on the activity of dopa decarboxylase, the molecular conformation thereof is similar to that of DA, DA receptor agonist works by directly acting on striatal synaptic DA receptor, primarily $D_1$ receptor, in part on $D_2$ receptors; therefore, the combination of DA receptor agonist can further improve motor symptoms of Parkinson's disease. Based on such theory, if $D_1$ receptor agonist with selectivity can be developed, it is possible to provide a class of medicaments with good effect for the treatment of Parkinson's disease. Currently, some companies have developed various $D_1$ receptor selective agonists with selectivity, many of which have been studied in clinical trail, but many medicament candidates have low selectivity and obvious side effect. Therefore, the development of $D_1$ receptor selective agonist with high selectivity and little side effect will undoubtedly have huge advantages for the treatment of Parkinson's disease.

The hexahydrodibenzo[a,g]quinolizine compounds are a class of alkaloids extracted from traditional Chinese medicine Corydalis Tuber and Stephania genus plants, which have a common chemical nucleus containing two-isoquinoline structure and having —$OCH_3$ in $C_2$, $C_3$, $C_9$, and $C_{10}$ or substituted by —OH. Such alkaloids have various biological activities, including anti-inflammatory effect, antibacterial effect, anti-leukemia effect, anti-cancer effect and so on. Academician Jin GuoZhang, et al. have systematically studied the pharmacological effects of hexahydrodibenzo[a,g]quinolizine compounds and demonstrated that levorotatory tetrahydropalmatine has good analgesic effect accompanied by sedation, tranquillizing effect and hypnotic effect, while dextrorotatory tetrahydropalmatine has no significant analgesic effect. It is also demonstrated that the target of levorotatory tetrahydropalmatine or other hexahydrodibenzo[a,g]quinolizine alkaloids is dopamine receptor. Jin Guozhang has also reported for the first time that l-Stepholidine (l-SPD), one of hexahydrodibenzo[a,g]quinolizine compounds (THPBs), is a lead compound with the dual role of $D_1$ agonist and $D_2$ antagonistic activity (Jin G Z. TiPS, 2002, 23-24). l-SPD, in clinical trials, has shown good therapeutic effects on positive and negative symptoms and has non-classical stabilizer features, and can be likely developed into a new class of antipsychotic medicaments. Shen Jingshan, Yang Yushe et al. disclosed a preparation method and use of l-SPD derivatives and levorotatory Chloroscoulerine with antipsychotic effect, wherein Scoulerine methanesulfonate has good water solubility and stability (WO2008/014661, CN03151464, and CN1900076). However, the structures of these compounds are not greatly modified, most of the compounds have weak activity on $D_2$ receptor, and many compounds have no 5-HT activity, poor solubility and low bioavailability. Meanwhile, these compounds showed a certain degree of selectivity in $D_1$ receptor vs $D_2$ receptor. Therefore, it is significant to continually modify hexahydrodibenzo[a,g]quinolizine compounds, especially to develop compounds with better $D_2$ activity or develop $D_1$ receptor agonists with better selectivity, thereby providing beneficial help for treating Parkinson's disease.

The present invention provides the synthesis and use of a class of hexahydro-dibenzo[a,g]quinoline compounds with novel structures. Some compounds with such structures show good selectivity in $D_1$ vs $D_2$ wherein many compounds also have 5-HT activity. Other compounds have dual pharmacological activities of good $D_1$ agonist and $D_2$ antagonist and good solubility, and can be used in the preparation of the medicaments for treating neurological diseases, especially dopamine receptors and serotonin receptor-associated neurological disease.

SUMMARY OF THE INVENTION

One object of the present invention is to provide a hexahydrodibenzo[a,g]quinoline compound of general formula (I), enantiomer, diastereoisomer, racemate and mixtures thereof, the pharmaceutically acceptable organic salt or inorganic salt, crystalline hydrate and solvate thereof.

Another object of the present invention is to provide a preparation method for the compound of general formula (I).

Another object of the present invention is to provide a pharmaceutical composition containing the compound of general formula (I), enantiomer, diastereomer, racemate and mixtures thereof, the pharmaceutically acceptable organic salt or inorganic salt, crystalline hydrate and solvate thereof.

A further object of the present invention is to provide a use of the compound of general formula (I) in the preparation of medicaments for treating the diseases relating to dopamine receptors and serotonin receptors.

Based on above objects, the invention relates to a hexahydrodibenzo[a,g]quinoline compound of general formula (I), enantiomer, diastereoisomer, racemate and mixtures thereof, the pharmaceutically acceptable organic salt or inorganic salt, crystalline hydrate and solvate thereof,

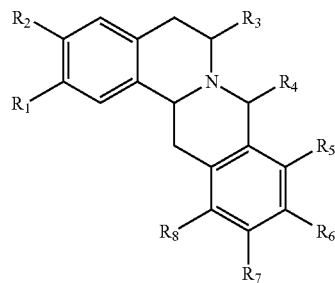

(I)

wherein $R_2$ is a hydroxy, a hydroxy-substituted C1-C6 alkyl, a substituted or unsubstituted C1-C6 alkoxy, a halogen, a substituted or unsubstituted C1-C6 alkyl, a substituted or unsubstituted C2-C6 alkenyl, a substituted or unsubstituted C2-C6 alkynyl, a substituted or unsubstituted C3-C6 cycloalkyl, a substituted or unsubstituted C1-C6 alkanoyl, a substituted or unsubstituted C6-C20 aryl, a substituted or unsubstituted benzyl, an amino acid or N-protected amino acid, or —(CO) $R_9$;

when $R_2$ is a substituted or unsubstituted C1-C6 alkyl, a substituted or unsubstituted C1-C6 alkoxy, a substituted or unsubstituted C2-C6 alkenyl, a substituted or unsubstituted C2-C6 alkynyl, or a substituted or unsubstituted C3-C6 cycloalkyl, a substituent for substitution can be a halogen or $COOR_{10}$;

when $R_2$ is a substituted or unsubstituted C1-C6 alkanoyl, a substituted or unsubstituted C6-C20 aryl, or a substituted or unsubstituted benzyl, a substituent for substitution can be selected from the following group: C1-C6 alkyl, a halogen, and C1-C6 alkoxy;

wherein $R_9$ is a substituted or unsubstituted C1-C6 alkyl, a substituted or unsubstituted C2-C6 alkenyl, a substituted or unsubstituted C2-C6 alkynyl, a substituted or unsubstituted C6-C20 aryl, or heteroaryl selected from thiazolyl, pyrazolyl, imidazolyl, thienyl, furyl, pyrrolyl, or pyridyl;

when $R_9$ is a substituted or unsubstituted C1-C6 alkyl, a substituted or unsubstituted C2-C6 alkenyl, or a substituted or unsubstituted C2-C6 alkynyl, a substituent for substitution can be a carboxyl, a substituted or unsubstituted C6-C20 aryl, or heteroaryl selected from thiazolyl, pyrazolyl, imidazolyl, thienyl, furyl, pyrrolyl, or pyridy;

when $R_9$ is a substituted or unsubstituted C6-C20 aryl, a substituent for substitution can be a C1-C6 alkyl, a halogen or a C1-C6 alkoxy;

$R_{10}$ is H, a C6-C20 alkyl substituted or unsubstituted C1-C6 alkyl, a C2-C6 alkenyl, or a C2-C6 alkynyl;

when $R_2$ is an amino acid or N-protected amino acid, the amino acid can be D-amino acid, L-amino acid or racemate;

each of $R_3$, $R_4$ is independently H, a halogen substituted or unsubstituted C1-C6 alkyl, a halogen substituted or unsubstituted C1-C6 alkoxy, a C2-C6 alkenyl, a C2-C6 alkynyl, halogen, $COOR_{11}$, or $CONR_{12}R_{13}$, wherein $R_{11}$ is H, a substituted or unsubstituted C1-C6 alkyl, a C2-C6 alkenyl, a C2-C6 alkynyl, a substituted or unsubstituted C6-C20 aryl, or a substituted or unsubstituted benzyl;

when $R_{11}$ is a substituted or unsubstituted C6-C20 aryl, or a substituted or unsubstituted benzyl, a substituent for substitution can be a C1-C6 alkyl, a halogen or a C1-C6 alkoxy;

when $R_{11}$ is a substituted or unsubstituted C1-C6 alkyl, a substituent for substitution can be a halogen; each of $R_{13}$, $R_{12}$ is independently selected from H, or a substituted or unsubstituted C1-C6 alkyl, or they and nitrogen atom together form azetidine, pyrrolidinyl, piperazinyl, or morpholinyl; when $R_{13}$ or $R_{12}$ is a substituted or unsubstituted C1-C6 alkyl, a substituent for substitution can be a halogen;

each of $R_1$, $R_5$, $R_6$, $R_7$, $R_8$ is independently H, a hydroxy, a hydroxy-substituted C1-C6 alkyl, a halogen-substituted or unsubstituted C1-C6 alkyl, a halogen substituted or unsubstituted C1-C6 alkoxy, a halogen, a C3-C6 cycloalkyl, a halogen substituted or unsubstituted C2-C6 alkenyloxy, a halogen-substituted or unsubstituted C3-C6 alkynyloxy, a substituted or unsubstituted benzyloxy, a substituted or unsubstituted C6-C20 aryl, $R_{14}COO$—, $R_{15}R_{16}N$—; when $R_1$, $R_5$, $R_6$, $R_7$, or $R_8$ is a substituted or unsubstituted benzyloxy, or a substituted or unsubstituted C6-C20 aryl, a substituent for substitution can be a C1-C6 alkyl, a halogen, or a C1-C6 alkoxy; wherein $R_{14}$ is H, a halogen-substituted or unsubstituted C1-C6 alkyl; each of $R_{15}$ and $R_{16}$ is independently selected from H, a substituted or unsubstituted C1-C6 alkyl, a substituted or unsubstituted C2-C6 alkenyl, or a substituted or unsubstituted C2-C6 alkynyl, or they and nitrogen atom together form azetidine, pyrrolidinyl, piperazinyl, or morpholinyl; when $R_{15}$ or $R_{16}$ is a substituted or unsubstituted C1-C6 alkyl, a substituted or unsubstituted C2-C6 alkenyl, a substituted or unsubstituted C2-C6 alkynyl, a substituent for substitution can be a C1-C6 alkyl, a halogen or a C1-C6 alkoxy;

$R_1$ and $R_2$ can together form a substituted or unsubstituted 5-7 membered heterocycle, wherein a substituent for substitution can be a halogen, or a halogen-substituted or unsubstituted C1-C6 alkyl, C2-C6 alkenyl, or C2-C6 alkynyl; and the heterocycle contains 1-3 heteroatom(s) selected from N, O or S;

any two adjacent substituents of $R_5$, $R_6$, $R_7$ and $R_8$ can together form a substituted or unsubstituted 5-7 membered heterocycle, wherein a substituent for substitution can be a halogen, or a halogen-substituted or unsubstituted C1-C6 alkyl, C2-C6 alkenyl, or C2-C6 alkynyl; and the heterocycle contains 1-3 heteroatom(s) selected from N, O or S;

and the configuration of chiral carbon atom in the compound of general formula (I) is R or S configuration.

Preferably, with the proviso that when the compound of general formula (I) is racemate, the following conditions should be fulfilled:

(a) when $R_2$ is methoxyl, $R_3$ is H, $R_4$ is H or methyl, and at least one of $R_5$, $R_6$, $R_7$, and $R_8$ is methoxyl or $R_6$ and $R_7$ together form —O—CH$_2$—O—, $R_1$ can not be H, methoxyl or BnO;

(b) when $R_1$ and $R_2$ together form —O—CH$_2$—O—, and $R_7$ or $R_8$ is methoxyl, $R_5$ can not be methoxyl;

(c) when $R_6$ and $R_7$ together form —O—CH$_2$—O— and $R_5$ and $R_8$ are H, $R_2$ can not be methoxyl and $R_1$ and $R_2$ can not together form —O—CH$_2$—O—; and (d) the compound of general formula (I) is not DC037027,

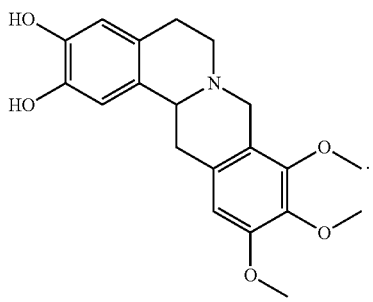

DC037027

Preferably, in the compound, $R_1$ is H, a halogen-substituted or unsubstituted C1-C6 alkyl, a halogen-substituted or unsubstituted C1-C6 alkoxy, a hydroxy, a hydroxy-substituted C1-C6 alkyl or a halogen-substituted or unsubstituted benzyloxy; $R_2$ is a hydroxy, a hydroxy-substituted C1-C6 alkyl, a halogen substituted or unsubstituted C1-C6 alkyl, or a halogen substituted or unsubstituted C1-C6 alkoxy, or a halogen; $R_3$ is H, or a halogen substituted or unsubstituted C1-C6 alkyl; $R_4$ is H, a halogen substituted or unsubstituted C1-C6 alkyl, or a halogen substituted or unsubstituted C1-C6 alkoxy; $R_5$ is H, a halogen substituted or unsubstituted C1-C6 alkyl, a halogen substituted or unsubstituted C1-C6 alkoxy or a halogen; $R_6$ is H, a halogen-substituted or unsubstituted C1-C6 alkyl, a halogen-substituted or unsubstituted C1-C6 alkoxy, a hydroxy, or a hydroxy-substituted C1-C6 alkyl; $R_7$ is H, a halogen-substituted or unsubstituted C1-C6 alkyl, a halogen-substituted or unsubstituted C1-C6 alkoxy, a hydroxy, or a hydroxy-substituted C1-C6 alkyl; $R_8$ is H, a hydroxy, a hydroxy-substituted C1-C6 alkyl, a halogen-substituted or unsubstituted C1-C6 alkoxy, a halogen-substituted or unsubstituted C1-C6 alkyl or a halogen;

or $R_1$ and $R_2$ can together form a C1-C6 alkyl-substituted or unsubstituted 5-7 membered heterocycle, and the heterocycle contains 1-2 heteroatom(s) selected from N, O or S;

$R_6$ and $R_7$ can together form a fluro-, chloro- or bromo-substituted 5-7 membered heterocycle, and the heterocycle contains 1-2 heteroatom(s) selected from N, O or S.

More preferably, $R_1$ is H, a C1-C6 alkyl, a C1-C6 alkoxy, a hydroxy, a hydroxy-substituted C1-C6 alkyl or benzyloxy; $R_2$ is a hydroxy, a hydroxy-substituted C1-C6 alkyl, a C1-C6 alkyl, a C1-C6 alkoxy or a halogen; $R_3$ is H or a C1-C6 alkyl; $R_4$ is H, a C1-C6 alkyl, or a C1-C6 alkoxy; $R_5$ is H, a C1-C6 alkyl, a C1-C6 alkoxy or a halogen; $R_6$ is H, a C1-C6 alkyl, a C1-C6 alkoxy, a hydroxy, or a hydroxy-substituted C1-C6 alkyl; $R_7$ is H, a C1-C6 alkyl, a C1-C6 alkoxy, a hydroxy, or a hydroxy-substituted C1-C6 alkyl; $R_8$ is H, a hydroxy, a hydroxy-substituted C1-C6 alkyl, a C1-C6 alkoxy, a C1-C6 alkyl or a halogen; the halogen is F, Br or Cl;

$R_1$ and $R_2$ can together form a C1-C6 alkyl-substituted or unsubstituted 5- or 6-membered heterocycle, and the heterocycle contains 1-2 heteroatom(s) selected from N, O or S;

$R_6$ and $R_7$ can together form a fluoro-, chloro- or bromo-substituted or unsubstituted 5- or 6-membered heterocycle, and the heterocycle contains 1-2 heteroatom(s) selected from N, O or S.

In another preferable embodiment, the configuration of chiral C atom which is not linked with $R_3$ or $R_4$ in the parent nucleus of compound of general formula (I) is S.

In another preferable embodiment, the configuration of chiral C atom which is not linked with $R_3$ or $R_4$ in the parent nucleus of compound of general formula (I) is R.

In another preferable embodiment, the compound of general formula (I) is chiral compound.

In another preferable embodiment, $R_5$ is methoxyl, and $R_6$ is hydroxyl.

In another preferable embodiment, $R_3$ is a halogen substituted or unsubstituted C1-C6 alkyl, a halogen substituted or unsubstituted C1-C6 alkoxy, a C2-C6 alkenyl, a C2-C6 alkynyl, a halogen, COOR$_{11}$, or CONR$_{12}$R$_{13}$, i.e. $R_3$ is not H.

In another preferable embodiment, $R_8$ is a hydroxy-substituted C1-C6 alkyl, or a halogen.

In another preferable embodiment, one to four of $R_5$, $R_6$, $R_7$, and $R_8$ is a hydroxy-substituted C1-C6 alkyl or C1-C6 alkyl.

Most preferably, the hexahydrodibenzo[a,g]quinoline compound according to the invention, enantiomer, diastereoisomer and racemate thereof are selected from the following compounds:

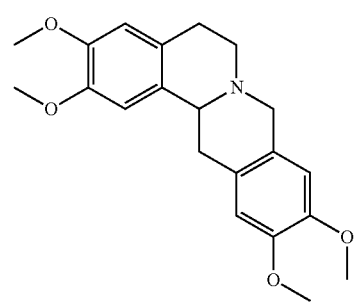

DC037001

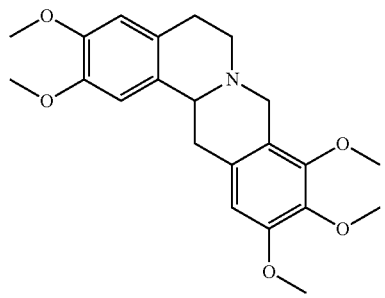

DC037002

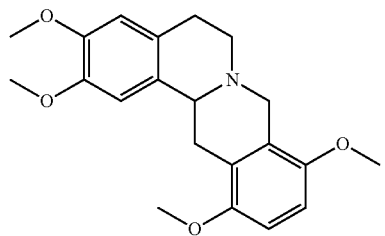

DC037003

DC037004

DC037005

DC037006

DC037007

DC037008

DC037009

DC037010

DC037011

DC037012

DC037013

-continued
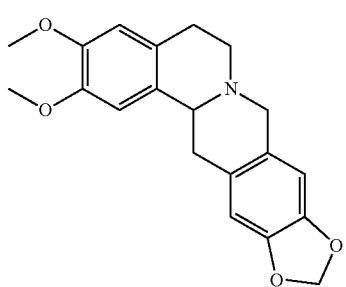 DC037014
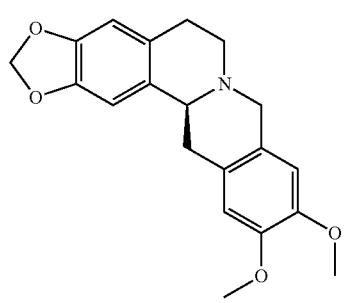 DC037015
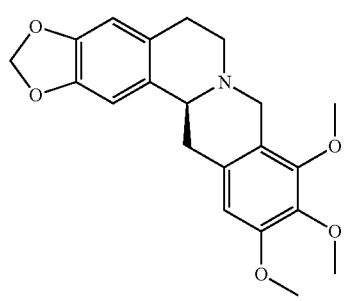 DC037016
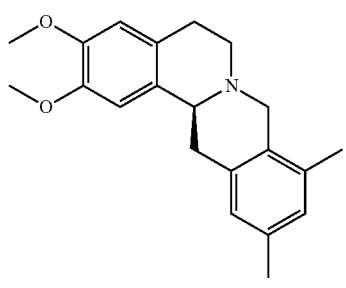 DC037017
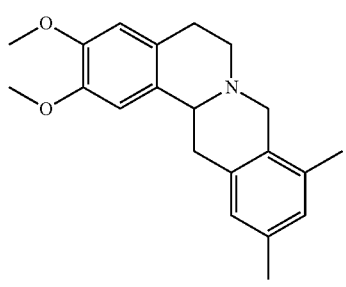 DC037018
-continued
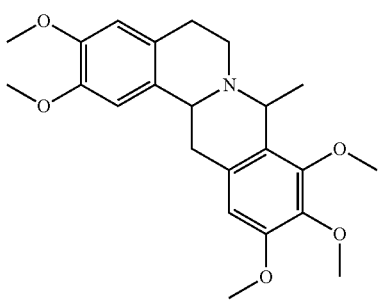 DC037019
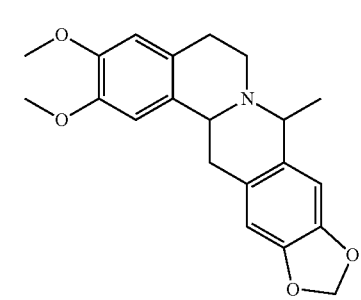 DC037020
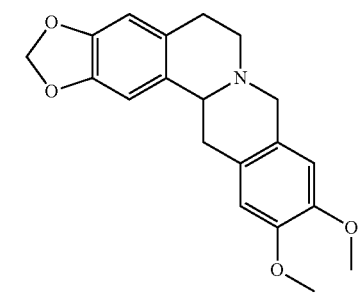 DC037021
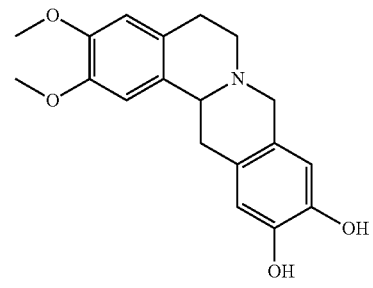 DC037022
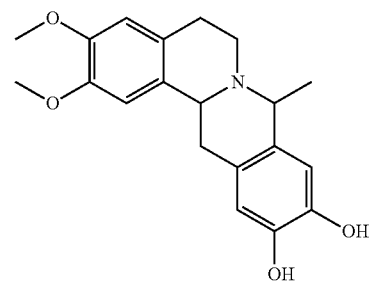 DC037023

DC037024
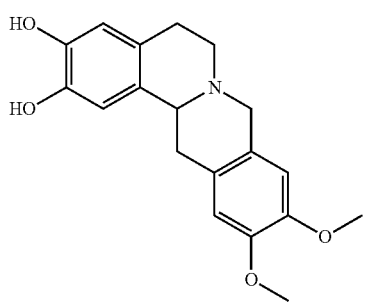
DC037025
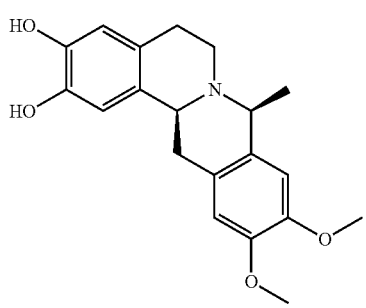
DC037026
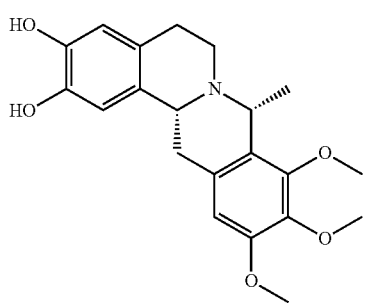
DC037027
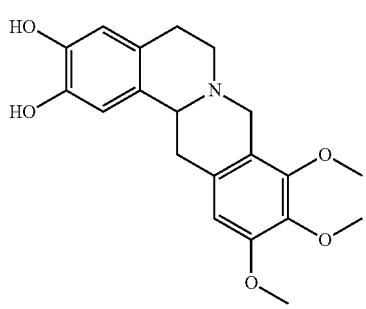
DC037028
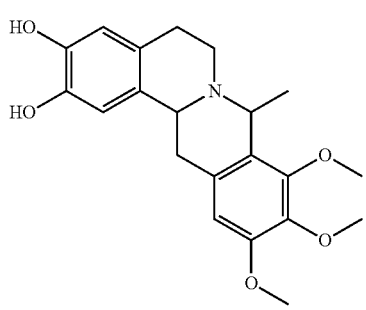
DC0370296
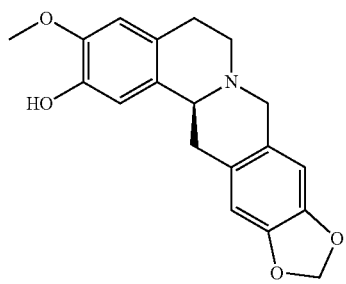
DC037030
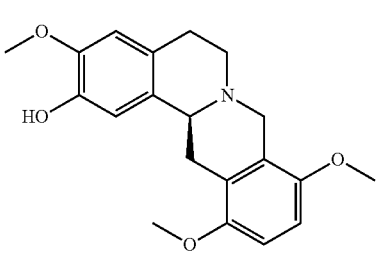
DC037031
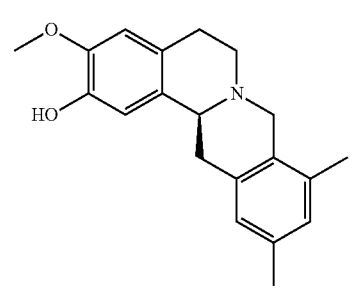
DC037032
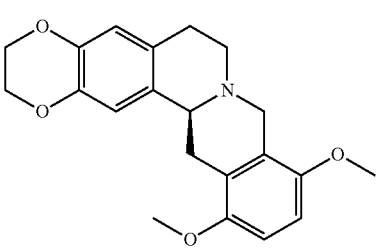
DC037033
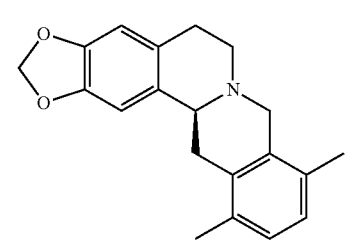
DC037034

DC037035

DC037036

DC037037

DC037038

DC037039

DC037040

DC037041

DC037042

DC037043

DC037044

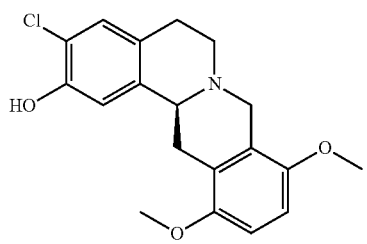
DC037045
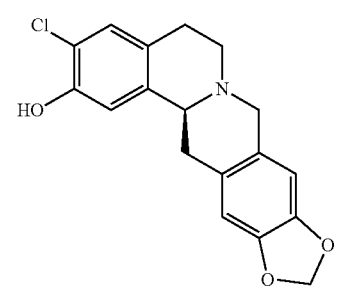
DC037046
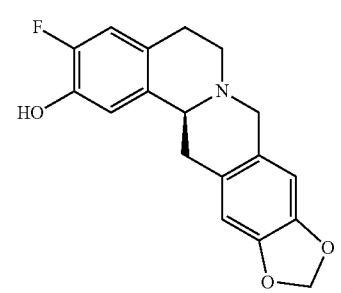
DC037047
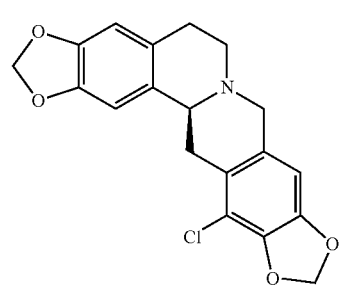
DC037048
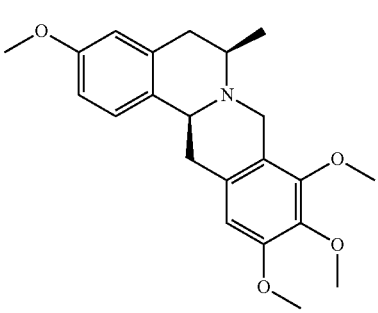
DC037049
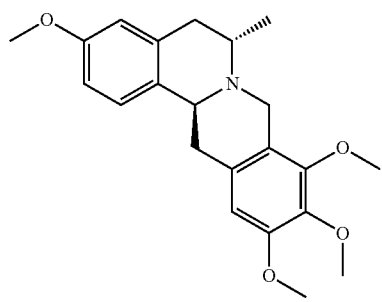
DC037050
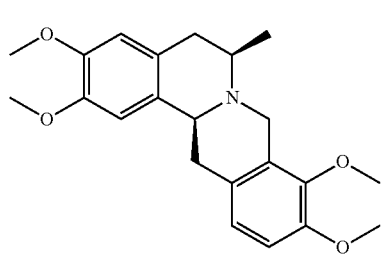
DC037051
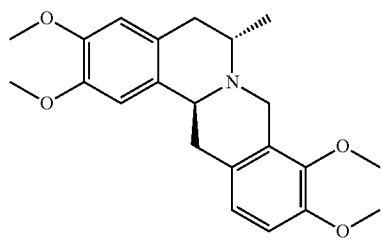
DC037052
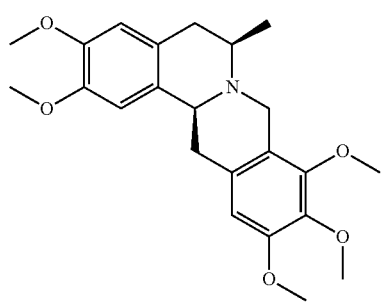
DC037053
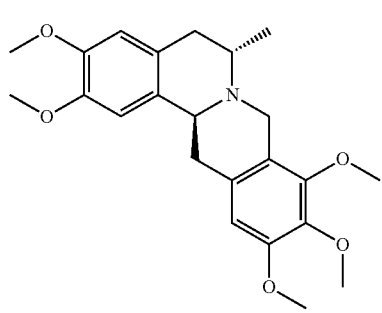
DC037054

-continued
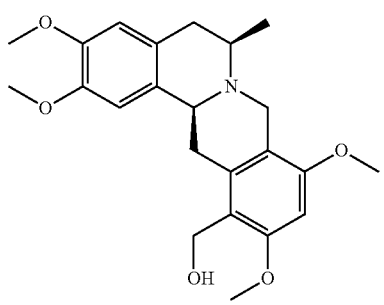
DC037055
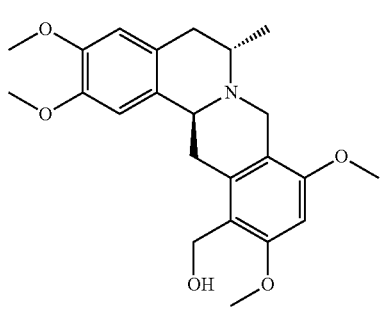
DC037056
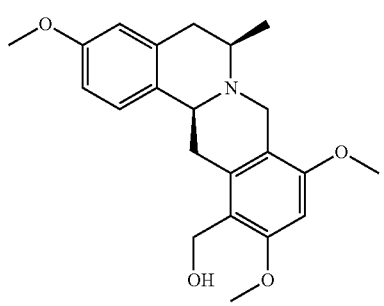
DC037057
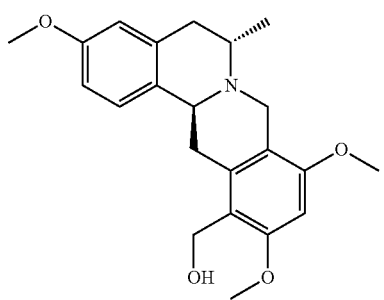
DC037058
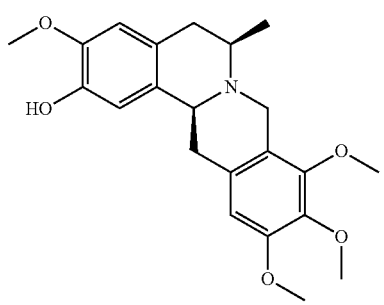
DC037059
-continued
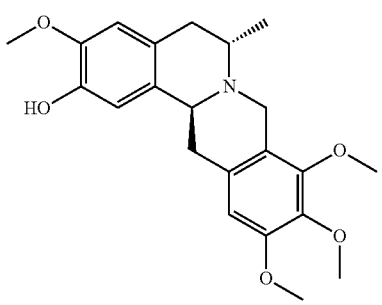
DC037060
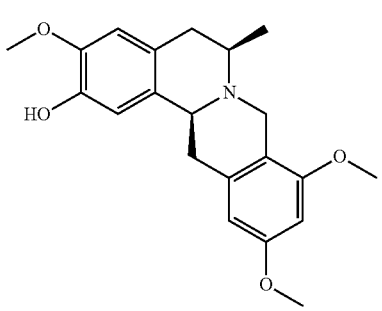
DC037061
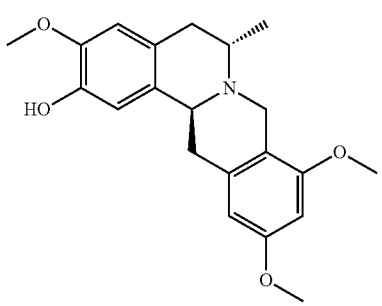
DC037062
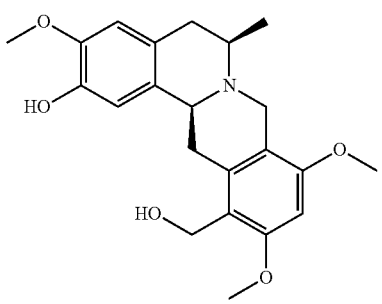
DC037063
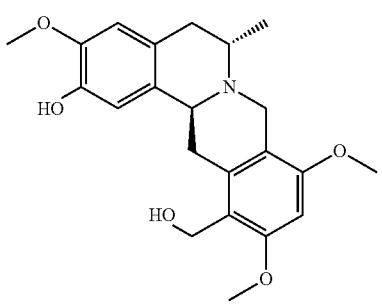
DC037064

-continued
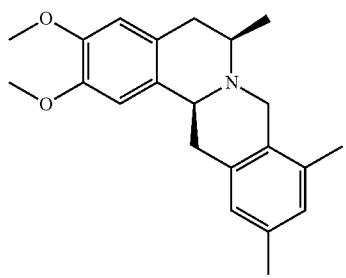
DC037065
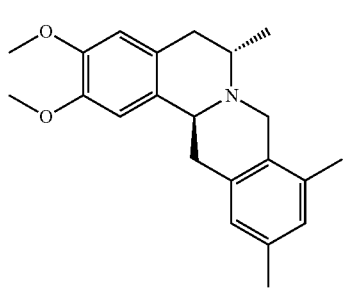
DC037066
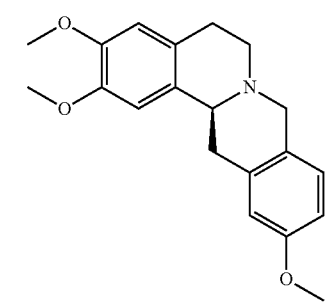
DC037067
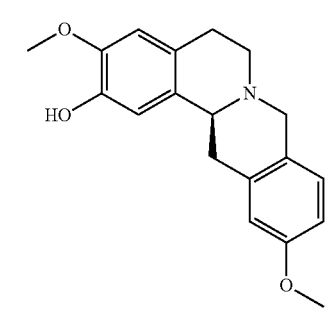
DC037068
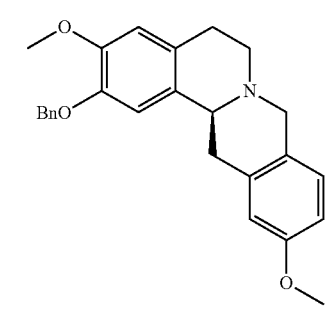
DC037069
-continued
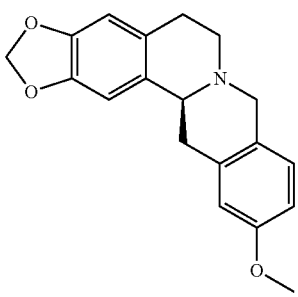
DC037070
DC037071
DC037072
DC037073
DC037074
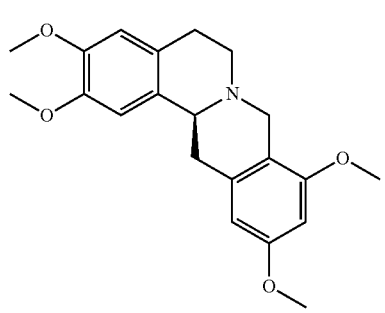
DC037075

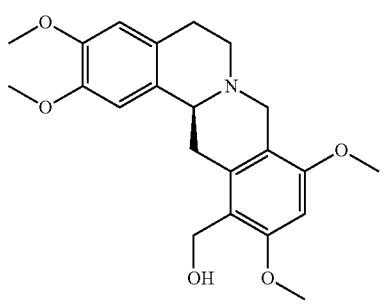
DC037076

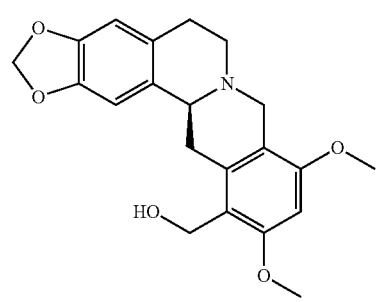
DC037077

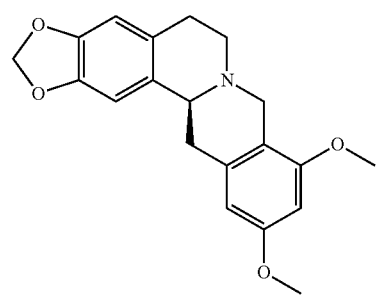
DC037078

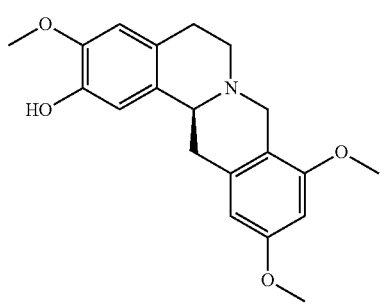
DC037079

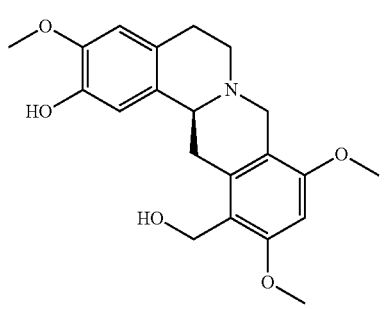
DC037080

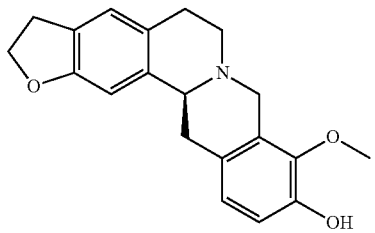
DC037081

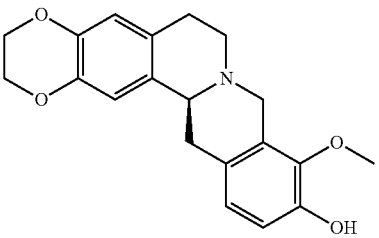
DC037082

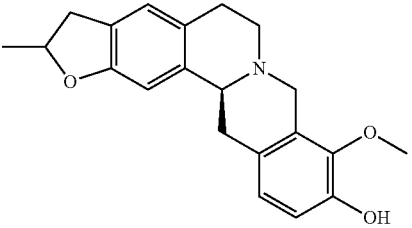
DC037083

The "pharmaceutically acceptable organic salt or inorganic salt" is a slat formed from the reaction of the compound of general formula (I) with inorganic acid, such as hydrochloric acid, hydrobromic acid, hydroiodic acid, hydrofluoric acid, sulfuric acid, nitric acid or phosphoric acid and the like, or with organic acid, such as formic acid, acetic acid, propionic acid, oxalic acid, malonic acid, maleic acid, tartaric acid, malic acid, fumaric acid, methanesulfonic acid, citric acid, ethanesulfonic acid, benzenesulfonic acid, citric acid, lactic acid, aspartic acid or glutamic acid and the like, or a sodium, potassium, calcium or ammonium salt which is formed from the reaction of the compound of general formula (I) with alkali, such as sodium hydroxide, potassium hydroxide, calcium hydroxide or ammonia.

The present invention also provides a preparation method for the compound of general formula (I) and intermediates thereof. The raw materials and reagents used in the present invention are commercially available unless otherwise specified.

Wherein, R1-R4 and R8 are defined as above. When each of R5 and R6 is independently a halogen-substituted or unsubstituted C1-C6 alkoxy, a substituted or unsubstituted benzyloxy (a substituent for substitution is a C1-C6 alkyl, a halogen or a C1-C6 alkoxy), and R7 is H; or when R5 is a halogen-substituted or unsubstituted C1-C6 alkoxy, a substituted or unsubstituted benzyloxy (a substituent is a C1-C6 alkyl, a halogen or a C1-C6 alkoxy), R6 is a hydroxy, and R7 is H, the compounds of general formula (I), including compounds DC037051, DC037052, DC037073, DC037074, DC037081, DC037082 and DC037083, are prepared according to the second reaction route; other compounds of general formula (I) are prepared according to the first reaction route.

The first reaction route:

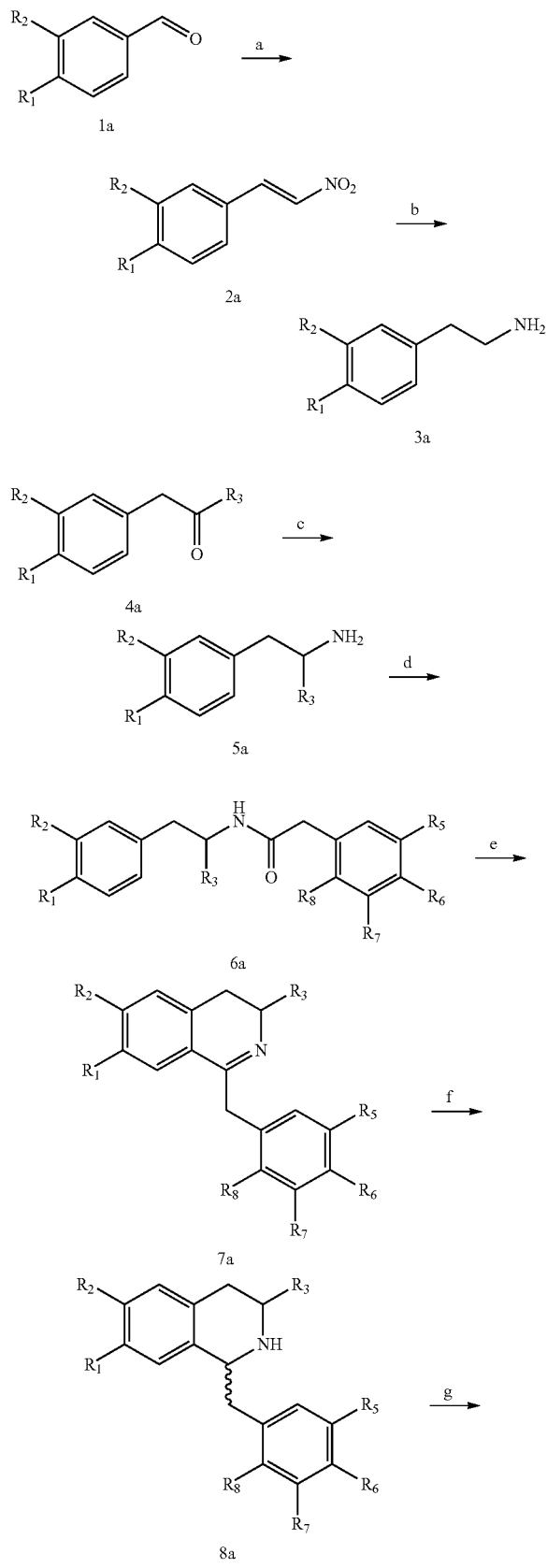

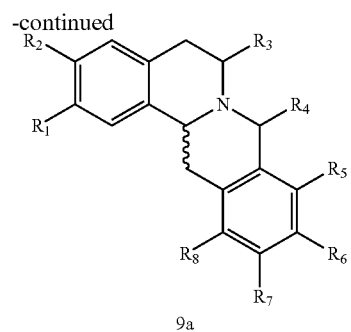

Reagents and reaction conditions: a) acetic acid, nitromethane, ammonium acetate, 80° C.; b) lithium aluminum hydride, anhydrous tetrahydrofuran, reflux; c) ammonium formate, anhydrous methanol, palladium carbon, hydrogen, room temperature; d) 1-ethyl-3-(3-dimethylpropylamine) carbodiimide, anhydrous dichloromethane, triethylamine, room temperature; e) nitrogen protection, phosphorus oxychloride, acetonitrile, reflux; and f) catalyst (Noyori), N, N-dimethylformamide, triethylamine/formic acid or sodium borohydride; g) aldehyde, acid conditions.

The preparation method according to the first reaction route is described in detail as follows.

The preparation of Compound 2a: 10 mmol of substrate (1a, purchased from Alpha Aisha Company) is dissolved in an appropriate amount of glacial acetic acid, to which 1.2-2.0 equivalent of ammonium acetate is added to form a mixture. At room temperature, 5-10 equivalent of nitromethane is added to the mixture and reacted in an 80° C. oil bath for 10 hours. Then the reaction system is cooled to room temperature and a large amount of solid is precipitated. After filtered, Compound 2a is obtained.

The preparation of Compound 3a: 20 mmol of lithium aluminum hydride is suspended in an appropriate amount of anhydrous tetrahydrofuran and placed in an ice water bath. And a solution of unsaturated nitro-compound (2a) in anhydrous tetrahydrofuran is slowly added dropwise. After the addition is completed, the reaction solution is transferred into an oil bath, refluxed for 3 hours, and then cooled to room temperature. The defined amount of water is added slowly and a clear solution is obtained by filtration. After dried over anhydrous sodium sulfate and evaporated to dryness, an oily Compound 3a is obtained.

The preparation of Compound 5a: 10 mmol of substrate (4a, purchased from Sigma-Aldrich Company) is dissolved in an appropriate amount of anhydrous methanol, and 1.5-3.0 equivalent of ammonium formate is added. 10% palladium carbon is added under stirring and hydrogen is ventilated at the same time. The reaction is carried out at room temperature overnight. After the palladium carbon is removed by filtration, the solution is evaporated to dryness to give an oily Compound 5a.

The preparation of Compound 6a: at room temperature, substrate 3a or 5a is condensed with R5-, R6-, R7-, and R8-substituted phenylacetic acid in the presence of 1-ethyl-3(3-dimethyl-propylamine) carbodiimide or triethylamine, and anhydrous dichloromethane. The product is purified by column chromatography or recrystallized by using ethanol to give Compound 6a with high yield.

The preparation of Compound 7a: under $N_2$, substrate 6a in acetonitrile used as solvent is refluxed under the action of phosphorus oxychloride to obtain Compound 7a with high yield. For compound 7a, further purification is not necessary, the operation is simple and the reaction is quick.

The preparation of Compound 8a: Compound 7a can be reduced by using sodium borohydride to form racemic Compound 8a, if necessary. The chiral reducing reagent, such as catalyst (Noyori, *J. Am. Chem. Soc.* 1996, 118, 4916-4917), N,N-dimethylformamide, triethylamine/formic acid, can also be used to carry out the asymmetric reduction reaction, thereby obtaining Compound 8a with a single configuration.

The preparation of Compound 9a: the intermediate Compound 8a is reacted with aldehyde under acidic condition to obtain Compound 9a with satisfactory yield and selectivity.

The second reaction route:

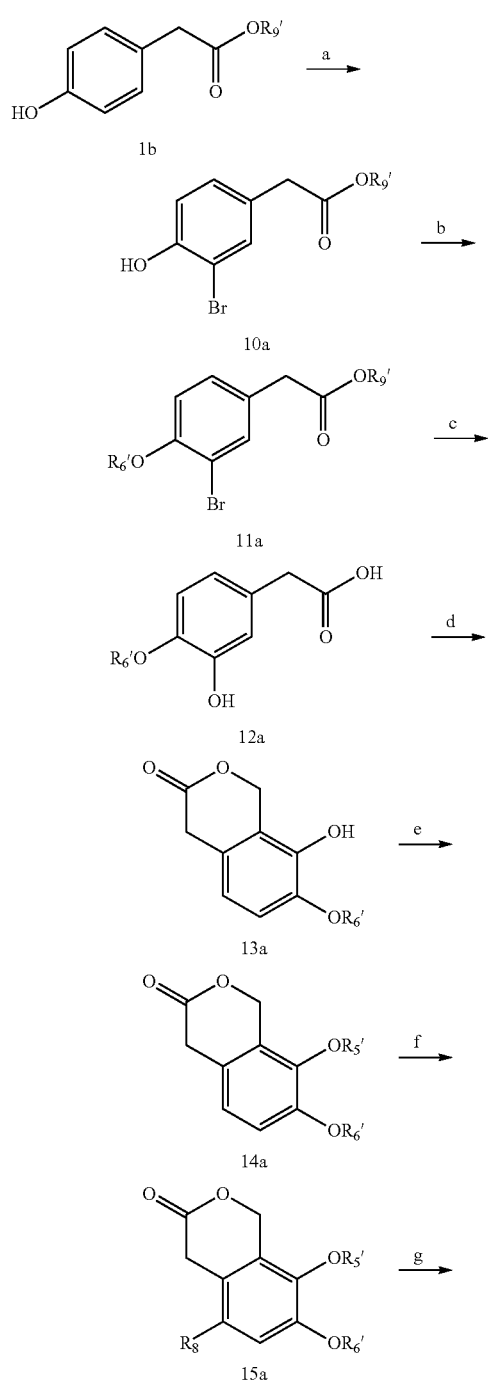

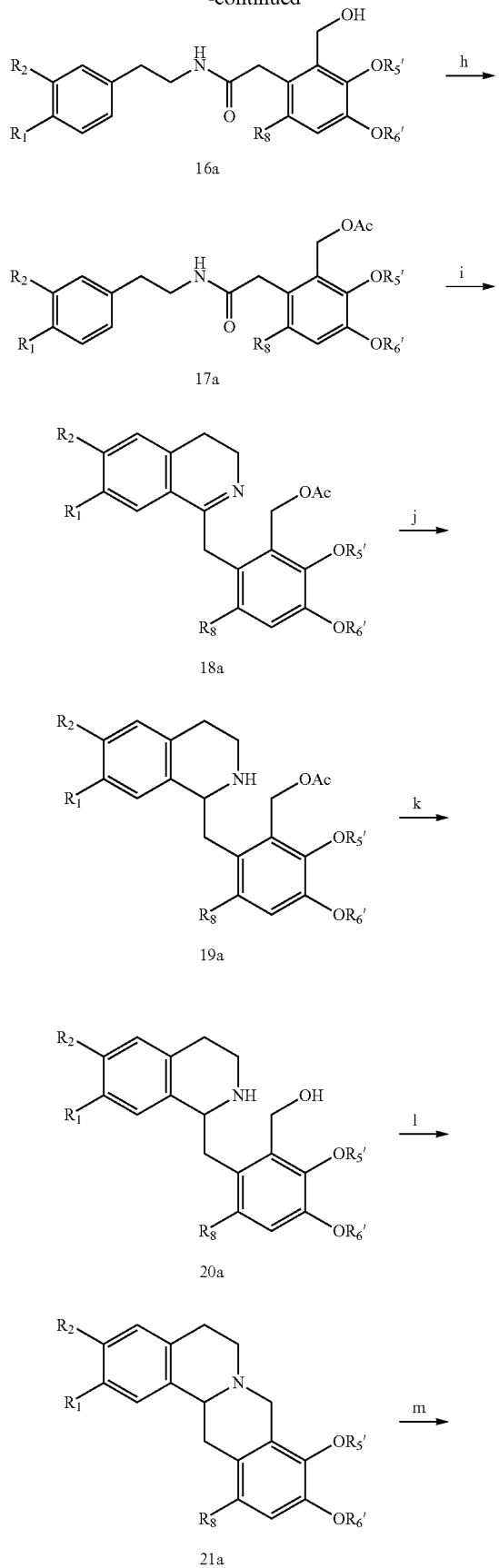

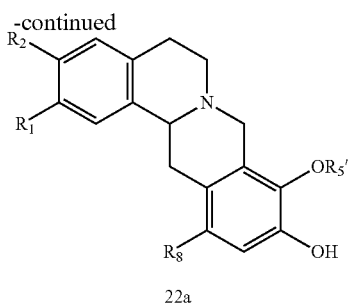

22a

Wherein, R9' is a C1-C6 alkyl, R5' is a halogen-substituted or unsubstituted C1-C6 alkyl, or a substituted or unsubstituted benzyl, R6' is a halogen-substituted or unsubstituted C1-C6 alkyl, or a substituted or unsubstituted benzyl, wherein a substituent for substitution can be a C1-C6 alkyl, a halogen or a C1-C6 alkoxy.

Reaction reagents and conditions: a) room temperature, acetic acid, liquid bromine; b) alkylating reagent/benzylating reagent, solvent, organic alkali/inorganic alkali; c) catalyst containing copper or copper ion, alkaline condition, water, 90° C. to 150° C. of reaction temperature, pH 1-3; d) phenylboronic acid, toluene, paraformaldehyde and water; e) solvent, alkylating reagent/benzylating reagent, organic alkali/inorganic alkali; f) nitrating reagent; g) phenethylamine containing at least one electron-donating substituent, ethanol, reflux; h) solvent, acylating reagent, inorganic/organic alkali; i) solvent, condensing agent; j) sodium borohydride, sodium cyanoborohydride or sodium acetoxy borohydride/catalyst (Noyori), N, N-dimethylbenzamide, triethylamine and formic acid; k) solvent, inorganic alkali; l) solvent, halogenating reagent, organic/inorganic alkali; m) reflux, concentrated hydrochloric acid, ethanol/BCl$_3$, dichloromethane.

The preparation method according to the second reaction route is described in detail as follows.

The preparation of Compound 10a: at room temperature, Compound 1b (purchased from Accela ChemBio Co., Ltd.) is reacted with liquid bromine. The reaction is finished in 1 to 2 hours. The product is poorly dissolved in acetic acid. The post-processing is simple so that pure product Compound 10a can be obtained conveniently.

The preparation of Compound 11a: in an appropriate solvent, Compound 10a is reacted with an alkylating reagent (such as dimethyl sulfate, methyl iodide, diazomethane, methyl trifluoromethanesulfonate or other alkylating reagent) or a benzylating reagent (such as substituted benzyl chloride, benzyl bromide or other benzylating reagent) under the action of organic/inorganic alkali to obtain Compound 11a. Said solvent is selected from the following group: methanol, ethanol, acetone, N, N-dimethylformamide, dimethyl sulfoxide, tetrahydrofuran, dichloromethane, chloroform, dioxane, preferably, acetone, tetrahydrofuran, and N, N-dimethyl formamide. Said inorganic alkali is selected from the following group: sodium hydroxide, potassium hydroxide, cesium hydroxide, barium hydroxide, potassium hydride, sodium hydride, sodium tert-butoxide, potassium tert-butoxide, potassium carbonate, sodium carbonate and calcium carbonate. Said organic alkali is selected from triethylamine, diisopropylethylamine, pyridine, N, N-dimethylaniline, N, N-dimethyl-pyridine. The benzyl chloride, benzyl bromide, methyl iodide, dimethyl sulfate and potassium carbonate are preferable.

The preparation of Compound 12a: a catalyst used in the reaction is relatively inexpensive and can be one or two of the following: copper sulfate, copper oxide, copper powder, copper chloride, copper bromide, copper iodide, copper carbonate, copper nitrate, copper hydroxide and the like, preferably, one or the combination of two of copper sulfate, copper oxide, and copper powder. The reaction is conducted in the presence of alkali, such as sodium hydroxide, potassium hydroxide, cesium hydroxide, calcium hydroxide, barium hydroxide or quaternary ammonium hydroxide, preferably, sodium hydroxide, potassium hydroxide, or cesium hydroxide. The reaction can be (but not necessarily) finished with the help of microwave. The reaction temperature is between 90° C. and 150° C. The method is very effective for preparing phenolic hydroxyl group. Relatively pure Compound 12a can be obtained by adjusting the pH value of reaction mixture to 1-3 after the reaction is finished. If further purification is necessary, recrystallization can be carried out by using one or mixed solvent of two of the following solvents: ethyl acetate, n-hexane, benzene, toluene, petroleum ether, ethanol, isopropyl alcohol, methanol, chloroform, xylene, preferably, benzene, toluene, xylene.

The preparation of Compound 13a: referring to Richard J. Spangler, Brian G. Beckmann, Jong Ho Kim. *J. org. chem.*, 1977, 42, 2989-2996. Mark Cushman, Frederick W. Dekow. *J. org. chem.*, 1979, 44, 407-409. 2.0-3.0 equivalent of phenylboronic acid is refluxed in toluene for 1 hour, and then paraformaldehyde is added and reacted in toluene at the temperature of 100° C. for 46 hours. The solvent is evaporated and the reaction is conducted in water for 2 hours. Then the reaction mixture is extracted with dichloromethane. Then the extract liquid is dried over sodium sulfate and the solvent is evaporated. After stirred in diethyl ether for 3 hours, Compound 13a is obtained by filteration.

The preparation of Compound 14a: in an appropriate solvent, Compound 13a is reacted with an alkylating reagent (such as dimethyl sulfate, methyl iodide, diazomethane, methyl trifluoromethanesulfonate or other alkylating reagent), an acylating reagent (acetyl chloride, acetic anhydride, benzoyl chloride, trifluoroacetic acid anhydride) or a benzylating reagent (such as substituted benzyl chloride, benzyl bromide or other benzylating reagent) under the action of organic/inorganic alkali to obtain Compound 14a. Said solvent is selected from the following group: methanol, ethanol, acetone, N, N-dimethylformamide, dimethyl sulfoxide, tetrahydrofuran, dichloromethane, chloroform, dioxane, preferably, acetone, tetrahydrofuran, and N, N-dimethyl formamide. Said inorganic alkali is selected from the following group: sodium hydroxide, potassium hydroxide, cesium hydroxide, barium hydroxide, potassium hydride, sodium hydride, sodium tert-butoxide, potassium tert-butoxide, potassium carbonate, sodium carbonate and calcium carbonate. Said organic alkali is selected from triethylamine, diisopropylethylamine, pyridine, N,N-dimethylaniline, N,N-dimethyl-pyridine. The benzyl chloride, benzyl bromide, methyl iodide, dimethyl sulfate and potassium carbonate, acetyl chloride, and acetic anhydride are preferable.

The preparation of Compound 15a: under the action of conventional nitrating reagent, Compound 15a (nitration product) is obtained from Compound 14a. The reaction temperature is between 0° C. and 25° C., and the reaction time is 10 minutes to 12 hours. Said nitrating reagent can be a mixture of concentrated sulfuric acid and nitric acid, a mixture of nitric acid, concentrated sulfuric acid and sodium nitrate, a mixture of concentrated sulfuric acid and potassium nitrate, a mixture of concentrated sulfuric acid and sodium nitrite, a mixture of acetic acid and concentrated nitric acid and the like, with the mixture of acetic acid and concentrated nitric acid being preferred. The mixing ratio is not particularly limited.

The preparation of Compound 16a: referring to Mark Cushman, Frederick W. Dekow. *J. org. chem.*, 1979, 44, 407-409. 10 mmol of Compound 15a with the same equivalent of amine are added to an appropriate amount of ethanol and refluxed overnight. The solvent is evaporated, and the crude product is recrystallized by using a suitable solvent. The solvent for recrystallization is selected from one or two of the followings: ethyl acetate, n-hexane, benzene, toluene, petroleum ether, ethanol, isopropanol, methanol, chloroform, and xylene, preferably, toluene, xylene and ethanol.

The preparation of Compound 17a: 6 mmol of Compound 16a is dissolved in 20 mL of suitable solvent and 9 mmol of organic/inorganic alkali is added. 9 mmol of acylating agent is slowly added at 0° C. Then the reaction is performed at room temperature for one hour and appropriate amount of water is added. The reaction mixture is extracted for three times with dichloromethane and dichloromethane layer is washed with saturated saline solution. The extract liquid is dried over sodium sulfate to and evaporated to dryness, thereby obtaining Compound 17a. Compound 17a can be directly used in the next reaction without further purification. Said acylating agent can be, such as acetic anhydride, acetyl chloride, trifluoroacetic anhydride, trichloroacetic anhydride, methyl chloroformate, ethyl chloroformate, etc. Said organic alkali can be, such as triethylamine, diisopropyl ethylamine, pyridine, N, N-dimethylaniline, N, N-dimethyl pyridine, etc. And said inorganic alkali can be, such as potassium carbonate, sodium carbonate, sodium bicarbonate, potassium bicarbonate, sodium hydroxide and potassium hydroxide etc. Preferably, said acylating agent is acetic anhydride, acetyl chloride, said organic base is triethylamine, pyridine, diisopropylethylamine, and said solvent is dichloromethane, tetrahydrofuran, diethyl ether, toluene etc.

The preparation of Compound 18a: 5 mmol of Compound 17a is dissolved in an appropriate amount of suitable solvent and heated to reflux. 30 mmol of condensing reagent is added to the reaction solution. The reaction is monitored by TLC. Most of solvent is evaporated, and the reaction solution is neutralized with saturated sodium bicarbonate, extracted for three times with dichloromethane, dried over sodium sulfate and evaporated to dryness. The product is directly used in the next reaction without further purification. The suitable solvent can be anhydrous acetonitrile, anhydrous toluene, benzene and the like, and the condensing reagent can be phosphorus oxychloride, phosphorus oxybromide, phosphorus pentoxide and the like, wherein said condensing reagent is preferably phosphorus oxychloride, and said solvent is preferably anhydrous acetonitrile.

The preparation of Compound 19a: The imine Compound 18a obtained above is asymmetrically reduced by using Noyori catalyst in anhydrous N,N-dimethylformamide in the presence of triethylamine and formic acid to obtain chiral amine 19a. The reaction is carried out at room temperature for 7 to 12 hours. After the reaction is finished, the reaction solution is neutralized with saturated aqueous sodium bicarbonate solution, extracted with ethyl acetate, and dried over sodium sulfate. In addition, the achirality reduction can also be conducted by using sodium borohydride, sodium cyanoborohydride or sodium acetoxy borohydride.

The preparation of Compound 20a: 3 mmoL of Compound 19a is dissolved in a suitable solvent and an appropriate amount of inorganic alkali is added to the above solution. The reaction is conducted at room temperature for 3 hours and solid precipitates. The precipitate is filtered and dried, thereby obtaining the target Compound 20a. Said inorganic alkali can be sodium hydroxide, potassium hydroxide, cesium hydroxide or potassium carbonate, and the like, preferably, sodium hydroxide. The solvent may be a mixture of water and one of ethanol, methanol, N, N-dimethylformamide, preferably, a mixture of water and ethanol or methanol.

The preparation of Compound 21a: in a suitable solvent, Compound 20a can be halogenated with a halogenating agent under alkaline condition, and then the product 21a is obtained through ring-closing reaction. Said halogenating agent is thionyl chloride, thionyl bromide, phosphorus trichloride, phosphorus tribromide, phosphorus pentachloride, phosphorus pentabromide, and the like. The solvent is dichloromethane, tetrahydrofuran, diethyl ether, chloroform and the like. Said alkali is an organic alkali or an inorganic alkali, wherein the organic alkali is preferably triethylamine, pyridine, diisopropylethylamine, and the inorganic alkali is preferably potassium carbonate, sodium carbonate, sodium bicarbonate, potassium bicarbonate, sodium hydroxide, potassium hydroxide, calcium carbonate, ammonia, etc.

The preparation of Compound 22a: Compound 21a is dissolved in ethanol and concentrated hydrochloric acid is added to reflux or $BCl_3$ and dichloromethane is added to reflux at low temperature in order to remove R6' protective group for giving Compound 22a. Preferably, ethanol or concentrated hydrochloric acid is used to remove R6' protective group.

Further, the inventors have found that the compound of general formula (I) has excellent $D_1$ receptor selectivity and 5-HT receptor activity through experiments. The compounds of the invention can be used for the preparation of medicament used in experiment model relating to dopamine receptor and 5-HT receptor or for the preparation of medicament for treating and preventing the diseases relating to dopamine receptor and 5-HT receptor.

The invention also provides a pharmaceutical composition which comprises a therapeutically effective amount of the compound of general formula (I), enantiomer, diastereomer, racemate and mixtures thereof, or a pharmaceutically acceptable salt thereof and one or more pharmaceutically acceptable carriers. The pharmaceutical composition may further include conventional additives, such as odorant, flavoring agent and so on.

The pharmaceutical composition provided in the invention contains preferably 1-99% of the compound of general formula (I) by weight as active ingredient. Preferably, the compound of general formula (I) as active ingredient is 65%~99% of pharmaceutical composition based on the total weight of pharmaceutical composition, and the remainders are the pharmaceutically acceptable carriers and/or conventional additives.

The compound and pharmaceutical composition provided in the invention can be various forms, such as tablet, capsule, powder, syrup, solution, suspension, aerosol etc., and may be present in a suitable solid or liquid carrier or diluent and suitable disinfector for injection or instillation.

The various dosage forms of pharmaceutical composition of the present invention can be prepared according to conventional methods in pharmaceutical field. The unit dose of formulation contains 0.05-200 mg of the compound of general formula (I), preferably 0.1 mg-100 mg of the compound of general formula (I).

The compound and pharmaceutical composition of the invention can be used clinically in mammal including humans and animals, and can be delivered through mouth, nose, skin, lung, or gastrointestinal tract and other routes. The most preferable administration route is oral. Most preferable daily dose is 0.01-200 mg/kg body weight for once administration, or 0.01-100 mg/kg body weight in divided doses. Regardless of administration method, the optimal dose for individual should be established based on specific therapeutic regime. Usually start from small dose and gradually increase the dose until the most suitable dose is found.

DETAILED DESCRIPTION

Figure 1:
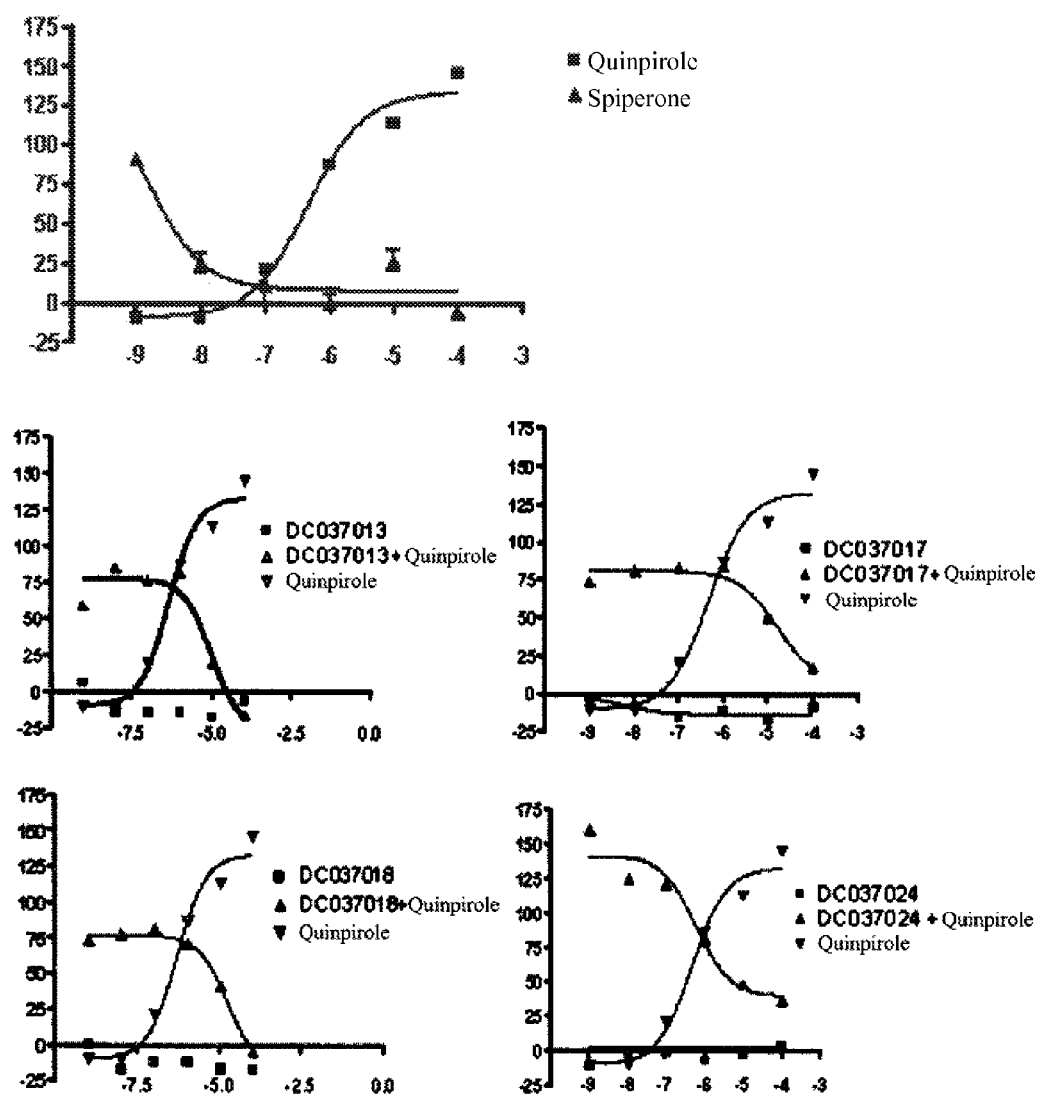
FIG. 1 is a curve graph of functional assay of part of the test compounds on D-$_2$ receptor.

The present invention will be further illustrated in the following examples. These examples are intended to illustrate the invention, but not limit the invention in any way. All parameters of the examples as well as the rest of the description are described based on the weight unless otherwise indicated.

Example 1

S-(−)-2-hydroxy-3,9,12-trimethoxy-5,8,13,13a-tetrahydro-6H-dibenzo[a,g]quinolizine (DC037030) (prepared according to the first reaction route)

1.1 Preparation of 3-methoxy-4-benzyloxy-ω-nitrostyrolene (Compound 2)

The preparation was conducted with reference to *org. Lett.*, 2008, 8(8), 1525-1528. Firstly, the hydroxyl of vanillin (purchased from Alfa Aesar company) was protected with benzyl. And then protected vanillin and nitromethane were refluxed in ammonium acetate and acetic acid to obtain the target product. Two-step yield: 75%; melting point: 117-118° C. $^1$H NMR (CDCl$_3$): $^1$H NMR (CDCl$_3$, 300 MHz): δ 7.95 (d, J=13.2 Hz, 1H), 7.51 (d, J=13.2 Hz, 1H), 7.42-7.32 (m, 5H), 7.10 (dd, J=8.4 Hz, J=1.8 Hz, 1H), 7.02 (d, J=1.8 Hz, 1H), 6.92 (d, J=8.4 Hz, 1H), 5.22 (s, 2H), 3.92 (s, 3H); ESI-MS m/z 251 [M+H]$^+$.

1.2 Preparation of 3-methoxy-4-benzyloxyphenylethylamine (Compound 3)

Under N$_2$, lithium aluminum hydride (6.0 g) was suspended in anhydrous tetrahydrofuran (50 mL) Compound 2 (22.5 g) was dissolved in 30 mL of anhydrous tetrahydrofuran and the resulting solution was slowly added into above suspension dropwise. Upon addition, the reaction solution was moved in an oil bath and refluxed for 3 hours. After the reaction was finished, the reaction solution was cooled to room temperature and then the same equivalent of water as excessive lithium aluminum hydride was added to quench the reaction. The precipitate was filtered off and then the filtrate was evaporated to dryness. Yield: 85%. $^1$H NMR (CDCl$_3$, 300 MHz): δ 8.20 (br, 2H), 7.46-7.33 (m, 5H), 6.99 (d, J=8.4, 1 H), 6.92 (d, J=1.5, 1 H), 6.75 (dd, J=8.4, J=1.5, 1 H), 5.06 (s, 2H), 3.79 (s, 3H), 3.01 (t, 2H), 2.85 (m, 2H); ESI-MS m/z 258 [M+H]$^+$.

1.3 Preparation of N-(3'-methoxy-4'-benzyloxyphenylethyl)-2,5-dimethoxy phenylacetamide (Compound 6)

2,5-dimethoxyphenylacetic acid (392 mg, purchased from Sigma Aldrich Company) was dissolved in anhydrous dichloromethane (10 mL) Compound 3 (514 mg), EDCI (573 mg) and triethylamine (433 μL) was added, respectively. The reaction was conducted overnight under N$_2$. After completion of the reaction, the reaction solution was washed with 1 N diluted hydrochloric acid, then the organic phase was washed once with saturated sodium bicarbonate solution and finally washed once with saturated salt solution. After dried over sodium sulfate, the organic phase was evaporated and product 6 was obtained by column chromatography. $^1$H NMR (CDCl$_3$): δ 7.46-7.26 (m, 5H), 6.80-6.51 (m, 5H), 6.49 (d, J=2.1, 1H), 5.83 (m, 1H), 5.14 (s, 2H), 3.75 (s, 3H), 3.74 (s, 3H), 3.73 (s, 3H), 3.65 (s, 2H), 3.47-3.36 (m, 2H), 3.64-3.59 (m, 2H); ESI-MS m/z 436 [M+H]$^+$.

1.4 Preparation of 1-(2',5'-dimethoxyl)benzyl-6-methoxy-7-benzyloxy-3,4-dihydro-isoquinoline (Compound 7)

Under N$_2$, Compound 6 (435 mg) was dissolved in 15 mL of anhydrous acetonitrile and POCl$_3$ (546 μL) was added to above solution. The reaction mixture was refluxed for 30 min and then cooled. The reaction solution was concentrated to give oily liquid. The oily liquid was dissolved in dichloromethane, neutralized with saturated sodium bicarbonate, and extracted three times. The organic phase was washed once with saturated saline solution, dried and eandvaporated to dryness. $^1$H NMR (CDCl$_3$): δ 7.48-7.32 (m, 5H), 7.00 (s, 1H), 6.80-6.68 (m, 4H), 6.6 (s, 1H), 3.99 (s, 2H), 3.82 (s, 3H), 3.80 (s, 3H), 3.70-3.60 (m, 5H), 2.65-2.60 (m, 2H); ESI-MS m/z 418 [M+H]$^+$.

1.5 Preparation of 1-(2',5'-dimethoxyl)benzyl-6-methoxy-7-benzyloxy-1,2,3,4-tetrahydro-isoquinoline (Compound 8)

Compound 7 (418 mg) freshly prepared was dissolved in DMF (5 mL), 1% of (R,R)-Noyori catalyst, a mixed solution of triethylamine and formic acid was added separately and the resulting solution was stirred overnight at room temperature. After the completion of the reaction, the reaction solution was neutralized with saturated sodium bicarbonate, and extracted with ethyl acetate for three times. The organic phase was washed once with saturated saline solution, dried and concentrated. The product can be used in the next reaction without further purification. ESI-MS m/z 420 [M+H]$^+$.

1.6 S-(−)-2-benzyloxy-3,9,12-trimethoxy-5,8,13,13a-tetrahydro-6H-dibenzo[a,g]quinolizine (Compound 9)

Compound 8 (419 mg) was mixed with aqueous formaldehyde and formic acid and stirred to react at 90° C. for 2 hours. After the completion of the reaction, most of liquid was evaporated and the remainder liquid was neutralized with saturated sodium bicarbonate, and extracted with ethyl acetate for three times. The organic phase was washed once with saturated saline solution, dried and evaporated to dryness. And then the produce was purified by column chromatography. $^1$H NMR (CDCl$_3$): δ 7.44-7.34 (m, 5H), 6.73 (s 1H), 6.70 (s, 1H), 6.66 (m, 2H), 5.14 (s, 2H), 4.19 (m, 1H), 3.78 (s, 3H), 3.77 (s, 3H), 3.76 (s, 3H), 3.52-3.30 (m, 3H), 3.21-3.12 (m, 2H), 2.66-2.50 (m, 3H); ESI-MS m/z 432 [M+H]$^+$.

Preparation of S-(−)-2-hydroxy-3,9,12-trimethoxy-5,8,13,13a-tetrahydro-6H-dibenzo[a,g]quinolizine (DC037030)

Compound 8 (300 mg) was dissolved in 5 mL of ethanol and 7 mL of concentrated hydrochloric acid was added with stirring. The reaction was carried out at 90° C. for 1.5 hours. After the completion of the reaction, the reaction solution was cooled to room temperature and most of liquid was evaporated. The remainder liquid was neutralized with aqueous ammonia and the aqueous phase was extracted with dichloromethane for many times until there is no product in aqueous phase. The dichloromethane layer was washed with saturated saline solution, dried and evaporated to dryness. And then the product was purified by column chromatography. $^1$H NMR (CDCl$_3$): δ 6.90 (s, 1H), 6.63 (s, 2H), 6.58 (s, 1H), 4.18-4.13 (m, 1H), 3.86 (s, 3H), 3.78 (s, 3H), 3.77 (s, 3H), 3.49-3.34 (m, 3H), 3.19-3.07 (m, 2H), 2.67-2.49 (m, 3H); ESI-MS m/z 342 [M+H]$^+$.

Example 2

(±)-2,3,10,11-tetramethoxy-5,8,13,13a-tetrahydro-6H-dibenzo[a,g]quinolizine (DC037001)

The preparation method was described in Example 1. $^1$H NMR (CDCl$_3$): δ 6.73 (s, 1H), 6.67 (s, 1H), 6.61 (s, 1H), 6.57 (s, 1H), 3.93 (m, 1H), 3.89 (s, 3H), 3.87 (s, 3H), 3.86 (s, 3H), 3.85 (s, 3H), 3.75-3.59 (m, 2H), 3.28-3.12 (m, 3H). 2.89-2.63 (m, 3H); ESI-MS m/z 356 [M+H]$^+$.

Example 3

(±)-2,3,9,10,11-pentamethoxyl-5,8,13,13a-tetrahydro-6H-dibenzo[a,g]quinolizine (DC037002)

The preparation method was described in Example 1. $^1$H NMR (CDCl$_3$): δ 6.70 (s, 1H), 6.60 (s, 1H), 6.47 (s, 1H), 4.10 (m, 1H), 3.88 (s, 3H), 3.87 (s, 3H), 3.85 (s, 3H), 3.82 (s, 3H), 3.81 (s, 3H), 3.55-3.42 (m, 2H), 3.25-3.12 (m, 3H), 2.85-2.78 (m, 1H), 2.66-2.61 (m, 2H); ESI-MS m/z 386 [M+H]$^+$.

Example 4

(±)-2,3,9,12-tetramethoxy-5,8,13,13a-tetrahydro-6H-dibenzo[a,g]quinolizine (DC037003)

The preparation method was described in Example 1. $^1$H NMR (CDCl$_3$): δ 6.80 (s, 1H), 6.67 (s, 1H), 6.65 (s, 1H), 6.61 (s, 1H), 4.18 (m, 1H), 3.91 (s, 3H), 3.87 (s, 3H), 3.80 (s, 6H), 3.52-3.37 (m, 3H), 3.21-3.19 (m, 2H). 2.69-2.62 (m, 3H); ESI-MS m/z 356 [M+H]$^+$.

Example 5

(8S,14S)-2,3,10,11-tetramethoxy-8-methyl-5,8,13,13a-tetrahydro-6H-dibenzo[a,g]quinolizine (DC037004)

Compound DC037004 was prepared according to Example 1 except for reacting 686 mg of 1-(3,4-bimethoxy)benzyl-6,7-bimethoxy-1,2,3,4-bihydroisoquinoline, acetaldehyde (10 mL) and formic acid (15 mL) at 90° C. for 2 hours. $^1$H NMR (CDCl$_3$): δ 6.73 (s, 1H), 6.67 (s, 1H), 6.61 (s, 1H), 6.57 (s, 1H), 4.12-4.06 (m, 2H), 3.93 (s, 3H), 3.91 (s, 3H), 3.89 (s, 3H), 3.87 (s, 3H), 3.75-3.62 (m, 2H), 3.28-3.14 (m, 2H), 2.89-2.68 (m, 2H); ESI-MS m/z 370 [M+H]$^+$.

Example 6

(8R,14S)-2,3,10,11-tetramethoxy-8-methyl-5,8,13,13a-tetrahydro-6H-dibenzo[a,g]quinolizine (DC037005)

The preparation method was described in Example 5. $^1$H NMR (CDCl$_3$): δ 6.73 (s, 1H), 6.67 (s, 1H), 6.61 (s, 1H), 6.57 (s, 1H), 4.12-4.06 (m, 2H), 3.93 (s, 3H), 3.91 (s, 3H), 3.89 (s, 3H), 3.87 (s, 3H), 3.75-3.62 (m, 2H), 3.28-3.14 (m, 2H), 2.89-2.68 (m, 2H); ESI-MS m/z 370 [M+H]$^+$.

Example 7

S-(−)-2,3,9,10,11-pentamethoxyl-5,8,13,13a-tetrahydro-6H-dibenzo[a,g]quinolizine (DC037006)

The preparation method was described in Example 1. $^1$H NMR (CDCl$_3$): δ 6.70 (s, 1H), 6.60 (s, 1H), 6.47 (s, 1H), 4.10 (m, 1H), 3.88 (s, 3H), 3.87 (s, 3H), 3.85 (s, 3H), 3.82 (s, 3H), 3.81 (s, 3H), 3.55-3.42 (m, 2H), 3.25-3.12 (m, 3H), 2.85-2.78 (m, 1H), 2.66-2.61 (m, 2H); ESI-MS m/z 386 [M+H]$^+$.

Example 8

(±)-3,9,10,11-tetramethoxy-5,8,13,13a-tetrahydro-6H-dibenzo[a,g]quinolizine (DC037007)

The preparation method was described in Example 1. $^1$H NMR (CDCl$_3$): δ 7.16 (d, J=8.4, 1H), 6.79 (m, 1H), 6.67 (s, 2H), 6.58 (s, 1H), 3.95 (m, 1H), 3.83 (s, 6H), 3.80 (s, 3H), 3.64-3.56 (m, 2H), 3.32-3.13 (m, 3H). 2.85-2.63 (m, 3H); ESI-MS m/z 356 [M+H]$^+$.

Example 9

S-(−)-2,3,9,12-tetramethoxy-5,8,13,13a-tetrahydro-6H-dibenzo[a,g]quinolizine (DC037008)

The preparation method was described in Example 1. $^1$H NMR (CDCl$_3$): δ 7.09 (d, J=8.4, 1H), 6.97 (s, 1H), 6.72 (d, J=8.4, 1H), 6.51 (s, 1H), 4.18 (m, 1H), 3.87 (s, 3H), 3.84 (s, 3H), 3.83 (s, 3H), 3.82 (s, 3H), 3.52-3.37 (m, 3H), 3.21-3.19 (m, 2H), 2.69-2.62 (m, 3H); ESI-MS m/z 356 [M+H]$^+$.

Example 10

(±)-3,10,11-trimethoxy-5,8,13,13a-tetrahydro-6H-dibenzo[a,g]quinolizine (DC037009)

The preparation method was described in Example 1. $^1$H NMR (CDCl$_3$): δ 7.16 (d, J=8.4, 1H), 6.79 (m, 1H), 6.67 (s, 2H), 6.58 (s, 1H), 3.95 (m, 1H), 3.83 (s, 6H), 3.80 (s, 3H), 3.64-3.56 (m, 2H), 3.32-3.13 (m, 3H), 2.85-2.63 (m, 3H); ESI-MS m/z 326 [M+H]$^+$.

Example 11

S-(+3,10,11-trimethoxy-5,8,13,13a-tetrahydro-6H-dibenzo[a,g]quinolizine (DC037010)

The preparation method was described in Example 1. $^1$H NMR (CDCl$_3$): δ 7.18 (d, J=9.0, 1H), 6.78 (m, 1H), 6.66 (s, 2H), 6.57 (s, 1H), 3.94 (m, 1H), 3.83 (s, 6H), 3.80 (s, 3H), 3.65-3.58 (m, 2H), 3.30-3.12 (m, 3H), 2.86-2.62 (m, 3H); ESI-MS m/z 326 [M+H]$^+$.

Example 12

S-(−)-2,3-bimethoxy-10,11-methylenedioxy-5,8,13,13a-tetrahydro-6H-dibenzo[a,g]quinolizine (DC037011)

The preparation method was described in Example 1. $^1$H NMR (CDCl$_3$): δ 6.72 (s, 1H), 6.63 (m, 1H), 6.61 (s, 1H), 6.55

(s, 1H), 5.90 (s, 2H), 3.94 (m, 1H), 3.89 (s, 3H), 3.87 (s, 3H), 3.67-3.55 (m, 2H), 3.25-3.11 (m, 3H), 2.70-2.60 (m, 3H); ESI-MS m/z 340 [M+H]$^+$.

Example 13

S-(−)-2,3,10,11-bimethylenedioxy-5,8,13,13a-tetrahydro-6H-dibenzo[a,g]quinolizine (DC037012)

The preparation method was described in Example 1. $^1$H NMR (CDCl$_3$): δ 6.72 (s, 1H), 6.60 (m, 1H), 6.58 (s, 2H), 6.53 (s, 1H), 5.91 (s, 2H), 5.90 (s, 2H), 3.92-3.87 (m, 1H), 3.65-3.51 (m, 2H), 3.19-3.10 (m, 3H), 2.83-2.59 (m, 3H); ESI-MS m/z 324 [M+H]$^+$.

Example 14

S-(−)-2,3-methylenedioxy-9,12-bimethoxy-5,8,13,13a-tetrahydro-6H-dibenzo[a,g]quinolizine (DC037013)

The preparation method was described in Example 1. $^1$H NMR (CDCl$_3$): δ 6.81 (s, 1H), 6.65 (s, 2H), 6.59 (s, 2H), 5.91 (s, 2H), 4.17 (m, 1H), 3.78 (s, 3H), 3.77 (s, 3H), to 3.51-3.32 (m, 3H), 3.20-3.13 (m, 2H), 2.68-2.50 (m, 3H); ESI-MS m/z 340 [M+H]$^+$.

Example 15

(±)-2,3-bimethoxy-10,11-methylenedioxy-5,8,13,13a-tetrahydro-6H-dibenzo[a,g]quinolizine (DC037014)

The preparation method was described in Example 1. $^1$H NMR (CDCl$_3$): δ 6.73 (s, 1H), 6.63 (m, 1H), 6.58 (s, 1H), 6.56 (s, 1H), 5.91 (s, 2H), 3.92-3.89 (m, 1H), 3.84 (s, 3H), 3.83 (s, 3H), 3.63-3.51 (m, 2H), 3.20-3.09 (m, 3H), 2.82-2.76 (m, 1H), 2.66-2.57 (m, 2H); ESI-MS m/z 340 [M+H]$^+$.

Example 16

S-(−)-2,3-methylenedioxy-10,11-bimethoxy-5,8,13,13a-tetrahydro-6H-dibenzo[a,g]quinolizine (DC037015)

The preparation method was described in Example 1. $^1$H NMR (CDCl$_3$): δ 6.72 (s, 1H), 6.63 (m, 1H), 6.58 (s, 1H), 6.56 (s, 1H), 5.90 (s, 2H), 3.92 (m, 1H), 3.84 (s, 3H), 3.83 (s, 3H), 3.68-3.52 (m, 2H), 3.21-3.07 (m, 3H), 2.84-2.75 (m, 1H), 2.66-2.57 (m, 2H); ESI-MS m/z 340 [M+H]$^+$.

Example 17

S-(−)-2,3-methylenedioxy-9,10,11-bimethoxy-5,8,13,13a-tetra-hydro-6H-dibenzo[a,g]quinolizine (DC037016)

The preparation method was described in Example 1. $^1$H NMR (CDCl$_3$): δ 6.72 (s, 1H), 6.63 (m, 1H), 6.56 (s, 1H), 5.90 (s, 2H), 3.93-3.90 (m, 1H), 3.86 (s, 3H), 3.85 (s, 3H), 3.83 (s, 3H), 3.68-3.58 (m, 2H), 3.24-3.07 (m, 3H), 2.85-2.77 (m, 1H), 2.66-2.54 (m, 2H); ESI-MS m/z 370 [M+H]$^+$.

Example 18

S-(−)-2,3-bimethoxy-9,11-dimethyl-5,8,13,13a-tetrahydro-6H-dibenzo[a,g]quinolizine (DC037017)

The preparation method was described in Example 1. $^1$H NMR (CDCl$_3$): δ 7.09 (s, 1H), 6.97 (s, 1H), 6.72 (s, 1H), 6.51 (s, 1H), 4.18-4.02 (m, 1H), 3.87 (s, 3H), 3.85 (s, 3H), 3.51-3.38 (m, 3H), 3.22-3.10 (m, 2H), 2.69-2.54 (m, 3H), 2.36 (s, 3H), 2.34 (s, 3H); ESI-MS m/z 308 [M+H]$^+$.

Example 19

(±)-2,3-bimethoxy-9,11-dimethyl-5,8,13,13a-tetrahydro-6H-dibenzo[a,g]quinolizine (DC037018)

The preparation method was described in Example 5. $^1$H NMR (CDCl$_3$): δ 7.09 (s, 1H), 6.97 (s, 1H), 6.72 (s, 1H), 6.51 (s, 1H), 4.18-4.02 (m, 1H), 3.87 (s, 3H), 3.85 (s, 3H), 3.51-3.38 (m, 3H), 3.22-3.10 (m, 2H), 2.69-2.54 (m, 3H), 2.36 (s, 3H), 2.34 (s, 3H); ESI-MS m/z 324 [M+H]$^+$.

Example 20

(8S,14S)-2,3,9,10,11-pentamethoxyl-8-methyl-5,8,13,13a-tetra-hydro-6H-dibenzo[a,g]quinolizine (DC037019)

The preparation method was described in Example 5. $^1$H NMR (CDCl$_3$): δ 6.73 (s, 1H), 6.67 (s, 1H), 6.52 (s, 1H), 4.12-4.06 (m, 2H), 3.90 (s, 3H), 3.89 (s, 3H), 3.87 (s, 3H), 3.86 (s, 3H), 3.85 (s, 3H), 3.69-3.58 (m, 2H), 3.28-3.14 (m, 2H), 2.89-2.68 (m, 2H); ESI-MS m/z 400 [M+H]$^+$.

Example 21

(8S,14S)-2,3-bimethoxy-8-methyl-10,11-methylenedioxy-5,8,13,13a-tetrahydro-6H-dibenzo[a,g]quinolizine (DC037020)

The preparation method was described in Example 1. $^1$H NMR (CDCl$_3$): δ 6.66 (s, 1H), 6.61 (m, 1H), 6.56 (s, 1H), 6.55 (s, 1H), 5.91 (s, 2H), 4.37-4.24 (m, 1H), 3.87 (s, 3H), 3.85 (s, 3H), 3.15-2.79 (m, 7H), 1.45 (d, J=7.2, 3H); ESI-MS m/z 354 [M+H]$^+$.

Example 22

(±)-2,3-methylenedioxy-10,11-bimethoxy-5,8,13,13a-tetrahydro-6H-dibenzo[a,g]quinolizine (DC037021)

The preparation method was described in Example 1. $^1$H NMR (CDCl$_3$): δ 6.73 (s, 1H), 6.64 (m, 1H), 6.59 (s, 1H), 6.57 (s, 1H), 5.92 (s, 2H), 3.96-3.91 (m, 1H), 3.86 (s, 3H), 3.85 (s, 3H), 3.69-354 (m, 2H), 3.23-3.08 (m, 3H), 2.86-2.77 (m, 1H), 2.67-2.56 (m, 2H); ESI-MS m/z 340 [M+H]$^+$.

Example 23

(±)-2,3-bimethoxy-10,11-bihydroxy-5,8,13,13a-tetrahydro-6H-dibenzo[a,g]quinolizine (DC037022)

The preparation method was described in Example 5. $^1$H NMR (CDCl$_3$): δ 6.70 (s, 1H), 6.69 (m, 1H), 6.53 (s, 1H), 6.44 (s, 1H), 5.92 (s, 2H), 4.24-4.20 (m, 1H), 3.84 (s, 3H), 3.82 (s, 3H), 3.40-337 (m, 1H), 3.16-3.10 (m, 1H), 3.01-2.70 (m, 1H), 2.67-2.56 (m, 2H); ESI-MS m/z 328 [M+H]$^+$.

Example 24

(±)-2,3-bimethoxy-8-methyl-10,11-bihydroxy-5,8,13,13a-tetrahydro-6H-dibenzo[a,g]quinolizine (DC037023)

The preparation method was described in Example 1. $^1$H NMR (CDCl$_3$): δ 6.89 (s, 1H), 6.67 (s, 1H), 6.58 (s, 1H), 6.53

(s, 1H), 4.26-4.05 (m, 1H), 3.79 (s, 3H), 3.76 (s, 3H), 3.73-3.67 (m, 1H), 3.09-2.62 (m, 6H), 1.34 (d, J=6.6, 2H); ESI-MS m/z 342 [M+H]$^+$.

Example 25

(±)-2,3-bihydroxy-10,11-bimethoxy-5,8,13,13a-tetrahydro-6H-dibenzo[a,g]quinolizine (DC037024)

The preparation method was described in Example 5. $^1$H NMR (CDCl$_3$): δ 7.04 (s, 1H), 6.95 (s, 1H), 6.76 (s, 1H), 6.53 (s, 1H), 4.18-4.06 (m, 1H), 3.85 (s, 3H), 3.84 (s, 3H), 3.51-3.36 (m, 3H), 3.21-3.19 (m, 2H), 2.69-2.62 (m, 3H); ESI-MS m/z 328 [M+H]$^+$.

Example 26

(8S,14S)-2,3-bihydroxy-8-methyl-10,11-bimethoxy-5,8,13,13a-tetrahydro-6H-dibenzo[a,g]quinolizine (DC037025)

The preparation method was described in Example 5. $^1$H NMR (CDCl$_3$): δ 6.55 (s, 1H), 6.53 (s, 1H), 6.48 (s, 1H), 6.44 (s, 1H), 4.55-4.48 (m, 1H), 3.84 (s, 3H), 3.82 (s, 3H), 3.30-3.05 (m, 4H), 2.93-2.86 (m, 2H), 1.62 (d, J=6.8, 2H); ESI-MS m/z 342 [M+H]$^+$.

Example 27

(8R,14R)-2,3-bihydroxy-8-methyl-10,11-bimethoxy-5,8,13,13a-tetrahydro-6H-dibenzo[a,g]quinolizine (DC037026)

The preparation method was described in Example 1. $^1$H NMR (CDCl$_3$): δ 6.55 (s, 1H), 6.53 (s, 1H), 6.48 (s, 1H), 6.44 (s, 1H), 4.55-4.48 (m, 1H), 3.84 (s, 3H), 3.82 (s, 3H), 3.30-3.05 (m, 4H), 2.93-2.86 (m, 2H), 1.62 (d, J=6.8, 2H); ESI-MS m/z 342 [M+H]$^+$.

Example 28

(±)-2,3-bihydroxy-9,10,11-trimethoxy-5,8,13,13a-tetrahydro-6H-dibenzo[a,g]quinolizine (DC037027)

The preparation method was described in Example 5. $^1$H NMR (CDCl$_3$): δ 6.95 (s, 1H), 6.76 (d, J=8.4, 1H), 6.51 (s, 1H), 4.18-4.06 (m, 1H), 3.85 (s, 3H), 3.84 (s, 3H), 3.51-3.36 (m, 3H), 3.21-3.19 (m, 2H), 2.69-2.62 (m, 3H); ESI-MS m/z 328 [M+H]$^+$.

Example 29

(±)-2,3-bihydroxy-8-methyl-9,10,11-trimethoxy-5,8,13,13a-tetrahydro-6H-dibenzo[a,g]quinolizine (DC037028)

The preparation method was described in Example 1. $^1$H NMR (CDCl$_3$): δ 6.50 (s, 1H), 6.45 (s, 1H), 6.35 (s, 1H), 4.61-4.37 (m, 2H), 3.93 (s, 3H), 3.87 (s, 6H), 3.49-3.39 (m, 1H), 3.18-2.84 (m, 5H), 1.52 (d, J=6.0, 2H); ESI-MS m/z 342 [M+H]$^+$.

Example 30

S-(−)-2-hydroxy-3-methoxy-10,12-methylenedioxy-5,8,13,13a-tetrahydro-6H-dibenzo[a,g]quinolizine (DC037029)

The preparation method was described in Example 1. $^1$H NMR (CDCl$_3$): δ 6.81 (s, 1H), 6.61 (s, 1H), 6.59 (s, 1H), 6.54 (s, 1H), 5.90 (s, 2H), 3.92-3.87 (m, 1H), 3.87 (s, 3H), 3.65-3.48 (m, 2H), 3.23-3.09 (m, 3H), 2.83-2.55 (m, 3H); ESI-MS m/z 326 [M+H]$^+$.

Example 31

S-(−)-2-hydroxy-3-methoxy-9,11-dimethyl-5,8,13,13a-tetra-hydro-6H-dibenzo[a,g]quinolizine (DC037031)

The preparation method was described in Example 1. $^1$H NMR (CDCl$_3$): δ 6.83 (s, 2H), 6.82 (s, 2H), 6.60 (s, 1H), 4.07-4.00 (m, 1H), 3.85 (s, 3H), 3.59-3.47 (m, 2H), 3.26-3.18 (m, 2H), 2.93-2.89 (m, 1H), 2.70-2.63 (m, 2H), 2.28 (s, 3H), 2.20 (s, 3H); ESI-MS m/z 310 [M+H]$^+$.

Example 32

2,3-bimethylenedioxy-9,12-bimethoxy-5,8,13,13a-tetrahydro-6H-dibenzo[a,g]quinolizine (DC037032)

The preparation method was described in Example 1. $^1$H NMR (CDCl$_3$): δ 6.94 (s, 1H), 6.89 (s, 1H), 6.67 (d, J=8.4, 1H), 6.65 (d, J=8.4, 1H), 5.92 (s, 2H), 4.12-4.06 (m, 1H), 3.88 (s, 3H), 3.84 (s, 3H), 3.54-3.47 (m, 2H), 3.31-3.20 (m, 3H), 2.86-2.78 (m, 1H), 2.65-2.56 (m, 2H); ESI-MS m/z 354 [M+H]$^+$.

Example 33

S-(−)-2,3-methylenedioxy-9,12-dimethyl-5,8,13,13a-tetrahydro-6H-dibenzo[a,g]quinolizine (DC037033)

The preparation method was described in Example 1. $^1$H NMR (CDCl$_3$): δ 6.91 (d, J=8.4, 1H), 6.87 (d, J=8.4, 1H), 6.65 (s, 1H), 6.63 (s, 1H), 5.90 (s, 2H), 4.17-4.06 (m, 1H), 3.82 (s, 3H), 3.80 (s, 3H), 3.51-3.32 (m, 3H), 3.20-3.13 (m, 2H), 2.68-2.50 (m, 3H), 2.37 (s, 3H), 2.34 (s 3H); ESI-MS m/z 340 [M+H]$^+$.

Example 34

S-(+9,12-bimethoxy-2,3,5,8,13,13a-hexahydro-8H-benzo[3,2,a,g]furanquinolizine (DC037034)

The preparation method was described in Example 1. $^1$H NMR (CDCl$_3$): δ 7.11 (s, 1H), 7.01 (s, 1H), 6.65 (d, J=8.1, 1H), 6.58 (d, J=8.1, 1H), 4.31 (m, 2H), 4.16-4.08 (m, 1H), 3.85 (s, 3H), 3.83 (s, 3H), 3.53-3.34 (m, 2H), 3.20-3.02 (m, 4H), 2.79-2.50 (m, 4H); ESI-MS m/z 338 [M+H]$^+$.

Example 35

S-(−)-2,3-bihydroxy-9,12-bimethoxy-5,8,13,13a-tetrahydro-6H-dibenzo[a,g]quinolizine (DC037035)

The preparation method was described in Example 1. $^1$H NMR (CDCl$_3$): δ 7.04 (d, J=8.4, 1H), 6.95 (s, 1H), 6.76 (d, J=8.4, 1H), 6.53 (s, 1H), 4.18-4.06 (m, 1H), 3.85 (s, 3H), 3.84 (s, 3H), 3.51-3.36 (m, 3H), 3.21-3.19 (m, 2H), 2.69-2.62 (m, 3H); ESI-MS m/z 328 [M+H]$^+$.

Example 36

S-(−)-2-bihydroxy-3,12-bimethoxy-10,11-methylenedioxy-5,8,13,13a-tetrahydro-6H-dibenzo[a,g]quinolizine (DC037036)

The preparation method was described in Example 1. $^1$H NMR (CDCl$_3$): δ 6.92 (s, 1H), 6.86 (s, 1H), 6.61 (s, 1H), 5.81

(s, 2H), 4.13-4.08 (m, 1H), 3.88 (s, 3H), 3.86 (s, 3H), 3.84 (s, 3H), 3.54-3.48 (m, 2H), 3.32-3.23 (m, 3H), 2.83-2.77 (m, 1H), 2.63-2.54 (m, 2H); ESI-MS m/z 356 [M+H]+.

Example 37

S-(−)-2-hydroxy-3-methoxy-(2',2'-bifluoro-10,11-methylenedioxy)-5,8,13,13a-tetrahydro-6H-dibenzo[a,g]quinolizine (DC037037)

The preparation method was described in Example 1. $^1$H NMR (CDCl$_3$): δ 6.91 (s, 1H), 6.84 (s, 1H), 6.81 (s, 1H), 6.63 (s, 1H), 4.12-4.09 (m, 1H), 3.87 (s, 3H), 3.56-3.48 (m, 2H), 3.34-3.24 (m, 3H), 2.82-2.76 (m, 1H), 2.64-2.55 (m, 2H); ESI-MS m/z 362 [M+H]+.

Example 38

S-(−)-2-hydroxy-3-methoxyl-9-chloro-10,11-methylenedioxy-5,8,13,13a-tetrahydro-6H-dibenzo[a,g]quinolizine (DC037038)

The preparation method was described in Example 1. $^1$H NMR (CDCl$_3$): δ 6.92 (s, 1H), 6.86 (s, 1H), 6.61 (s, 1H), 5.81 (s, 2H), 4.13-4.08 (m, 1H), 3.88 (s, 3H), 3.86 (s, 3H), 3.84 (s, 3H), 3.54-3.48 (m, 2H), 3.32-3.23 (m, 3H), 2.83-2.77 (m, 1H), 2.63-2.54 (m, 2H); ESI-MS m/z 3602 [M+H]+.

Example 39

S-(−)-2-hydroxy-3-methoxyl-9-fluoro-10,11-methylenedioxy-5,8,13,13a-tetrahydro-6H-dibenzo[a,g]quinolizine (DC037039)

The preparation method was described in Example 1. $^1$H NMR (CDCl$_3$): δ 6.98 (s, 1H), 6.83 (s, 1H), 6.63 (s, 1H), 5.84 (s, 2H), 4.12-4.09 (m, 1H), 3.86 (s, 3H), 3.55-3.49 (m, 2H), 3.34-3.22 (m, 3H), 2.84-2.77 (m, 1H), 2.63-2.52 (m, 2H); ESI-MS m/z 344 [M+H]+.

Example 40

S-(−)-2-hydroxy-3-methoxyl-10,11-methylenedioxy-12-fluoro-5,8,13,13a-tetrahydro-6H-dibenzo[a,g]quinolizine (DC037040)

The preparation method was described in Example 1. ESI-MS m/z 344 [M+H]+.

Example 41

S-(−)-2-hydroxy-3-methoxyl-10,11-methylenedioxy-12-chloro-5,8,13,13a-tetrahydro-6H-dibenzo[a,g]quinolizine (DC037041)

The preparation method was described in Example 1. ESI-MS m/z 360 [M+H]+.

Example 42

S-(−)-2,3-methylenedioxy-10,11-methylenedioxy-12-fluoro-5,8,13,13a-tetrahydro-6H-dibenzo[a,g]quinolizine (DC037042)

The preparation method was described in Example 1. ESI-MS m/z 342 [M+H]+.

Example 43

S-(−)-2,3-methylenedioxy-(2',2'-bifluoro-10,11-methylenedioxy)-5,8,13,13a-tetrahydro-6H-dibenzo[a,g]quinolizine (DC037043)

The preparation method was described in Example 1. ESI-MS m/z 360 [M+H]+.

Example 44

S-(−)-2-hydroxy-3-fluoro-9,12-bimethoxy-5,8,13,13a-tetrahydro-6H-dibenzo[a,g]quinolizine (DC037044)

The preparation method was described in Example 1. ESI-MS m/z 330 [M+H]+.

Example 45

S-(−)-2-hydroxy-3-chloro-9,12-bimethoxy-5,8,13,13a-tetrahydro-6H-dibenzo[a,g]quinolizine (DC037045)

The preparation method was described in Example 1. ESI-MS m/z 346 [M+H]+.

Example 46

S-(−)-2-hydroxy-3-chloro-10,11-methylenedioxy-5,8,13,13a-tetrahydro-6H-dibenzo[a,g]quinolizine (DC037046)

The preparation method was described in Example 1. ESI-MS m/z 330 [M+H]+.

Example 47

S-(−)-2-hydroxy-3-fluoro-10,11-methylenedioxy-5,8,13,13a-tetrahydro-6H-dibenzo[a,g]quinolizine (DC037047)

The preparation method was described in Example 1. ESI-MS m/z 314 [M+H]+.

Example 48

S-(−)-2,3-methylenedioxy-10,11-methylenedioxy-12-chloro-5,8,13,13a-tetrahydro-6H-dibenzo[a,g]quinolizine (DC037048)

The preparation method was described in Example 1. ESI-MS m/z 358 [M+H]+.

Example 49

(6R,14S)-3,9,10,11-tetramethoxy-6-methyl-5,8,13,13a-tetrahydro-6H-dibenzo[a,g]quinolizine (DC037049)

Compound DC037049 was prepared according to the method described in Example 1 except that 1.64 g of 3-methoxypropiophenone was dissolved in 40 mL of anhydrous methanol, 0.924 mg of ammonium acetate was added to above solution, and 3-methoxyphenyl-propanamine was obtained by hydrogenation under the catalytic action of palladium carbon. $^1$H NMR (CDCl$_3$): δ 7.13-7.15 (d, J=8.4, 1H), 6.74-6.77 (dd, J=8.4, J=2.4, 1H), 6.60-6.61 (d, J=2.4, 1H), 6.45 (s, 1H), 4.39-4.43 (d, J=15.2, 1H), 3.89 (s, 3H), 3.82 (s, 3H), 3.81 (s, 3H), 3.78 (s, 3H), 3.60-3.64 (m, 1H), 3.18-3.28 (m, 2H), 2.83-2.87 (m, 2H), 2.65-2.69 (m, 2H), 1.35-1.37 (d, J=6, 3H); ESI-MS m/z 370 [M+H]+.

Example 50

(6S,14S)-3,9,10,11-tetramethoxy-6-methyl-5,8,13,13a-tetrahydro-6H-dibenzo[a,g]quinolizine (DC037050)

The preparation method was described in Example 49. $^1$H NMR (CDCl$_3$): δ 7.15-7.17 (d, J=8.4, 1H), 6.76-6.78 (dd, J=8.4, J=2.4, 1H), 6.62-6.63 (d, J=2.4, 1H), 6.47 (s, 1H), 4.41-4.45 (d, J=15.2, 1H), 3.91 (s, 3H), 3.84 (s, 3H), 3.83 (s, 3H), 3.62-3.67 (m, 1H), 3.20-3.30 (m, 2H), 2.85-2.89 (m, 2H), 2.67-2.71 (m, 2H), 1.37-1.39 (d, J=6, 3H); ESI-MS m/z 370 [M+H]+.

Example 51

(6R,14S)-2,3,9,10-tetramethoxy-6-methyl-5,8,13,13a-tetra-hydro-6H-dibenzo[a,g]quinolizine (DC037051) (prepared according to the second reaction route)

Compound DC037051 was prepared according to the following Example 81 except that 1.74 g of 2,3-bimethoxypropiophenone was dissolved in 40 mL of anhydrous methanol, ammonium acetate was added to above solution, and 2,3-bimethoxyphenyl-propanamine was obtained by hydrogenation under the catalytic action of palladium carbon. $^1$H NMR (CDCl$_3$): δ 6.86-6.89 (d, J=8.4, 1H), 6.77-6.80 (d, J=9, 1H), 6.72 (s, 1H), 6.58 (s, 1H), 4.52-4.57 (d, J=15.9, 1H), 3.88 (s, 3H), 3.86 (s, 3H), 3.85 (s, 3H), 3.85 (s, 3H), 3.59-3.64 (m, 1H), 3.24-3.33 (m, 2H), 2.79-2.95 (m, 2H), 2.61-2.65 (m, 2H), 1.38-1.40 (d, J=6.8, 3H); ESI-MS m/z 370 [M+H]+.

Example 52

(6S,14S)-2,3,9,10-tetramethoxy-6-methyl-5,8,13,13a-tetrahydro-6H-dibenzo[a,g]quinolizine (DC037052) (prepared according to the second reaction route)

The preparation method was described in Example 81. $^1$H NMR (CDCl$_3$): δ 6.85-6.88 (d, J=9, 1H), 6.77-6.80 (d, J=8.4, 1H), 6.71 (s, 1H), 6.58 (s, 1H), 4.52-4.57 (d, J=15.9, 1H), 3.88 (s, 3H), 3.86 (s, 3H), 3.85 (s, 3H), 3.85 (s, 3H), 3.59-3.64 (m, 1H), 3.24-3.33 (m, 2H), 2.79-2.95 (m, 2H), 2.61-2.65 (m, 2H), 1.38-1.40 (d, J=6.8, 3H); ESI-MS m/z 370 [M+H]+.

Example 53

(6R,14S)-2,3,9,10,11-pentamethoxyl-6-methyl-5,8,13,13a-tetrahydro-6H-dibenzo[a,g]quinolizine (DC037053)

The preparation method was described in Example 49. $^1$H NMR (CDCl$_3$): δ 6.71 (s, 1H), 6.58 (s, 1H), 6.48 (s, 1H), 6.58 (s, 1H), 4.41-4.46 (d, J=15, 1H), 3.89 (s, 3H), 3.88 (s, 3H), 3.86 (s, 3H), 3.84 (s, 3H), 3.84 (s, 3H), 3.62-3.65 (m, 1H), 3.20-3.29 (m, 2H), 2.79-2.90 (m, 2H), 2.61-2.66 (m, 2H), 1.37-1.39 (d, J=6, 3H); ESI-MS m/z 400[M+H]+.

Example 54

(6S,14S)-2,3,9,10,11-pentamethoxyl-6-methyl-5,8,13,13a-tetrahydro-6H-dibenzo[a,g]quinolizine (DC037054)

The preparation method was described in Example 49. $^1$H NMR (CDCl$_3$): δ 6.71 (s, 1H), 6.59 (s, 1H), 6.48 (s, 1H), 6.58 (s, 1H), 4.41-4.46 (d, J=15, 1H), 3.90 (s, 3H), 3.88 (s, 3H), 3.86 (s, 3H), 3.84 (s, 3H), 3.84 (s, 3H), 3.62-3.64 (m, 1H), 3.19-3.27 (m, 2H), 2.79-2.91 (m, 2H), 2.61-2.66 (m, 2H), 1.37-1.39 (d, J=6, 3H); ESI-MS m/z 400 [M+H]+.

Example 55

(6R,14S)-2,3,9,11-tetramethoxy-6-methyl-12-hydroxymethyl-5,8,13,13a-tetrahydro-6H-dibenzo[a,g]quinolizine (DC037055)

The preparation method was described in Example 49. $^1$H NMR (CDCl$_3$): δ 6.91 (s, 1H), 6.63 (s, 1H), 6.49 (s, 1H), 4.58-4.70 (m, 2H), 4.32-4.37 (d, J=15, 1H), 3.87 (s, 3H), 3.84 (s, 3H), 3.83 (s, 3H), 3.81 (s, 3H), 3.58-3.65 (m, 1H), 3.50-3.54 (m, 1H), 3.06-3.11 (m, 1H), 2.70-2.82 (m, 2H), 2.59-2.65 (m, 2H), 1.30-1.33 (d, J=6, 3H); ESI-MS m/z 400 [M+H]+.

Example 56

(6S,14S)-2,3,9,11-tetramethoxy-6-methyl-12-hydroxymethyl-5,8,13,13a-tetrahydro-6H-dibenzo[a,g]quinolizine (DC037056)

The preparation method was described in Example 49. $^1$H NMR (CDCl$_3$): δ 6.92 (s, 1H), 6.63 (s, 1H), 6.50 (s, 1H), 4.58-4.70 (m, 2H), 4.31-4.36 (d, J=15, 1H), 3.86 (s, 3H), 3.84 (s, 3H), 3.83 (s, 3H), 3.80 (s, 3H), 3.58-3.64 (m, 1H), 3.50-3.53 (m, 1H), 3.06-3.11 (m, 1H), 2.70-2.82 (m, 2H), 2.59-2.65 (m, 2H), 1.30-1.33 (d, J=6, 3H); ESI-MS m/z 400 [M+H]+.

Example 57

(6R,14S)-3,9,11-trimethoxy-6-methyl-12-hydroxymethyl-5,8,13,13a-tetrahydro-6H-dibenzo[a,g]quinolizine (DC037057)

The preparation method was described in Example 49. $^1$H NMR (CDCl$_3$): δ 7.20-7.23 (d, J=8.7, 1H), 6.75-6.79 (dd, J=8.7, J=2.4, 1H), 6.61-6.62 (d, J=2.4, 1H), 6.34 (s, 1H), 4.64-4.74 (m, 2H), 4.37-4.42 (d, J=15, 1H), 3.85 (s, 3H), 3.84 (s, 3H), 3.79 (s, 3H), 3.62-3.65 (m, 1H), 3.50-3.51 (m, 1H), 3.13-3.18 (m, 1H), 2.89-2.90 (m, 2H), 2.67-2.70 (m, 2H), 1.38-1.40 (d, J=6, 3H); ESI-MS m/z 370[M+H]+.

Example 58

(6S,14S)-3,9,11-trimethoxy-6-methyl-12-hydroxymethyl-5,8,13,13a-tetrahydro-6H-dibenzo[a,g]quinolizine (DC037058)

The preparation method was described in Example 49. $^1$H NMR (CDCl$_3$): δ 7.20-7.23 (d, J=8.7, 1H), 6.76-6.80 (dd, J=8.7, J=2.4, 1H), 6.60 (d, J=2.4, 1H), 6.34 (s, 1H), 4.63-4.74 (m, 2H), 4.37-4.42 (d, J=15, 1H), 3.85 (s, 3H), 3.84 (s, 3H), 3.80 (s, 3H), 3.62-3.65 (m, 1H), 3.50-3.51 (m, 1H), 3.13-3.18

(m, 1H), 2.89-2.90 (m, 2H), 2.66-2.70 (m, 2H), 1.38-1.40 (d, J=6, 3H); ESI-MS m/z 370 [M+H]⁺.

Example 59

(6R,14S)-2-hydroxy-3,9,10,11-tetramethoxy-6-methyl-5,8,13,13a-tetrahydro-6H-dibenzo[a,g]quinolizine (DC037059)

The preparation method was described in Example 49. $^1$H NMR (CDCl$_3$): δ 6.91 (s, 1H), 6.67 (s, 1H), 6.45 (s, 1H), 4.40-4.45 (d, J=15, 1H), 3.93 (s, 3H), 3.87 (s, 3H), 3.82 (s, 6H), 3.61-3.63 (m, 1H), 3.18-3.23 (m, 2H), 2.82-2.91 (m, 2H), 2.66-2.70 (m, 2H), 1.37-1.39 (d, J=6, 3H); ESI-MS m/z 386 [M+H]⁺.

Example 60

(6S,14S)-2-hydroxy-3,9,10,11-tetramethoxy-6-methyl-5,8,13,13a-tetrahydro-6H-dibenzo[a,g]quinolizine (DC037060)

The preparation method was described in Example 49. $^1$H NMR (CDCl$_3$): δ 6.90 (s, 1H), 6.67 (s, 1H), 6.46 (s, 1H), 4.40-4.45 (d, J=15, 1H), 3.92 (s, 3H), 3.87 (s, 3H), 3.83 (s, 6H), 3.61-3.63 (m, 1H), 3.18-3.24 (m, 2H), 2.83-2.91 (m, 2H), 2.66-2.70 (m, 2H), 1.38-1.40 (d, J=6, 3H); ESI-MS m/z 386 [M+H]⁺.

Example 61

(6R,14S)-2-hydroxy-3,9,11-trimethoxy-6-methyl-5,8,13,13a-tetrahydro-6H-dibenzo[a,g]quinolizine (DC037061)

The preparation method was described in Example 49. $^1$H NMR (CDCl$_3$): δ 6.97 (s, 1H), 6.75 (s, 1H), 6.66 (s, 1H), 6.36 (s, 1H), 4.37-4.42 (d, J=15, 1H), 3.87 (s, 3H), 3.85 (s, 3H), 3.79 (s, 3H), 3.53-3.59 (m, 1H), 3.43-3.50 (m, 1H), 3.08-3.12 (m, 1H), 2.73-2.81 (m, 2H), 2.62-2.68 (m, 2H), 1.36-1.38 (d, J=6, 3H); ESI-MS m/z 356 [M+H]⁺.

Example 62

(6S,14S)-2-hydroxy-3,9,11-trimethoxy-6-methyl-5,8,13,13a-tetrahydro-6H-dibenzo[a,g]quinolizine (DC037062)

The preparation method was described in Example 49. $^1$H NMR (CDCl$_3$): δ 6.98 (s, 1H), 6.77 (s, 1H), 6.65 (s, 1H), 6.36 (s, 1H), 4.39-4.44 (d, J=15, 1H), 3.87 (s, 3H), 3.85 (s, 3H), 3.79 (s, 3H), 3.53-3.58 (m, 1H), 3.42-3.48 (m, 1H), 3.06-3.11 (m, 1H), 2.73-2.80 (m, 2H), 2.62-2.68 (m, 2H), 1.36-1.38 (d, J=6, 3H); ESI-MS m/z 356 [M+H]⁺.

Example 63

(6R,14S)-2-hydroxy-3,9,11-trimethoxy-6-methyl-12-hydroxy-methyl-5,8,13,13a-tetrahydro-6H-dibenzo[a,g]quinolizine (DC037063)

The preparation method was described in Example 49. $^1$H NMR (CDCl$_3$): δ 6.97 (s, 1H), 6.66 (s, 1H), 6.36 (s, 1H), 4.57-4.76 (m, 2H), 4.37-4.42 (d, J=15, 1H), 3.86 (s, 3H), 3.85 (s, 3H), 3.81 (s, 3H), 3.57-3.64 (m, 1H), 3.42-3.49 (m, 1H), 3.10-3.15 (m, 1H), 2.77-2.88 (m, 2H), 2.64-2.71 (m, 2H), 1.35-1.37 (d, J=6, 3H); ESI-MS m/z 386 [M+H]⁺.

Example 64

(6S,14S)-2-hydroxy-3,9,11-trimethoxy-6-methyl-12-hydroxy-methyl-5,8,13,13a-tetrahydro-6H-dibenzo[a,g]quinolizine (DC037064)

The preparation method was described in Example 49. $^1$H NMR (CDCl$_3$): δ 6.99 (s, 1H), 6.67 (s, 1H), 6.36 (s, 1H), 4.58-4.76 (m, 2H), 4.37-4.42 (d, J=15, 1H), 3.87 (s, 3H), 3.85 (s, 3H), 3.81 (s, 3H), 3.57-3.65 (m, 1H), 3.44-3.49 (m, 1H), 3.10-3.14 (m, 1H), 2.77-2.88 (m, 2H), 2.65-2.71 (m, 2H), 1.37-1.39 (d, J=6, 3H); ESI-MS m/z 386 [M+H]⁺.

Example 65

(6R,14S)-2,3-bimethoxy-6,9,11-trimethyl-5,8,13,13a-tetrahydro-6H-dibenzo[a,g]quinolizine (DC037065)

The preparation method was described in Example 49. $^1$H NMR (CDCl$_3$): δ 6.85 (s, 1H), 6.83 (s, 1H), 6.73 (s, 1H), 6.58 (s, 1H), 3.99-4.14 (m, 1H), 3.88 (s, 3H), 3.86 (s, 3H), 3.63-3.66 (m, 1H), 3.25-3.28 (m, 2H), 2.82-2.96 (m, 2H), 2.62-2.71 (m, 2H), 2.28 (s, 6H), 1.37-1.39 (d, J=6, 3H); ESI-MS m/z 340 [M+H]⁺.

Example 66

(6S,14S)-2,3-bimethoxy-6,9,11-trimethyl-5,8,13,13a-tetrahydro-6H-dibenzo[a,g]quinolizine (DC037066)

The preparation method was described in Example 49. $^1$H NMR (CDCl$_3$): δ 6.84 (s, 1H), 6.83 (s, 1H), 6.72 (s, 1H), 6.58 (s, 1H), 4.01-4.15 (m, 1H), 3.88 (s, 3H), 3.86 (s, 3H), 3.63-3.65 (m, 1H), 3.24-3.28 (m, 2H), 2.82-2.95 (m, 2H), 2.61-2.70 (m, 2H), 2.27 (s, 6H), 1.37-1.39 (d, J=6, 3H); ESI-MS m/z 340 [M+H]⁺.

Example 69

(S)-2,3,11-trimethoxy-5,8,13,13a-tetrahydro-6H-dibenzo[a,g]quinolizine (DC037067)

The preparation method was described in Example 1. $^1$H NMR (CDCl$_3$): δ 6.99-7.02 (d, J=9, 1H), 6.75 (s, 2H), 6.72 (s, 1H), 6.62 (s, 1H), 4.01-4.13 (m, 1H), 3.91 (s, 3H), 3.88 (s, 3H), 3.79 (s, 3H), 3.56-3.68 (m, 2H), 3.28-3.35 (m, 1H), 3.12-3.19 (m, 2H), 2.80-2.94 (m, 1H), 2.62-2.70 (m, 2H); ESI-MS m/z 326 [M+H]⁺.

Example 68

(S)-2-hydroxy-3,11-bimethoxy-5,8,13,13a-tetrahydro-6H-dibenzo[a,g]quinolizine (DC037068)

The preparation method was described in Example 1. $^1$H NMR (CDCl$_3$): δ 6.97-7.00 (d, J=9, 1H), 6.85 (s, 1H), 6.69-6.74 (m, 2H), 6.60 (s, 1H), 4.00-4.12 (m, 1H), 3.87 (s, 3H), 3.78 (s, 3H), 3.57-3.69 (m, 2H), 3.26-3.32 (m, 1H), 3.10-3.16 (m, 2H), 2.84-2.93 (m, 1H), 2.63-2.69 (m, 2H); ESI-MS m/z 312 [M+H]⁺.

Example 69

(S)-2-benzyloxy-3,11-bimethoxy-5,8,13,13a-tetrahydro-6H-dibenzo[a,g]quinolizine (DC037069)

The preparation method was described in Example 1. $^1$H NMR (CDCl$_3$): δ 7.46-7.47 (m, 2H), 7.39-7.40 (m, 2H), 7.31-7.33 (m, 1H), 6.97-7.00 (d, J=9, 1H), 6.76 (s, 1H), 6.70-6.74 (m, 1H), 6.64-6.66 (m, 2H), 5.15 (s, 2H), 3.94-3.99 (m, 1H), 3.88 (s, 3H), 3.79 (s, 3H), 3.62-3.66 (m, 1H), 3.50-3.54 (m, 1H), 3.11-3.16 (m, 2H), 2.77-2.81 (m, 1H), 2.60-2.69 (m, 2H); ESI-MS m/z 402 [M+H]$^+$.

Example 70

(S)-2,3-methylenedioxy-11-methoxyl-5,8,13,13a-tetrahydro-6H-dibenzo[a,g]quinolizine (DC037070)

The preparation method was described in Example 49. $^1$H NMR (CDCl$_3$): δ 6.98-7.01 (d, J=9, 1H), 6.69-6.74 (m, 3H), 6.59 (s, 1H), 5.92 (s, 2H), 3.94-3.99 (m, 1H), 3.79 (s, 3H), 3.56-3.68 (m, 2H), 3.22-3.29 (m, 1H), 3.09-3.16 (m, 2H), 2.83-2.92 (m, 1H), 2.60-2.67 (m, 2H); ESI-MS m/z 310 [M+H]$^+$.

Example 71

(6R,14S)-2-hydroxy-3,9,12-trimethoxy-6-methyl-5,8,13,13a-tetra-hydro-6H-dibenzo[a,g]quinolizine (DC037071)

The preparation method was described in Example 49. $^1$H NMR (CDCl$_3$): δ 6.89 (s, 1H), 6.64 (s, 2H), 6.55 (s, 1H), 4.44-4.48 (m, 1H), 3.86 (s, 3H), 3.79 (s, 3H), 3.78 (s, 3H), 3.52-3.60 (m, 1H), 3.38-3.42 (m, 1H), 3.14-3.22 (m, 1H), 2.78-2.86 (m, 1H), 2.58-2.66 (m, 3H), 1.36-1.38 (d, J=6, 3H); ESI-MS m/z 356 [M+H]$^+$.

Example 72

(6S,14S)-2-hydroxy-3,9,12-trimethoxy-6-methyl-5,8,13,13a-tetra-hydro-6H-dibenzo[a,g]quinolizine (DC037072)

The preparation method was described in Example 1. $^1$H NMR (CDCl$_3$): δ 6.88 (s, 1H), 6.64 (s, 2H), 6.54 (s, 1H), 4.43-4.47 (m, 1H), 3.86 (s, 3H), 3.80 (s, 3H), 3.79 (s, 3H), 3.53-3.60 (m, 1H), 3.38-3.43 (m, 1H), 3.15-3.24 (m, 1H), 2.77-2.84 (m, 1H), 2.58-2.67 (m, 3H), 1.36-1.38 (d, J=6, 3H); ESI-MS m/z 356 [M+H]$^+$.

Example 73

(6S,14R)-2,10-bihydroxy-3,9-bimethoxy-6-methyl-5,8,13,13a-tetra-hydro-6H-dibenzo[a,g]quinolizine (DC037073)(prepared according to the second reaction route)

Compound DC037073 was prepared according to the following Example 81 except that 1.74 g of 2,3-bimethoxypropiophenone was dissolved in 40 mL of anhydrous methanol, 0.96 mg of ammonium acetate was added to above solution, and 2,3-bimethoxyphenyl-propanamine was obtained by hydrogenation under the catalytic action of palladium carbon. $^1$H NMR (CDCl$_3$): δ 6.80-6.82 (m, 3H), 6.56 (s, 1H), 5.30-5.50 (m, 2H), 4.49-4.56 (m, 1H), 3.87 (s, 3H), 3.82 (s, 3H), 3.58-3.62 (m, 1H), 3.24-3.35 (m, 2H), 3.15-3.24 (m, 1H), 2.77-2.88 (m, 2H), 2.60-2.66 (m, 2H), 1.36-1.38 (d, J=6, 3H); ESI-MS m/z 342 [M+H]$^+$.

Example 74

(6S,14S)-2,10-bihydroxy-3,9-bimethoxy-6-methyl-5,8,13,13a-tetrahydro-6H-dibenzo[a,g]quinolizine (DC037074)(prepared according to the second reaction route)

The preparation method was described in Example 81. $^1$H NMR (CDCl$_3$): δ 6.80-6.82 (m, 3H), 6.56 (s, 1H), 5.28-5.49 (m, 2H), 4.50-4.56 (m, 1H), 3.86 (s, 3H), 3.81 (s, 3H), 3.56-3.61 (m, 1H), 3.24-3.34 (m, 2H), 3.16-3.24 (m, 1H), 2.76-2.85 (m, 2H), 2.58-2.64 (m, 2H), 1.36-1.38 (d, J=6, 3H); ESI-MS m/z 342 [M+H]$^+$.

Example 75

(S)-2,3,9,11-tetramethoxy-5,8,13,13a-tetrahydro-6H-dibenzo[a,g]quinolizine (DC037075)

The preparation method was described in Example 1. $^1$H NMR (CDCl$_3$): δ 6.72 (s, 1H), 6.60 (s, 1H), 6.30 (s, 2H), 4.07-4.12 (d, J=15, 1H), 3.87 (s, 3H), 3.85 (s, 3H), 3.78 (s, 3H), 3.77 (s, 3H), 3.55-3.59 (m, 1H), 3.35-3.40 (m, 3H), 3.15-3.28 (m, 2H), 2.63-2.67 (m, 2H); ESI-MS m/z 356 [M+H]$^+$.

Example 76

(S)-2,3,9,11-tetramethoxy-12-hydroxymethyl-5,8,13,13a-tetra-hydro-6H-dibenzo[a,g]quinolizine (DC037076)

The preparation method was described in Example 1. $^1$H NMR (CDCl$_3$): δ 6.77 (s, 1H), 6.60 (s, 1H), 6.35 (s, 1H), 4.60-4.76 (m, 2H), 4.08-4.13 (d, J=15, 1H), 3.88 (s, 3H), 3.85 (s, 6H), 3.81 (s, 3H), 3.51-3.55 (m, 2H), 3.35-3.46 (m, 2H), 3.12-3.17 (m, 2H), 2.60-2.67 (m, 2H); ESI-MS m/z 386 [M+H]$^+$.

Example 77

(S)-2,3-methylenedioxy-9,11-bimethoxy-12-hydroxymethyl-5,8,13,13a-tetrahydro-6H-dibenzo[a,g]quinolizine (DC037077)

The preparation method was described in Example 1. $^1$H NMR (CDCl$_3$): δ 6.78 (s, 1H), 6.58 (s, 1H), 6.35 (s, 1H), 5.88 (s, 2H), 4.60-4.76 (m, 2H), 4.09-4.14 (d, J=15, 1H), 3.87 (s, 3H), 3.84 (s, 3H), 3.47-3.55 (m, 2H), 3.35-3.43 (m, 2H), 3.11-3.18 (m, 2H), 2.58-2.67 (m, 2H); ESI-MS m/z 370 [M+H]$^+$.

Example 78

(S)-2,3-methylenedioxy-9,11-bimethoxy-5,8,13,13a-tetrahydro-6H-dibenzo[a,g]quinolizine (DC037078)

The preparation method was described in Example 1. $^1$H NMR (CDCl$_3$): δ 6.73 (s, 1H), 6.59 (s, 1H), 6.30 (s, 2H), 5.90 (s, 2H), 4.07-4.12 (d, J=15, 1H), 3.82 (s, 3H), 3.79 (s, 3H), 3.52-3.56 (m, 1H), 3.35-3.40 (m, 1H), 3.06-3.24 (m, 3H), 2.80-2.89 (m, 1H), 2.57-2.68 (m, 2H); ESI-MS m/z 340 [M+H]$^+$.

Example 79

(S)-2-hydroxy-3,9,11-trimethoxy-5,8,13,13a-tetrahydro-6H-dibenzo-[a,g]quinolizine (DC037079)

The preparation method was described in Example 1. $^1$H NMR (CDCl$_3$): δ 6.81 (s, 1H), 6.59 (s, 1H), 6.29 (s, 2H), 4.07-4.12 (d, J=15, 1H), 3.87 (s, 3H), 3.79 (s, 3H), 3.78 (s, 3H), 3.52-3.58 (m, 1H), 3.36-3.42 (m, 1H), 3.06-3.26 (m, 3H), 2.79-2.89 (m, 1H), 2.58-2.69 (m, 2H); ESI-MS m/z 342 [M+H]$^+$.

Example 80

(S)-2-hydroxy-3,9,11-trimethoxy-12-hydroxymethyl-5,8,13,13a-tetrahydro-6H-dibenzo[a,g]quinolizine (DC037080)

The preparation method was described in Example 1.

Example 81

S-(−)-9-methoxyl-10-hydroxy-2,3,5,8,13,13a-hexahydro-8H-benzo[3,2,a,g]furanquinolizine (DC037081)(prepared according to the second reaction route)

2.1 Preparation of methyl 3-bromo-4-hydroxy-phenylacetate (Compound 10)

Methyl 3-hydroxy-phenylacetate (16.6 g, purchased from Accela ChemBio Co., Ltd.) was dissolved in glacial acetic acid (100 mL) and liquid bromine solution in glacial acetic acid (16 g in 50 mL glacial acetic acid) was dropwise added to above solution. The reaction was conducted for 2 hours and the product was obtained by filtering.

$^1$H NMR (CDCl$_3$, 300 MHz): δ 7.39 (d, J=1.5 Hz, 1H), 7.11 (dd, J=8.4 Hz, J=1.5 Hz, 1H), 6.93 (d, J=8.4 Hz, 1H), 3.70 (s, 3H), 3.54 (s, 2H).

2.2 Preparation of methyl 3-bromo-4-benzyloxy-phenylacetate (Compound 11)

Compound 10 (12.3 g) was dissolved in 100 mL acetone and 7.6 g of potassium carbonate was added. 8.6 g of benzyl bromide was added with stirring. The solid was removed by suction filtration and the liquid was evaporated to product 11.

$^1$H NMR (CDCl$_3$, 300 MHz): δ 7.51-7.33 (m, 6H), 7.15 (dd, J=8.4 Hz, J=2.4 Hz, 1H), 6.89 (d, J=8.4 Hz, 1H), 5.15 (s, 2H), 3.70 (s, 3H), 3.55 (s, 2H).

2.3 Preparation of 3-hydroxy-benzyloxyphenylacetic acid (Compound 12)

The substrate 11 (3.4 g), 6 mL of water, 1.5 g of KOH and 150 mg Cu powder were loaded into a microwave reaction tube and stirred at room temperature for half an hour. The obtained mixture was degassed by ultrasound. At 140° C., the microwave reaction proceeded for 50 minutes. The undissolved substance was filtered off. The pH value of the solution was adjusted to 1-3 by concentrated hydrochloric acid. The crude product was obtained by filtration. The product was recrystallizated with toluene to obtain Compound 12.

$^1$H NMR (CDCl$_3$, 300 MHz): δ 7.43-7.38 (m, 5H), 6.90 (s, 1H), 6.89 (dd, J=8.1 Hz, J=2.1 Hz, 1H), 6.74 (d, J=8.1 Hz, 1H), 5.10 (s, 2H), 3.56 (s, 2H).

2.4 Preparation of Compound 13

The substrate 12 (3 g), phenylboronic acid (2.7 g) and 60 mL of anhydrous toluene were added to the reaction bottle. The reaction mixture was placed in 110° C. oil bath for reacting for 2 hours. The reaction mixture was poured into a sealed tube while 3 g of paraformaldehyde and appropriate amount of molecular sieves were added. The reaction proceeded at 100° C. for 46 hours. After completion of the reaction, the molecular sieves were filtered off while they were hot and toluene was evaporated to obtain a slightly yellow solid. 50 mL of water was added and the reaction proceeded in 100° C. oil bath for 2 hours. After cooled, the reaction mixture was extracted with dichloromethane until there is no product in aqueous phase. The dichloromethane phase was dried over anhydrous sodium sulfate and evaporated to dryness to obtain a slightly yellow solid. An appropriate amount of anhydrous ether was added, stirred for 3 hours at room temperature, and then filtered to give a white solid, i.e. Compound 13.

The preparation was carried out with reference to Richard J. Spangler, Brian G. Beckmann, Jong Ho Kim. *J. org. chem.*, 1977, 42, 2989-2996. Mark Cushman, Frederick W. Dekow. *J. org. chem.*, 1979, 44, 407-409.

2.5 Preparation of Compound 14

Compound 13 (2.7 g) was dissolved in acetone (50 mL) Potassium carbonate (6.2 g) and iodomethane (15.5 g) were added. The reaction mixture was refluxed for 2 hours. The insoluble substances were filtered off and the solvent was evaporated. Product 14 was obtained by column chromatography.

$^1$H NMR (CDCl$_3$, 300 MHz): δ 7.45-7.34 (m, 5H), 6.92 (d, J=8.2 Hz, 1H), 6.85 (d, J=8.2 Hz, 1H), 5.40 (s, 2H), 5.12 (s, 2H), 3.91 (s, 3H), 3.62 (s, 2H).

2.6 Preparation of Compound 15

Compound 14 (2.84 g) was dissolved in glacial acetic acid and a solution of concentrated nitric acid in glacial acetic acid (630 mg in 6 mL of glacial acetic acid) was added slowly to above solution. The reaction was conducted for 2 hours and product 15 was obtained by column chromatography.

2.7 Preparation of Compound 16

Compound 15 (658 mg) and 2-[5-(2,3-dihydrobenzofuranyl)]-ethylamine (516 mg) were dissolved in 7 mL of anhydrous ethanol. The reaction mixture was refluxed overnight, and cooled to precipitate solid. Product 16 was obtained by filtration.

$^1$H NMR (CDCl$_3$, 300 MHz): δ 7.48-7.32 (m, 5H), 6.93 (d, J=8.4, 1 H), 6.86 (d, J=8.4 Hz, 1H), 6.74 (d, J=8.1 Hz, 1H), 6.65 (d, J=1.8, 1H), 6.54 (dd, J=8.1, 1.8 Hz, 1H), 6.10 (m, 1H), 5.07 (s, 2H), 4.61 (s, 2H), 4.26 (t, 2H), 3.84 (s, 3H), 3.51 (s, 2H), 3.46-3.40 (q, J=6.8 Hz, 2H), 2.97 (t, 2H), 2.67 (t, J=6.8 Hz, 2H).

2.8 Preparation of Compound 17

Compound 16 (930 mg) was dissolved in anhydrous dichloromethane (25 mL) while anhydrous pyridine (0.24 mL) and a catalytic amount of DMAP were added. In an ice bath, a solution of acetyl chloride in dichloromethane was slowly added. After addition, the reaction was continued at room temperature for 1 hour and an appropriate amount of water was added. The reaction mixture was extracted with dichloromethane for three times. The dichloromethane layer was washed with saturated saline solution, dried over sodium sulfate and evaporated to dryness to give Compound 17 which can be directly used in next reaction without further purification.

$^1$H NMR (CDCl$_3$, 400 MHz): δ 7.44-7.32 (m, 5H), 6.92 (d, J=8.4, 1 H), 6.89 (d, J=8.4 Hz, 1H), 6.72 (d, J=8.0 Hz, 1H), 6.61 (d, J=1.6, 1H), 6.53 (dd, J=8.0, 1.6 Hz, 1H), 5.40 (m, 1H), 5.08 (s, 2H), 5.02 (s, 2H), 4.26 (t, 2H), 3.83 (s, 3H), 3.82 (s, 2H), 3.44-3.39 (q, J=6.8 Hz, 2H), 2.96 (s, 2H), 2.67-2.63 (t, J=6.8 Hz, 2H), 1.92 (s 3H).

2.9 Preparation of Compound 18

Compound 17 (760 mg) was dissolved in anhydrous acetonitrile (15 mL), to which phosphorus oxychloride (1.1 mL) was added. The reaction solution was refluxed for 30 min and then cooled to room temperature. Most of the solvent and the phosphorus oxychloride were evaporated. The reaction solution was neutralized by using saturated sodium bicarbonate solution and extracted with dichloromethane for three times. Most of the solvent was evaporated, and the reaction solution was neutralizated with saturated sodium bicarbonate solution, extracted for three times with dichloromethane. The extract phase was dried over sodium sulfate and evaporated to dryness to give Compound 18 which can be directly used in next reaction without further purification.

$^1$H NMR (CDCl$_3$, 400 MHz): δ 7.43-7.31 (m, 5H), 6.96 (s, 1H), 6.83 (d, J=8.4 Hz, 1H), 6.77 (s, 1H), 6.73 (d, J=8.4 Hz, 1H), 5.20 (s, 1H), 5.02 (s, 2H), 4.68 (s, 2H), 4.28 (t, 2H), 4.01-3.98 (t, J=7.6 Hz, 2H), 3.84 (s, 2H), 2.97 (t, 2H), 3.09-3.06 (t, J=7.6 Hz, 2H), 2.00 (s, 3H).

2.10 Preparation of Compound 19

Compound 18 (489 mg) and R type of Noyori catalyst (7 mg) were dissolved in DMF (5 mL) A mixture of triethylamine and formic acid (v/v=5:2) was added into the reaction mixture and the reaction was conducted overnight at room temperature. The reaction solution was neutralized with saturated aqueous sodium bicarbonate solution to alkalinity and the mixture was extracted with ethyl acetate. The ester phase was washed once with saturated saline solution, dried and evaporated to dryness to give product 19.

$^1$H NMR (CDCl$_3$, 400 MHz): δ 7.43-7.31 (m, 5H), 7.01 (d, J=8.4, 1 H), 6.92 (d, J=8.4 Hz, 1H), 6.66 (s, 1H), 6.59 (s, 1H), 5.30 (m, 2H), 5.02 (s, 2H), 4.26 (t, 2H), 4.02-3.99 (m, 1H), 3.90 (s, 3H), 3.22-3.16 (m, 2H), 2.95 (t, 2H), 2.90-2.80 (m, 2H), 2.74-2.71 (m, 2H), 2.01 (s, 3H).

2.11 Preparation of Compound 20

Compound 19 (491 mg) was dissolved in ethanol (4.5 mL), and to the solution, water (1.5 mL) and sodium hydroxide (80 mg) were added. The solution was reacted at room temperature for 3 hours and solid precipitated. The target product 20 was obtained by filtration.

2.12 Preparation of Compound 21

Compound 20 (447 mg) was dissolved in anhydrous dichloromethane. Under N$_2$, thionyl chloride (0.53 mL) was added slowly to the solution cooled in ice-bath. After addition, the reaction proceeded at room temperature for 2 hours. A saturated sodium bicarbonate solution was added into the reaction solution to alkalinity and the reaction preceded at room temperature for 2 hours. The dichloromethane layer was separated and the aqueous phase was extracted for three times with dichloromethane. The ester phase was washed once with saturated sodium chloride solution, dried over sodium sulfate and evaporated to dryness. And then product 21 was obtained by column chromatography.

$^1$H NMR (CDCl$_3$, 400 MHz): δ 7.47-7.31 (m, 5H), 6.83 (d, J=8.1, 1 H), 6.78 (d, J=8.1 Hz, 1H), 6.75 (s, 1H), 6.64 (s, 1H), 5.14 (s, 2H), 4.27 (t, 2H), 4.25-4.19 (m, 1H), 3.87 (s, 3H), 3.54-3.45 (m, 2H), 3.21-3.06 (m, 3H), 2.76-2.59 (m, 5H).

2.13 Preparation of S-(+9-methoxyl-10-hydroxy-2,3,5,8,13,13a-hexahydro-8H-benzo[3,2,a,g]furanquinolizine Compound 21 (431 mg) was dissolved in ethanol, and concentrated hydrochloric acid was slowly added. The mixture was refluxed for 1.5 hours and then cooled to room temperature. Most of hydrochloric acid was evaporated and the residue was neutralized with aqueous ammonia to alkalinity. The resulting mixture was extracted with dichloromethane until no product remains in aqueous phase. And then the product was obtained by column chromatography.

$^1$H NMR (CDCl$_3$): δ 6.83 (m, 3H), 6.59 (s, 1H), 4.34-4.29 (m, 1H), 4.26 (t, 2H), 3.86 (s, 3H), 3.67-3.61 (m, 2H), 3.30-3.24 (m, 3H), 2.97 (t, 2H), 2.93-2.71 (m, 3H); ESI-MS m/z 324 [M+H]$^+$.

Example 82

S-(−)-2,3-bimethylenedioxy-9-methoxyl-10-hydroxy-5,8,13,13a-tetrahydro-6H-dibenzo[a,g]quinolizine (DC037082)

The preparation method was described in Example 81.
$^1$H NMR (CDCl$_3$): δ 6.87 (m, 2H), 6.76 (s, 1H), 6.60 (s, 1H), 4.34-4.29 (m, 1H), 4.28 (m, 4H), 3.85 (s, 3H), 3.31-3.25 (m, 3H), 2.97 (t, 2H), 2.92-2.70 (m, 3H); ESI-MS m/z 340 [M+H]$^+$.

Example 83

S-(−)-2'-methyl-9-methoxyl-10-hydroxy-2,3,5,8,13,13a-hexahydro-8H-benzo[3,2,a,g]furanquinolizine (DC037083)

The preparation method was described in Example 81.
$^1$H NMR (CDCl$_3$): δ 6.82 (m, 3H), 6.61 (s, 1H), 4.33-4.28 (m, 1H), 4.24 (m, 1H), 3.87 (s, 3H), 3.64-3.57 (m, 2H), 3.30-3.24 (m, 3H), 2.97 (t, 2H), 2.93-2.71 (m, 3H); ESI-MS m/z 338 [M+H]$^+$ Pharmacological Experiments 1. In the present invention, the pharmacological experiments were conducted to study the affinity of hexahydrodibenzo[a,g]quinolizine compound of general formula I and derivatives thereof on dopamine D$_1$, dopamine D$_2$, 5-HT$_{1A}$, and 5-HT$_{2A}$ receptor. The experimental materials required for pharmacological experiments were commercially available unless otherwise specified.

(1). Determination of the Affinity of Hexahydrodibenzo[a,g]Quinolizine Compound of General Formula I and Derivatives Thereof on Dopamine D1, Dopamine D$_2$, 5-HT$_{1A}$, and 5-HT$_{2A}$ Receptor.

1) The Experimental Method

Different concentrations (10$^{-5}$ M-10$^{-11}$ M) of the compound of the invention and corresponding isotope receptor ligand as well as receptor protein were loaded into the reaction tube and incubated in 30° C. water bath for 60 minutes. The reaction was terminated in a refrigerator. The reaction mixture was put in a Millipore filter (millipore) cell sample collector, filtered through suction filtration using GF/C glass fiber filter paper, and dried. The resulting sample was placed into 0.5 mL tube. 500 μL liquid scintillation fluid was added and intensity of radioactivity was determined by counting.

2) The Experimental Materials

① Construction of receptor and materials for cell culture: *Escherichia coli*. DH5α strain; insect virus transfer vector pVL1393 plasmid; BaculoGold linear Chinese baculovirus DNA, purchased from ParMingen company; mkD1RcDNA; rD2R cDNA; various restriction endonucleases, TaqDNA polymerase, T4 ligase, etc., LB medium; insect cell culture TNM-FH.

② the Experimental Materials for Receptor Binding

For dopamine D1 receptor: isotope receptor ligands [3H] SCH23390 (85.0 Ci/mmol) (D1-selective, purchased from Amersham Corporation), D1 receptor protein expressed in HEK-293 cells;

For D2 dopamine receptor: isotope receptor ligands [3H] Spiperone (77.0 Ci/mmol) (D2-selective, purchased from Amersham Corporation); D2 receptor protein expressed in HEK-293 cells;

For 5-HT1A receptor: isotope receptor ligands [3H] 8-OH-DPAT; 5-HT1A receptor protein expressed in HEK-293 cells;

For 5-HT2A receptor: isotope receptor ligands [3H]-Ketanserin; 5-HT2A receptor protein expressed in HEK-293 cells;

Firstly, the above receptor proteins are dissolved in DMSO and then diluted with double distilled water to the appropriate concentration ($10^{-5}$ M–$10^{-11}$ M).

(+) Butaclamo purchased from RBI company, GF/C glass fiber filter paper purchased from Whatman Co., scintillation fluid (dopamine D1, D2 receptors)/liposoluble scintillation fluid (5-HT1A, 5-HT2A receptor), Beckman LS-6500 multifunction liquid scintillation counter.

3) The Experimental Results are Showed in Table 1 and 3.

2. Determination of the Inhibition Property of Hexahydrodibenzo[a,g]Quinolizine Compound of General Formula I and Derivatives Thereof on Dopamine $D_2$ Receptor.

(1) The Experimental Method

Each medicament was dissolved in serum-free F12 culture medium containing 100 μM of IBMX. CHO cells which can stably express D2 receptor were pre-incubated at 37° C. for 10 min, and then 10 μM Forskoline and 10 μM Dopanie were added at the same time to react for 10 min. 100 μL, of pre-cooled 1 M of $HClO_4$ was added and the reaction was terminated at 4° C. for 1 hour. 20 μL of 2 M $K_2CO_3$ was added to neutralize the reaction. The resulting mixture was centrifugated at 3000 rpm for 15 min, and the precipitate $KClO_4$ was discarded. A certain amount of the supernatant was taken for cAMP detection. Spiperone and Quinpirole were used as positive control.

(2) The Experimental Materials (3) The Experimental Results are Showed in Table 2 and FIG. 1.

TABLE 1

Determination results of the affinity of some representative compounds on dopamine D1, and D2 receptors

| Compound No. | $D_1$ receptor | | | $D_2$ receptor | | |
|---|---|---|---|---|---|---|
| | inhibition ratio (%) | Ki (nM) | $IC_{50}$ (nM) | inhibition ratio (%) | Ki (nM) | $IC_{50}$ (nM) |
| DC037001 | 58.95 | ND | ND | 14.7 | ND | ND |
| DC037002 | 77.95 | ND | ND | 27.05 | ND | ND |
| DC037003 | 98.0 | 246.86 | 370.30 | 75.75 | ND | ND |
| DC037006 | 91.75 | 320.11 | 648.23 | 48.0 | ND | ND |
| DC037007 | 87.65 | 1003.72 | 2032.50 | 49.05 | ND | ND |
| DC037008 | 101.0 | 50.07 | 101.39 | 92.8 | 334.38 | 1727.60 |
| DC037009 | −13.6 | ND | ND | 0.35 | ND | ND |
| DC037010 | 66.8 | ND | ND | 51.5 | ND | ND |
| DC037011 | 59.3 | ND | ND | 41.7 | ND | ND |
| DC037012 | 95.8 | 147.91 | 299.52 | 89.3 | 239.90 | 1239.4 |
| DC037013 | 103.4 | 23.65 | 47.90 | 85.6 | 485.43 | 2508.05 |
| DC037014 | 58.2 | ND | ND | 25.8 | ND | ND |
| DC037015 | 59.2 | ND | ND | 59.3 | ND | ND |
| DC037016 | 95.5 | 376.83 | 763.07 | 66.2 | ND | ND |
| DC037017 | 94.5 | 337.78 | 684.01 | 97.4 | 223.61 | 1155.30 |
| DC037018 | 82.5 | 1440.62 | 2917.20 | 77.4 | ND | ND |
| DC037019 | 10.3 | ND | ND | 65.3 | ND | ND |
| DC037020 | 47.3 | ND | ND | 57.1 | ND | ND |
| DC037021 | 56.5 | ND | ND | 44.5 | ND | ND |
| DC037022 | 89.0 | 497.87 | 1008.16 | 10.6 | ND | ND |
| DC037024 | 91.3 | 740.67 | 1499.85 | 76.2 | ND | ND |
| DC037027 | 92.0 | 522.03 | 1057.10 | 64.7 | ND | ND |
| DC037029 | 99.63 | 4.20 | 8.19 | 100.08 | 32.16 | 91.11 |
| DC037030 | 99.89 | 3.70 | 7.22 | 74.27 | ND | ND |
| DC037031 | 98.99 | 28.91 | 56.37 | 90.10 | 160.99 | 456.13 |
| DC037032 | 99.21 | 25.25 | 49.23 | 28.67 | ND | ND |
| DC037033 | 91.94 | 208.21 | 416.4 | 13.75 | ND | ND |
| DC037034 | 95.30 | 248.04 | 483.67 | 17.36 | ND | ND |
| DC037035 | 99.68 | 6.72 | 13.27 | 84.30 | ND | ND |
| DC037081 | 22.60 | ND | ND | 73.07 | ND | ND |
| DC037082 | 99.32 | 7.51 | 14.65 | 63.94 | ND | ND |
| DC037075 | 97.88 | 64.12 | 113.81 | 39.50 | ND | ND |
| DC037077 | 97.33 | 182.41 | 323.79 | 41.75 | ND | ND |
| DC037078 | 97.79 | 74.50 | 141.58 | 1.02 | ND | ND |
| DC037079 | 99.99 | 5.18 | 9.85 | 76.21 | ND | ND |
| SCH-23390 | 100 | 1.24 | 2.52 | ND | ND | ND |
| Spiperone | ND | ND | ND | 100 | 0.50 | 2.56 |

ND: the test was not conducted.

TABLE 2

Determination results of the inhibition of some representative compounds on dopamine D2 receptor

| | $D_2$ receptor | |
|---|---|---|
| Compound No. | Antagonist IC50 | agonist IC50 |
| DC037003 | 3.30 μM | — |
| DC037008 | 4.03 μM | — |
| DC037013 | 9.74 μM | — |
| DC037017 | 16.19 μM | — |
| DC037018 | 15.61 μM | — |
| DC037024 | 0.591 μM | — |
| Spiperone | 0.0014 μM | — |
| Quinpirole | — | 0.462 μM |

—: no agonist activity

TABLE 3

Determination results of the affinity of some representative compounds on hydroxyptamine 5-HT$_{1A}$ and 5-HT$_{2A}$ receptor

| Compound No. | 5-HT$_{1A}$ receptor | | | 5-HT$_{2A}$ receptor | | |
|---|---|---|---|---|---|---|
| | inhibition ratio (%) | Ki (nM) | IC$_{50}$ (nM) | inhibition ratio (%) | Ki (nM) | IC$_{50}$ (nM) |
| DC037013 | 86.93 | ND | ND | 41.32% | ND | ND |
| DC037029 | 60.97 | ND | ND | 49.91 | ND | ND |
| DC037030 | 80.41 | 493.48 | 626.40 | 39.99 | ND | ND |
| DC037034 | 83.77 | 497.43 | 631.40 | 26.46 | ND | ND |
| DC037032 | 95.36 | 40.59 | 51.53 | 37.75 | ND | ND |
| DC037075 | 90.77 | 730.02 | 922.44 | 54.04% | ND | ND |
| DC0370077 | 88.63 | 599.89 | 758.03 | 45.63% | ND | ND |
| 5-HT | 100 | 0.62 | 0.79 | ND | ND | ND |
| Spiperone | ND | ND | ND | 100 | 2.94 | 5.67 |

ND: the test was not conducted.

It can be seen from the tables that the tested compounds, for example Compound DC037029, DC037030, DC037031, DC037032, DC037035, DC037079, and DC037082, have strong affinity on dopamine D1, D2 receptors. Further, some compounds of the present invention exhibit a certain affinity on 5-HT1A.

2. Results of In Vivo Pharmacokinetic Experiment of Rats

Pharmacokinetic properties of Compound DC037029 in rats were preliminarily studied in this experiment. After the tested compound was delivered to rats by intravenous administration and intragastric administration, respectively, the whole blood samples were collected at different time point and the plasma was separated. The concentration of compound in plasma was determined by liquid chromatography-tandem mass spectrometry.

(1) Administration Regimen

Six healthy male SD rats with the weight of 200-220 g were randomly divided into 2 groups, each of which has three rats. The rats in each group were administered with the tested compound by gavage or intravenous injection, respectively. Details are shown in table 4.

TABLE 4

| | | administration regimen | | | |
|---|---|---|---|---|---|
| Group | Number of animals | Compound | Administration route | Administration dose | Administration volume |
| 1 | 3 | DC037029 | gavage | 20 | 10 |
| 2 | 3 | DC037029 | vein | 10 | 5.0 |

The compound was dissolved in 10% DMSO/10% Tween/10% normal saline.

The rats are fasted for 12 h and can drink water ad libitum before test. 2 h after dosing, the rats ate all together. The time point for collecting blood samples and the sample processing are listed as follows.

Intragastric administration time: 0.25, 0.5, 1.0, 2.0, 3.0, 5.0, 7.0, 9.0 and 24 h after administration.

Intravenous administration time: 5 min, 0.25, 0.5, 1.0, 2.0, 3.0, 5.0, 7.0, 9.0 and 24 h after administration. At above time point, 0.3 ml venous blood was taken from retrobulbar venous plexus of the rat and loaded into heparinization tube. After centrifuged at 1000 rpm for 5 min, the plasma was separated and frozen at −20° C. in a refrigerator.

(2) Pharmacokinetic Results

Figure 2A:
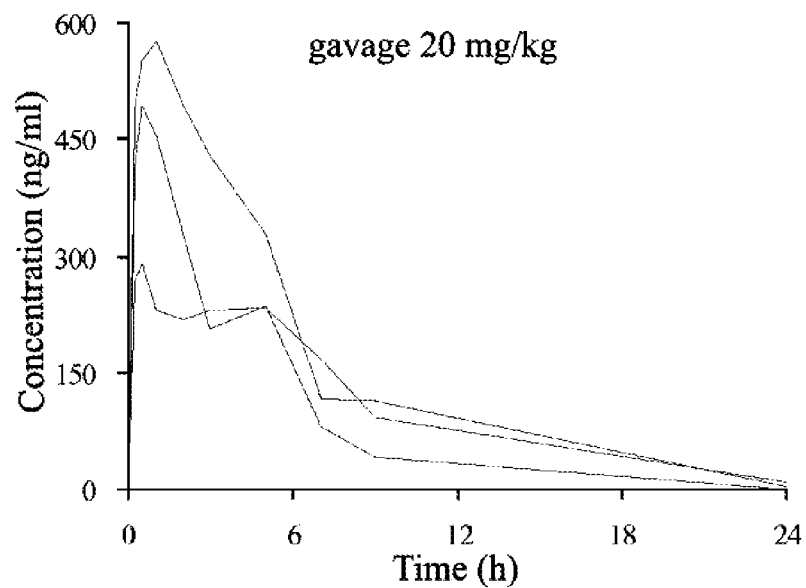
FIG. 2a-2c is a plasma concentration vs time curve after DC037029 is intravenously and orally administered in rats.
Figure 2B:
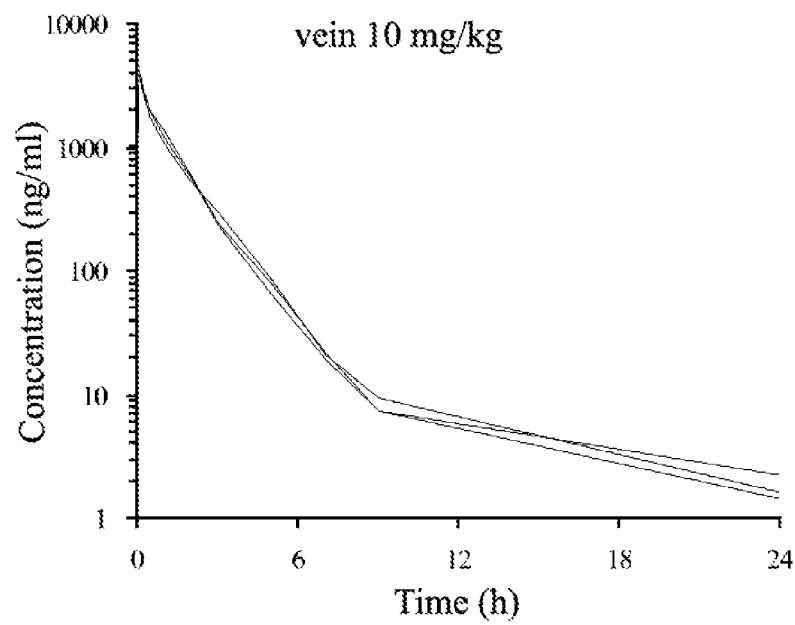
Figure 2C:
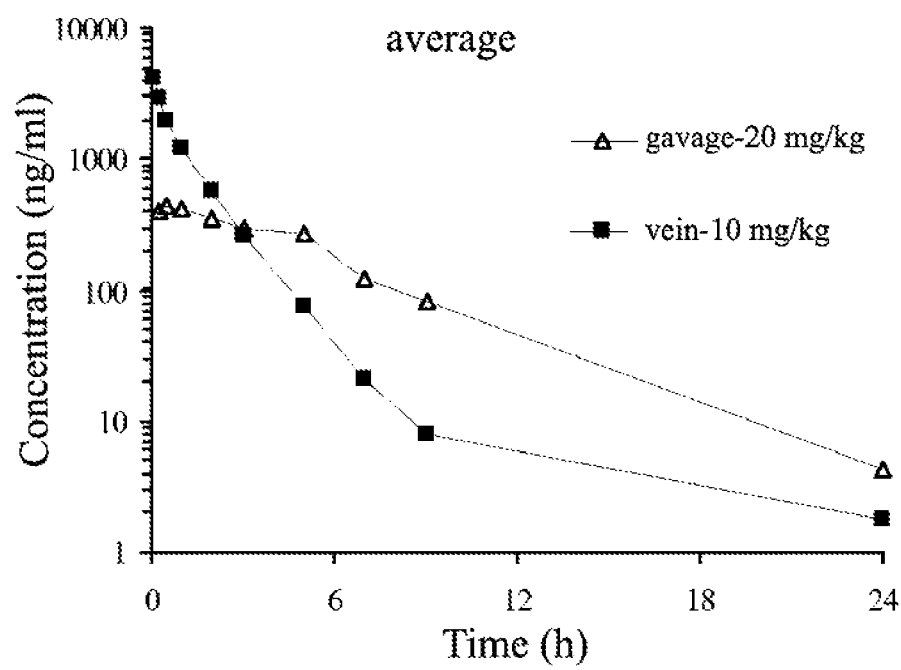

After the rats were administrated with DC037029 by gavage or intravenous injection, respectively, the concentrations of the medicament in plasma were showed in table 5 and 6, the corresponding pharmacokinetic parameters were showed in table 7 and 8, and the curves of plasma concentration vs time were showed in FIG. 2a-2c.

After 20 mg/kg of DC037029 was administered through gavage, the time $T_{max}$ for the plasma concentration in rats reaching the peak concentration is 0.67±0.29 h, the peak concentration $C_{max}$ is 453±147 ng/ml, the area AUC$_{0-t}$ below the curve of plasma concentration vs time is 2867±798 ng·h/ml, and the elimination half-life $t_{1/2}$ is 3.26±0.82 h.

After 10 mg/kg DC037029 was administered through intravenous injection, AUC$_{0-t}$ is 4196±141 ng·h/ml, $t_{1/2}$ is 5.44±0.85 h, plasma clearance rate CL is 2.38±0.08 L/h/kg, steady state distribution volume Vss is 3.49±0.24 L/kg;

After 20 mg/kg of DC037029 was administered through gavage in rat, absolute bioavailability is lavage 34.2%.

TABLE 5

Plasma concentration (ng/mL) of rats after 20 mg/kg of DC037029 was administered through gavage

| the number of the animal | time (h) | | | | | | | | | |
|---|---|---|---|---|---|---|---|---|---|---|
| | 0.0 | 0.25 | 0.5 | 1.0 | 2.0 | 3.0 | 5.0 | 7.0 | 9.0 | 24.0 |
| 1 | BLQ | 416 | 494 | 455 | 326 | 207 | 236 | 80.3 | 41.3 | 1.26 |
| 2 | BLQ | 493 | 553 | 575 | 492 | 431 | 330 | 118 | 113 | 1.90 |
| 3 | BLQ | 268 | 289 | 230 | 218 | 231 | 233 | 169 | 91.9 | 9.67 |
| average | | 392 | 445 | 420 | 345 | 289 | 266 | 122 | 82.2 | 4.28 |
| standard deviation | | 114 | 139 | 175 | 138 | 123 | 55 | 44 | 37.1 | 4.68 |

TABLE 6

Plasma concentration (ng/mL) of rats after 10 mg/kg of DC037029 was administered through intravenous injection

| the number of the animal | time (h) | | | | | | | | | |
|---|---|---|---|---|---|---|---|---|---|---|
| | 0.083 | 0.25 | 0.5 | 1.0 | 2.0 | 3.0 | 5.0 | 7.0 | 9.0 | 24.0 |
| 4 | 4169 | 2766 | 1788 | 1047 | 527 | 294 | 83.7 | 21.1 | 9.26 | 1.61 |
| 5 | 3837 | 2874 | 1984 | 1365 | 596 | 243 | 77.2 | 21.7 | 7.41 | 1.41 |
| 6 | 4576 | 3010 | 2055 | 1211 | 590 | 228 | 65.0 | 19.2 | 7.31 | 2.26 |
| average | 4194 | 2883 | 1942 | 1207 | 571 | 255 | 75.3 | 20.7 | 8.00 | 1.76 |
| standard deviation | 170 | 122 | 138 | 159 | 38 | 34 | 9.5 | 1.3 | 1.10 | 0.45 |

TABLE 7

Pharmacokinetic parameters of rats after 20 mg/kg of DC037029 was administered through gavage

| the number of the animal | $T_{max}$ (h) | $C_{max}$ (ng/mL) | $AUC_{0-t}$ (ng · h/mL) | $AUC_{0-\infty}$ (ng · h/mL) | MRT (h) | $t_{1/2}$ (h) | F (%) |
|---|---|---|---|---|---|---|---|
| 1 | 0.50 | 494 | 2260 | 2265 | 4.00 | 2.89 | |
| 2 | 1.00 | 575 | 3771 | 3779 | 4.67 | 2.70 | |
| 3 | 0.50 | 289 | 2570 | 2629 | 6.45 | 4.20 | |
| average | 0.67 | 453 | 2867 | 2891 | 5.04 | 3.26 | 34.2 |
| standard deviation | 0.29 | 147 | 798 | 790 | 1.27 | 0.82 | |
| CV (%) | 43.3 | 32.6 | 27.8 | 27.3 | 25.1 | 25.1 | |

TABLE 8

Pharmacokinetic parameters of rats after 10 mg/kg of DC037029 was administered through intravenous injection

| the number of the animal | $AUC_{0-t}$ (ng · h/mL) | $AUC_{0-\infty}$ (ng · h/mL) | MRT (h) | $t_{1/2}$ (h) | CLz (L/h/kg) | Vss (L/kg) |
|---|---|---|---|---|---|---|
| 4 | 4034 | 4046 | 1.53 | 5.01 | 2.47 | 3.78 |
| 5 | 4262 | 4272 | 1.42 | 4.88 | 2.34 | 3.33 |
| 6 | 4292 | 4313 | 1.46 | 6.42 | 2.32 | 3.38 |
| average | 4196 | 4210 | 1.47 | 5.44 | 2.38 | 3.49 |
| standard deviation | 141 | 144 | 0.05 | 0.85 | 0.08 | 0.24 |
| CV (%) | 3.4 | 3.4 | 3.6 | 15.7 | 3.5 | 7.0 |

The above results for pharmaceutical experiments indicate that the compounds of the invention have better metabolic properties than l-SPD, especially higher bioavailability and action time, thereby overcoming the defects of l-SPD, such as difficulties in oral absorption, low bioavailability and the like. Especially, oral bioavailability of the compounds of the invention is improved nearly five times compared with that of prodrug thereof (according to CN101037436, the oral bioavailability of l-SPD is 6.83%), which facilitates the preparation of compounds with better drug properties.

Radioligand Binding Assays

The affinity of compounds to $D_1$ and $D_2$ dopamine receptors were determined by competition binding assays. Membrane homogenates of HEK293T cells were stably transfected with $D_1$, or $D_2$ receptors. Duplicated tubes were incubated at 30° C. for 50 mins (for $D_1$, and $D_2$) with increasing concentrations of respective compound and with [$^3$H]SCH23390 (for $D_1$ dopamine receptors), or [$^3$H]Spiperone (for dopamine $D_2$ receptor) in a final volume of 200 μL binding buffer containing 50 mM Tris, 4 mM $MgCl_2$, pH 7.4. Nonspecific binding was determined by parallel incubations with either 10 μM SCH23390 for $D_1$, or Spiperone for $D_2$ receptors respectively. The reaction was started by addition of membranes (15 ng/tube) and stopped by rapid filtration through Whatman GF/B glassfiber filter and subsequently washed with cold buffer (50 mM Tris, 5 mM EDTA, pH 7.4) using a Brandel 24-well cell harvester. Scintillation cocktail was added and the radioactivity was determined in a MicroBeta liquid scintillation counter. The $IC_{50}$ and Ki values were calculated by nonlinear regression (PRISM, Graphpad, San Diego, Calif.) using a sigmoidal function. The inhibition and Ki values of tested compounds are listed in Table 9.

TABLE 9

The Ki values of tested compounds

| Compound No. | configuration | $D_1$ Inhibition (%) or $K_i$ (nM) | $D_2$ Inhibition (%) or $K_i$ (nM) |
|---|---|---|---|
| DC037078 | S | 64.12 ± 4.43 | 39.50% |
| DC037076 | S | 74.51 ± 3.85 | 1.02% |
| DC037079 | S | 2.53 ± 0.16 | 83.31% |
| DC037081 | S | 17.29 ± 0.54 | 146.9 ± 10.2 |
| DC037031 | S | 28.91 ± 2.73 | 160.9 ± 21.1 |
| DC037013 | S | 23.65 ± 1.18 | 85.6% |
| DC037030 | S | 3.70 ± 0.26 | 74.27% |
| DC037035 | S | 6.72 ± 0.34 | 84.30% |

[$^{35}$S]GTPγS Binding Assays

For detecting the agonism action of the compounds, the [$^{35}$S]GTPγS binding assay was performed at 30° C. for 40 mins in reaction buffer containing 50 mM Tris, pH 7.5, 5 mM $MgCl_2$, 1 mM EDTA, 100 mM NaCl and 1 mM (DL)-dithiothreitol (DTT). The assay mixture (200 μL) contained 30 μg of membraneprotein, 0.1 nM [$^{35}$S]GTPγS, and 40 μM guanosine triphosphate (GDP) with various concentration of the compound. The $D_1$ receptor agonist SKF38393 and sntagonist SCH23390 were used for reference. Non specific binding was measured in the presence of 100 μM 50-guanylimidodiphosphate (Gpp(NH)p). The reaction was terminated by adding 3 mL of ice-cold washing buffer (50 mM Tris, pH 7.5, 5 mM $MgCl_2$, 1 mM EDTA, and 100 mM NaCl) and was rapidly filtered with GF/C glass fiber filters (Whatman) and rinsed for three times. Filters were dried and radioactivity was determined by liquid scintillation counting. The results are summarized in Table 10. The results show that DC037030 and DC037079 have good $D_1$ receptor selectivity and $D_1$ receptor antagonistic activity.

TABLE 10

| [$^{35}$S]GTPγS binding assays of DC037030 and DC037079 for $D_1$ receptor | | | | |
|---|---|---|---|---|
| | D1 agonist | | D1 antagonist | |
| Compound No. | EC$_{50}$ (nM) | Emax % | IC$_{50}$ (μM) | Imax % |
| DC037030 | — | — | 1.9 ± 0.4 | 86.8 ± 1.6 |
| DC037079 | — | — | 1.4 ± 0.2 | 94.2 ± 1.5 |
| SKF38393 | 247.5 ± 26.1 | 100 | — | — |
| SCH23390 | — | — | 0.74 ± 0.05 | 81.0 ± 2.7 |

INDUSTRIAL APPLICABILITY

Hexahydrodibenzo[a,g]quinolizine compounds of the invention have relatively low toxicity and good solubility.

The preparation method for hexahydrodibenzo[a,g]quinolizine compounds of the invention has many advantages, such as mild reaction condition, abundant and readily-available raw materials that can be easily found, simple operation and post-processing, good selectivity, etc.

Hexahydrodibenzo[a,g]quinolizine compounds of the invention have excellent selectivity among different subtypes of serotonin receptors and dopamine receptors.

Therefore, the compounds of the invention can be used in preparing medicaments for treating the diseases relating to nervous system, especially to the dopamine receptors $D_1$ and $D_2$ as well as serotonin receptors 5-HT$_{1A}$ and 5-HT$_{2A}$.

The invention claimed is:

1. A method of treating schizophrenia in a subject in need thereof, the method comprising administering to the subject a pharmaceutical composition comprising one or more pharmaceutically acceptable carriers and a therapeutically effective amount of a chiral hexahydrodibenzo[a,g]quinoline compound of general formula (I):

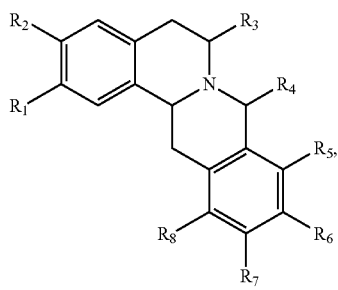

(I)

or an enantiomer, diastereoisomer, or pharmaceutically acceptable organic salt or inorganic salt thereof,
wherein a configuration of the chiral carbon atom labeled "*" is either R or S;
$R_3$ is H, a halogen-substituted or unsubstituted C1-C6 alkyl, a halogen-substituted or unsubstituted C1-C6 alkoxy, or a halogen;
$R_4$ is H or a halogen;
each of $R_5$, $R_6$, and $R_8$ is independently H, a hydroxy, a hydroxy-substituted C1-C6 alkyl, a halogen-substituted or unsubstituted C1-C6 alkyl, a halogen-substituted or unsubstituted C1-C6 alkoxy, a halogen, a C3-C6 cycloalkyl, a halogen-substituted or unsubstituted C2-C6 alkenyloxy, a halogen-substituted or unsubstituted C3-C6 alkynyloxy, a substituted or unsubstituted benzyloxy, $R_{14}$COO—, $R_{15}R_{16}$N—; when $R_5$, $R_6$, or $R_8$ is a substituted or unsubstituted benzyloxy, a substituent for substitution is a C1-C6 alkyl, a halogen, or a C1-C6 alkoxy; wherein $R_{14}$ is H, or a halogen-substituted or unsubstituted C1-C6 alkyl; each of $R_{15}$ and $R_{16}$ is independently H, or a substituted or unsubstituted C1-C6 alkyl, and when $R_{15}$ or $R_{16}$ is a substituted or unsubstituted C1-C6 alkyl, a substituent for substitution is a C1-C6 alkyl, a halogen, or a C1-C6 alkoxy;
$R_7$ is H, a halogen substituted or unsubstituted C1-C6 alkoxy, a halogen substituted or unsubstituted C2-C6 alkenyloxy, or a halogen-substituted or unsubstituted C3-C6 alkynyloxy;
$R_1$ and $R_2$ together form a substituted or unsubstituted 5-membered heterocycle, a substituent for substitution is a halogen, or a halogen-substituted or unsubstituted C1-C6 alkyl, C2-C6 alkenyl, or C2-C6 alkynyl; and the heterocycle contains two oxygen atoms;
or any two adjacent substituents of $R_5$, $R_6$, $R_7$ and $R_8$ can together form a substituted or unsubstituted 5-7 membered heterocycle, wherein a substituent for substitution is a halogen, or a halogen-substituted or unsubstituted C1-C6 alkyl, C2-C6 alkenyl, or C2-C6 alkynyl; and the heterocycle contains 1-3 heteroatom(s) selected from N, O or S.

2. The method according to claim 1,
wherein
$R_3$ is H, or a halogen-substituted or unsubstituted C1-C6 alkyl;
$R_5$ is H, a halogen-substituted or unsubstituted C1-C6 alkyl, a halogen-substituted or unsubstituted C1-C6 alkoxy, or a halogen;
$R_6$ is H, a halogen-substituted or unsubstituted C1-C6 alkyl, a halogen-substituted or unsubstituted C1-C6 alkoxy, a hydroxy, or a hydroxy-substituted C1-C6 alkyl;
$R_8$ is H, a hydroxy, a hydroxy-substituted C1-C6 alkyl, a halogen-substituted or unsubstituted C1-C6 alkoxy, a halogen-substituted or unsubstituted C1-C6 alkyl, or a halogen;
or $R_6$ and $R_7$ together form a fluoro-, chloro- or bromo-substituted 5-7 membered heterocycle, and the heterocycle contains 1-2 heteroatom(s) selected from N, O or S.

3. The method according to claim 2,
wherein
$R_3$ is H or a C1-C6 alkyl;
$R_4$ is H;
$R_5$ is H, a C1-C6 alkyl, a C1-C6 alkoxy, or a halogen;
$R_6$ is H, a C1-C6 alkyl, a C1-C6 alkoxy, a hydroxy, or a hydroxy-substituted C1-C6 alkyl;
$R_7$ is H or a C1-C6 alkoxy;
$R_8$ is H, a hydroxy-substituted C1-C6 alkyl, a C1-C6 alkoxy, a C1-C6 alkyl, or a halogen; and the halogen is F, Br or Cl;
or $R_6$ and $R_7$ can together form a fluoro-, chloro- or bromo-substituted or unsubstituted 5- or 6-membered heterocycle and the heterocycle contains 1-2 heteroatom(s) selected from N, O or S.

4. The method according to claim 1,
wherein the configuration of chiral C atom designated "*" which is not linked with $R_3$ or $R_4$ in the parent nucleus of the compound of general formula (I) is S.

5. The method according to claim 1,
wherein the configuration of chiral C atom designated "*" which is not linked with $R_3$ or $R_4$ in the parent nucleus of the compound of general formula (I) is R.

6. The method according to claim 1,
wherein R$_6$ is methoxyl, and R$_7$ is methoxyl.

7. The method according to claim 1,
wherein R$_8$ is a methoxyl, a hydroxy-substituted C1-C6 alkyl, or a halogen.

8. The method according to claim 1,
wherein one to three of R$_5$, R$_6$, and R$_8$ is a methoxyl, a hydroxy-substituted C1-C6 alkyl, or C1-C6 alkyl.

9. A chiral hexahydrodibenzo[a,g]quinoline compound, or an enantiomer, diastereoisomer, or pharmaceutically acceptable organic salt or inorganic salt thereof, wherein the compound is selected from the group consisting of:

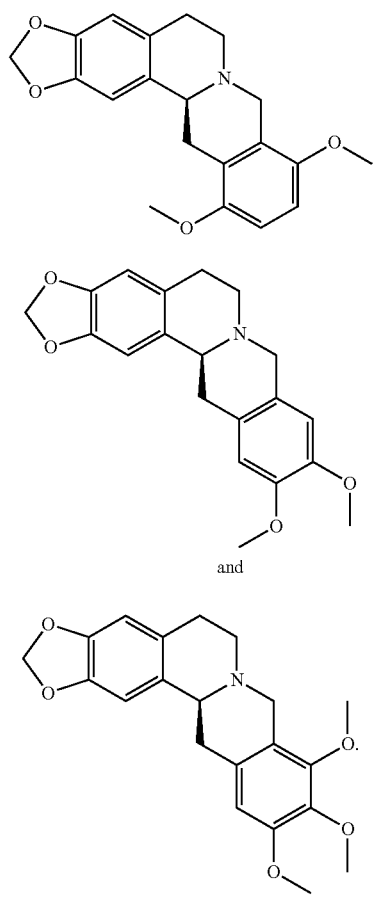

10. A chiral hexahydrodibenzo[a,g]quinoline compound, or an enantiomer, diastereoisomer, or pharmaceutically acceptable organic salt or inorganic salt thereof, wherein the compound is

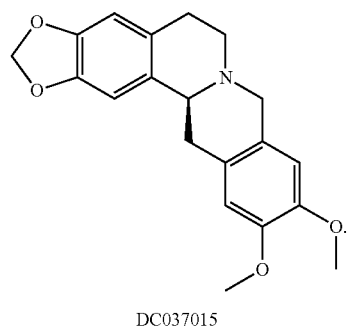 [SMILES: COc1cc2c(cc1OC)CN1CCc3cc4c(cc3[C@@H]1C2)OCO4]

11. A pharmaceutical composition comprising a therapeutically effective amount of the chiral hexahydrodibenzo[a,g]quinoline compound, or the enantiomer, diastereoisomer, or pharmaceutically acceptable organic salt or inorganic salt thereof according to claim 9, and one or more pharmaceutically acceptable carriers.

12. A preparation method of the chiral hexahydro-dibenzo[a,g]quinoline compound according to claim 1, wherein the compound is prepared according to a first reaction route or a second reaction route:

the first reaction route:

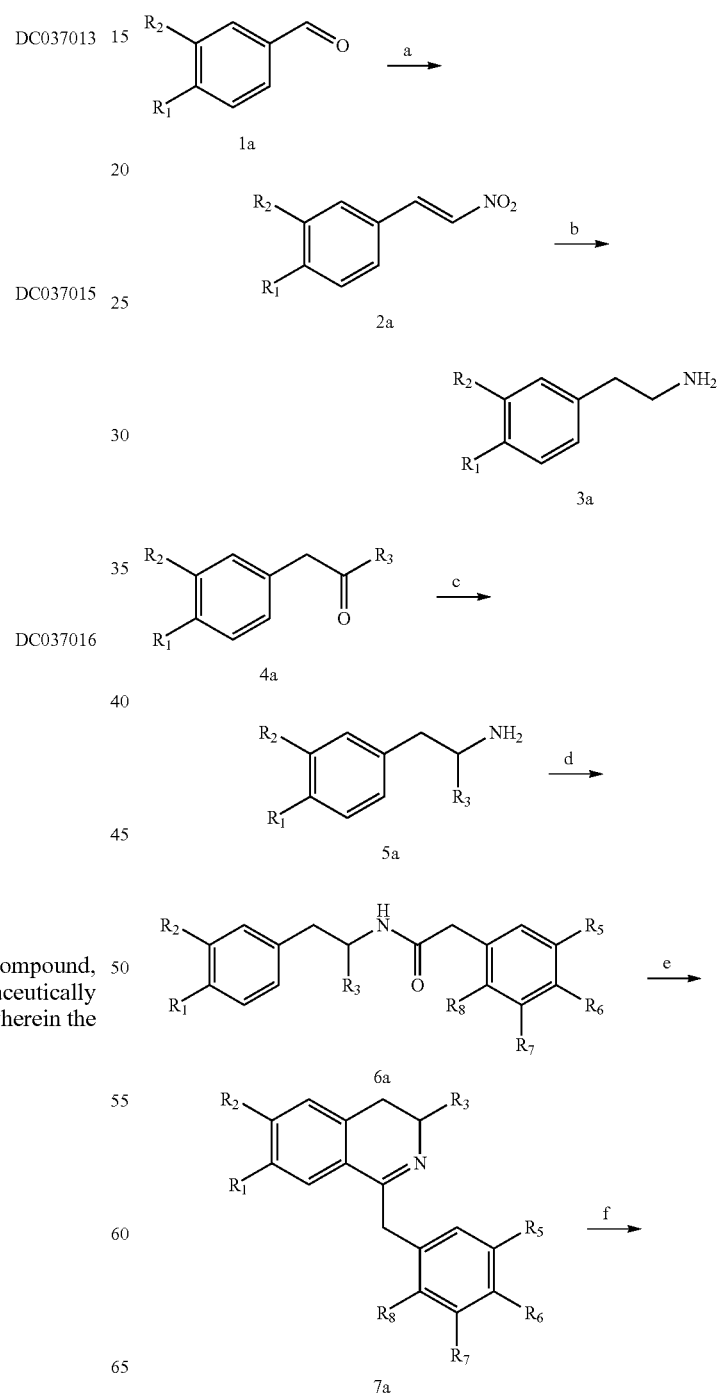

-continued

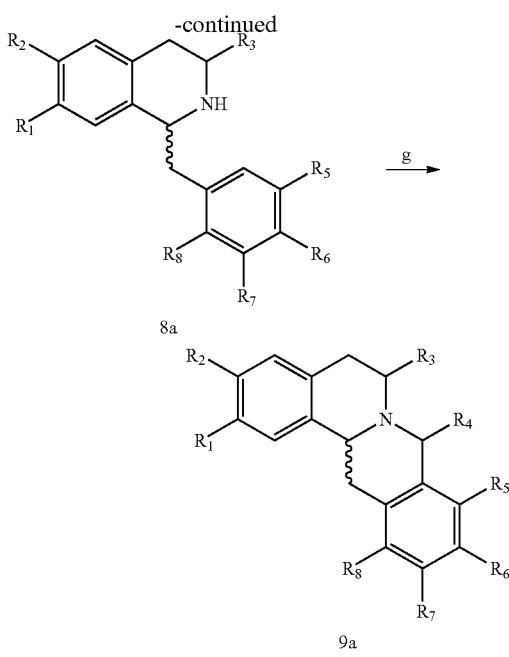

reagents and reaction conditions: a) acetic acid, nitromethane, ammonium acetate, 80° C.; b) lithium aluminum hydride, anhydrous tetrahydrofuran, reflux; c) ammonium formate, anhydrous methanol, palladium carbon, hydrogen, room temperature; d) 1-ethyl-3-(3-dimethylpropylamine) carbodiimide, anhydrous dichloromethane, triethylamine, room temperature; e) nitrogen protection, phosphorus oxychloride, acetonitrile, reflux; and f) catalyst (Noyori), N, N-dimethylformamide, triethylamine/formic acid or sodium borohydride; g) aldehyde, acid conditions;

the preparation of Compound 2a: a substrate is dissolved in an appropriate amount of glacial acetic acid, to which 1.2-2.0 equivalent of ammonium acetate is added to form a mixture, 5-10 equivalent of nitromethane is added to the mixture at room temperature and reacted in an oil bath, and then the reaction system is cooled to room temperature and a large amount of solid is precipitated, Compound 2a is obtained by suction filtration;

the preparation of Compound 3a: lithium aluminum hydride is suspended in an appropriate amount of anhydrous tetrahydrofuran and placed in an ice water bath; a solution of unsaturated nitro-compound 2a in anhydrous tetrahydrofuran is slowly added dropwise; after the addition is completed, the reaction solution is transferred into an oil bath, refluxed, and then cooled to room temperature, then the defined amount of water is added slowly and a clear solution is obtained by filtration, after dried over anhydrous sodium sulfate and evaporated to dryness, an oily Compound 3a is obtained;

the preparation of Compound 5a: a substrate 4a is dissolved in an appropriate amount of anhydrous methanol, and 1.5-3.0 equivalent of ammonium formate is added; 10% palladium carbon is added under stirring and hydrogen is ventilated at the same time; the reaction is carried out at room temperature overnight; after the palladium carbon is removed by filtration, the solution is evaporated to dryness to give an oily Compound 5a;

the preparation of Compound 6a: at room temperature, the substrate 3a or 5a is condensed with R5-, R6-, R7-, and R8-substituted phenylacetic acid in the presence of 1-ethyl-3(3-dimethyl-propylamine) carbodiimide or triethylamine, and anhydrous dichloromethane, then the product is purified by column chromatography or recrystallized by using ethanol to give Compound 6a;

the preparation of Compound 7a: under $N_2$, the substrate 6a in acetonitrile used as solvent is refluxed under the action of phosphorus oxychloride to obtain Compound 7a;

the preparation of Compound 8a: catalyst Noyori as the chiral reducing reagent, and N, N-dimethylformamide, and triethylamine/formic acid are used to carry out the asymmetric reduction reaction of Compound 7a, thereby obtaining Compound 8a with a single configuration;

the preparation of Compound 9a: the intermediate Compound 8a is reacted with aldehyde under acidic condition to obtain Compound 9a;

the second reaction route:

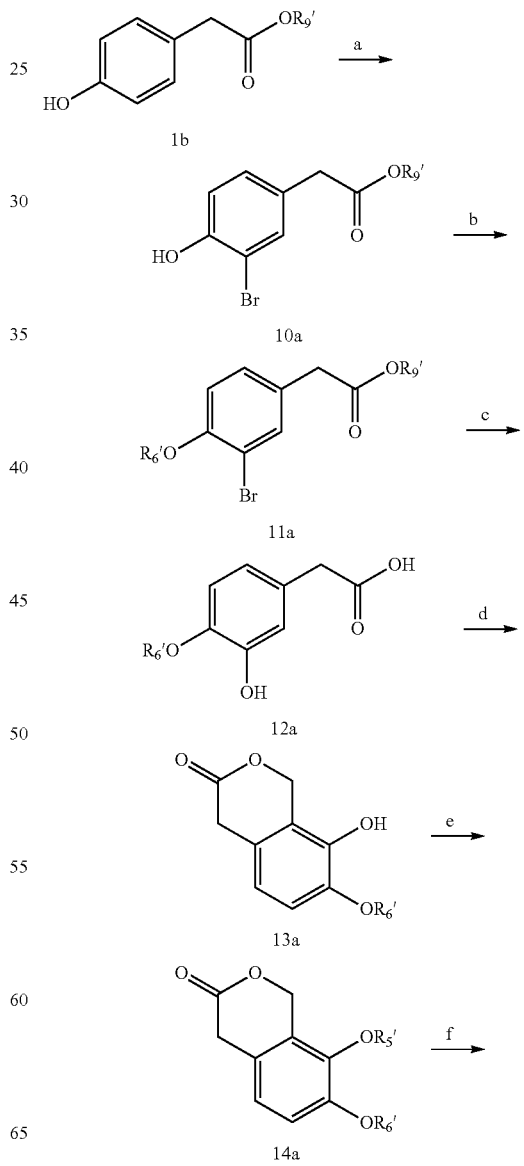

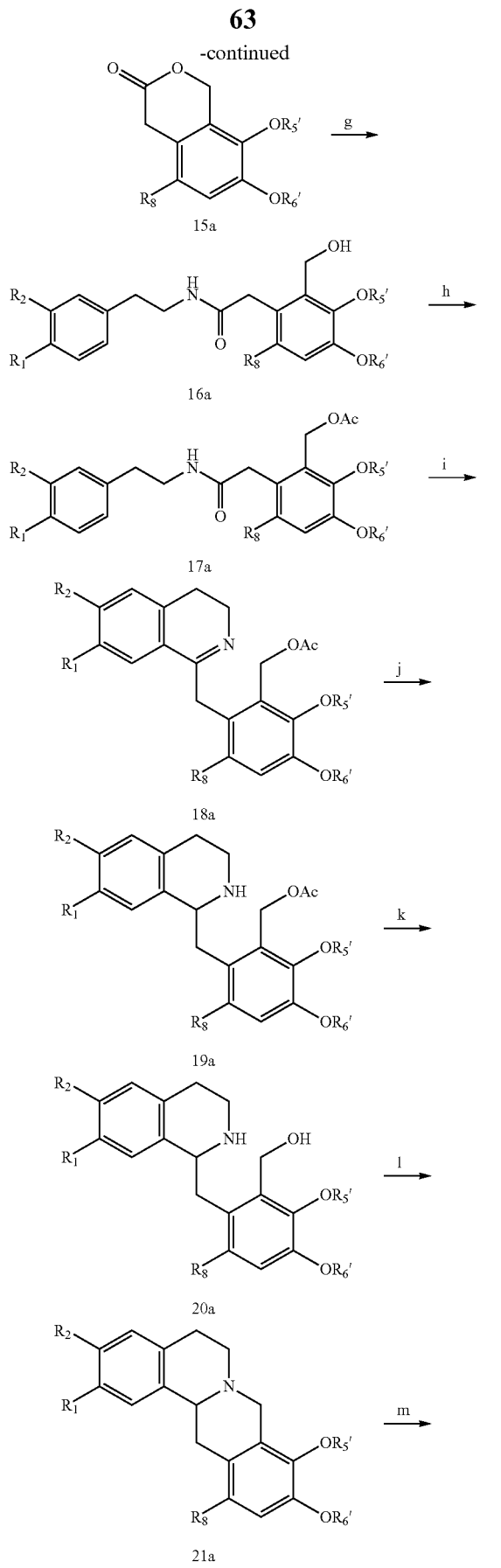

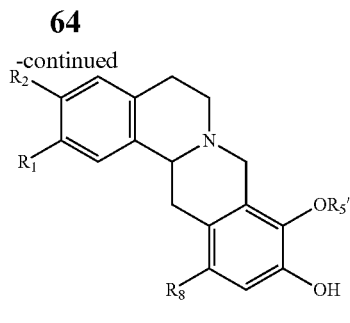

wherein R9' is a C1-C6 alkyl, R5' is a halogen-substituted or unsubstituted C1-C6 alkyl, or a substituted or unsubstituted benzyl, R6' is a halogen-substituted or unsubstituted C1-C6 alkyl, or a substituted or unsubstituted benzyl, wherein a substituent for substitution is a C1-C6 alkyl, a halogen or a C1-C6 alkoxy;

reaction reagents and conditions: a) room temperature, acetic acid, liquid bromine; b) alkylating reagent/benzylating reagent, solvent, organic alkali/inorganic alkali; c) catalyst containing copper or copper ion, alkaline condition, water, 90° C. to 150° C. of reaction temperature, pH 1-3; d) phenylboronic acid, toluene, paraformaldehyde and water; e) solvent, alkylating reagent/benzylating reagent, organic alkali/inorganic alkali; f) nitrating reagent; g) phenethylamine containing at least one electron-donating substituent, ethanol, reflux; h) solvent, acylating reagent, inorganic/organic alkali; i) solvent, condensing agent; j) sodium borohydride, sodium cyanoborohydride or sodium acetoxy borohydride/catalyst (Noyori), N, N-dimethylbenzamide, triethylamine and formic acid; k) solvent, inorganic alkali; l) solvent, halogenating reagent, organic/inorganic alkali; m) reflux, concentrated hydrochloric acid, ethanol/BCl₃, dichloromethane;

the preparation of Compound 10a: at room temperature, Compound 1b is reacted with liquid bromine to obtain product Compound 10a;

the preparation of Compound 11a: under the action of organic/inorganic alkali, Compound 10a is reacted with an alkylating reagent or a benzylating reagent in solvent to obtain Compound 11a, wherein said solvent can be selected from the following group: methanol, ethanol, acetone, N, N-dimethylformamide, dimethyl sulfoxide, tetrahydrofuran, dichloromethane, chloroform, dioxane; said alkylating reagent is dimethyl sulfate, methyl iodide, diazomethane, or trifluoro methyl sulfonic acid methyl ester; said benzylating reagent is a alkoxy-, alkyl-, nitro- or halogen-substituted benzyl chloride or benzyl bromide; said inorganic alkali is selected from the following group: sodium hydroxide, potassium hydroxide, cesium hydroxide, barium hydroxide, potassium hydride, sodium hydride, sodium tert-butoxide, potassium tert-butoxide, potassium carbonate, sodium carbonate and calcium carbonate; and said organic alkali is selected from triethylamine, diisopropylethylamine, pyridine, N, N-dimethylaniline, N, N-dimethyl-pyridine;

the preparation of Compound 12a: a catalyst used in the reaction is one or two of the following: copper sulfate, copper oxide, copper powder, copper chloride, copper bromide, copper iodide, copper carbonate, copper nitrate, copper hydroxide and the like; the reaction is conducted in the presence of alkali, such as sodium hydroxide, potassium hydroxide, cesium hydroxide, calcium hydroxide, barium hydroxide or quaternary ammonium hydroxide; the reaction can be, but not necessarily, finished with the help of microwave, the reaction temperature is between 90° C. and 150° C.; and Compound 12a can be obtained by adjusting the pH value of reaction mixture to 1-3 after the reaction is finished;

the preparation of Compound 13a: 2.0-3.0 equivalent of phenylboronic acid is refluxed in toluene, and then paraformaldehyde is added and reacted in toluene; the solvent is evaporated and the reaction is conducted in water; the reaction mixture is extracted with dichloromethane; then the extract liquid is dried over sodium sulfate and the solvent is evaporated; after stirred in diethyl ether, Compound 13a is obtained by filtration;

the preparation of Compound 14a: Compound 13a is reacted with an alkylating reagent, an acylating reagent or a benzylating reagent in a solvent under the action of organic/inorganic alkali to obtain Compound 14a; said solvent is selected from the following group: methanol, ethanol, acetone, N,N-dimethylformamide, dimethyl sulfoxide, tetrahydrofuran, dichloromethane, chloroform, and dioxane; said alkylating reagent is dimethyl sulfate, methyl iodide, diazomethane, or methyl trifluoromethanesulfonate; said acylating reagent is acetyl chloride, acetic anhydride, benzoyl chloride, trifluoroacetic acid anhydride; said benzylating reagent is alkoxy-, alkyl-, nitro-, or halogen-substituted benzyl chloride or benzyl bromide; said inorganic alkali is selected from sodium hydroxide, potassium hydroxide, cesium hydroxide, barium hydroxide, potassium hydride, sodium hydride, sodium tert-butoxide, potassium tert-butoxide, potassium carbonate, sodium carbonate or calcium carbonate; and said organic alkali is selected from triethylamine, diisopropylethylamine, pyridine, N, N-dimethylaniline, or N, N-dimethyl-pyridine;

the preparation of Compound 15a: under the action of a nitrating reagent, Compound 15a, nitration product, is obtained from Compound 14a; the reaction temperature is between 0° C. and 25° C., and the reaction time is 10 minutes to 12 hours; said nitrating reagent is a mixture of concentrated sulfuric acid and nitric acid, a mixture of nitric acid, sodium nitrate and concentrated sulfuric acid, a mixture of concentrated sulfuric acid and potassium nitrate, a mixture of concentrated sulfuric acid and sodium nitrite, or a mixture of acetic acid and concentrated nitric acid;

the preparation of Compound 16a: Compound 15a with the same equivalent of phenylethylamine are added to an appropriate amount of ethanol and refluxed overnight; ethanol is evaporated and the crude product is recrystallized in a recrystallization solvent; said recrystallization solvent is selected from one or two of the followings: ethyl acetate, n-hexane, benzene, toluene, petroleum ether, ethanol, isopropanol, methanol, chloroform, and xylene;

the preparation of Compound 17a: Compound 16a is dissolved in solvent and organic/inorganic alkali is added; an acylating agent is slowly added at 0° C.; then the reaction proceeded at room temperature and water is added; the reaction mixture is extracted with dichloromethane and dichloromethane layer is washed with saturated saline solution; the extract liquid is dried over sodium sulfate and evaporated to dryness, thereby obtaining Compound 17a; wherein said acylating agent is acetic anhydride, acetyl chloride, trifluoroacetic anhydride, trichloroacetic anhydride, methyl chloroformate, or ethyl chloroformate; said organic alkali is triethylamine, diisopropyl ethylamine, pyridine, N,N-dimethylaniline, or N,N-dimethyl pyridine; and said inorganic alkali is potassium carbonate, sodium carbonate, sodium bicarbonate, potassium bicarbonate, sodium hydroxide, or potassium hydroxide;

the preparation of Compound 18a: Compound 17a is dissolved in a solvent and heated to reflux; a condensing reagent is added to the reaction solution; the reaction is monitored by TLC; most of solvent is evaporated, and the reaction solution is neutralized with saturated sodium bicarbonate, extracted for three times with dichloromethane, dried over sodium sulfate and evaporated to dryness; and the product is directly used in next reaction without further purification; wherein said solvent is anhydrous acetonitrile, anhydrous toluene, or benzene; and said condensing reagent is phosphorus oxychloride, phosphorus oxybromide, or phosphorus pentoxide;

the preparation of Compound 19a: the imine Compound 18 obtained above is asymmetrically reduced by using Noyori catalyst in anhydrous N, N-dimethylformamide in the presence of triethylamine and formic acid to obtain chiral amine 19a; the reaction is carried out at room temperature for 7 to 12 hours; after the reaction is finished, the reaction solution is neutralized with saturated aqueous sodium bicarbonate solution, extracted with ethyl acetate, and dried over sodium sulfate; or the achirality reduction is conducted by using sodium borohydride, sodium cyanoborohydride or sodium acetoxy borohydride;

the preparation of Compound 20a: Compound 19a is dissolved in a solvent and an inorganic alkali is added to above solution, then the reaction is conducted at room temperature and solid precipitates, and the precipitate is filtered and dried, thereby obtaining the target Compound 20a, wherein said inorganic alkali is sodium hydroxide, potassium hydroxide, cesium hydroxide or potassium carbonate; said solvent may be a mixture of water and one of ethanol, methanol, N,N-dimethylformamide;

the preparation of Compound 21a: in a solvent, Compound 20a is halogenated with a halogenating agent under alkaline condition, and then product 21a is obtained through ring-closing reaction, wherein said halogenating agent is thionyl chloride, thionyl bromide, phosphorus trichloride, phosphorus tribromide, phosphorus pentachloride, or phosphorus pentabromide; said solvent is dichloromethane, tetrahydrofuran, diethyl ether, or chloroform; said alkaline condition is an organic alkali or an inorganic alkali, wherein the organic alkali is triethylamine, pyridine, diisopropylethylamine, or the inorganic alkali is potassium carbonate, sodium carbonate, sodium bicarbonate, potassium bicarbonate, sodium hydroxide, potassium hydroxide, calcium carbonate, or ammonia;

the preparation of Compound 22a: Compound 21a is dissolved in ethanol and concentrated hydrochloric acid is added to reflux or $BCl_3$ and dichloromethane is added to reflux at low temperature in order to remove R6' protective group to give Compound 22a.

13. The preparation method according to claim 12, wherein, in the second reaction route:
for the preparation of Compound 11a, said solvent is acetone, N, N-dimethylformamide, or tetrahydrofuran;

and said organic alkali is benzyl chloride, benzyl bromide, methyl iodide, dimethyl sulfate or potassium carbonate;

for the preparation of Compound 12a, the catalyst is one or two of the following: copper sulfate, copper oxide, copper powder; and said alkaline condition is sodium hydroxide, potassium hydroxide, or cesium hydroxide;

for the preparation of Compound 14a, the solvent is acetone, tetrahydrofuran, or N,N-dimethylformamide; said alkylating reagent is dimethyl sulfate, or methyl iodide; said acylating reagent is acetyl chloride, or acetic anhydride; and said inorganic alkali is potassium carbonate;

for the preparation of Compound 15a, said nitrating reagent is a mixture of acetic acid and concentrated nitric acid;

for the preparation of Compound 16a, said solvent for recrystallization is toluene, ethanol, or xylene;

for the preparation of Compound 17a, said acylating agent is acetic anhydride, or acetyl chloride; said organic alkali is triethylamine, diisopropyl ethylamine, or pyridine; and said solvent is dichloromethane, tetrahydrofuran, diethyl ether, or toluene;

for the preparation of Compound 18a, said condensing reagent is phosphorus oxychloride, and said solvent is anhydrous acetonitrile;

for the preparation of Compound 20a, said inorganic alkali is sodium hydroxide and said solvent is a mixture of water and ethanol or methanol; and for the preparation of Compound 22a, ethanol or concentrated hydrochloric acid is used to remove $R6'$ protective group.

* * * * *